(12) United States Patent
Johnsson et al.

(10) Patent No.: US 12,018,157 B2
(45) Date of Patent: Jun. 25, 2024

(54) TUNABLE PHOTOACTIVATABLE SILICON RHODAMINE FLUOROPHORES

(71) Applicant: SPIROCHROME AG, Stein am Rhein (CH)

(72) Inventors: Kai Johnsson, Munich (DE); Luc Reymond, Lausanne (CH); Michelle Frei, Munich (DE); Stefan Pitsch, Stein am Rhein (CH)

(73) Assignee: SPIROCHROME AG, Stein am Rhein (CH)

( * ) Notice: Subject to any disclaimer, the term of this patent is extended or adjusted under 35 U.S.C. 154(b) by 1039 days.

(21) Appl. No.: 16/956,596

(22) PCT Filed: Dec. 20, 2018

(86) PCT No.: PCT/EP2018/086440
§ 371 (c)(1),
(2) Date: Jun. 21, 2020

(87) PCT Pub. No.: WO2019/122269
PCT Pub. Date: Jun. 27, 2019

(65) Prior Publication Data
US 2023/0147145 A1 May 11, 2023

(30) Foreign Application Priority Data

Dec. 21, 2017 (EP) ..................................... 17209895
Apr. 19, 2018 (EP) ..................................... 18168134

(51) Int. Cl.
*C09B 62/00* (2006.01)
*C09B 11/28* (2006.01)
(Continued)

(52) U.S. Cl.
CPC .............. *C09B 11/28* (2013.01); *C09K 11/06* (2013.01); *G01N 1/30* (2013.01); *G01N 21/6428* (2013.01);
(Continued)

(58) Field of Classification Search
CPC . C09B 11/28; C09K 11/06; C09K 2211/1018; G01N 1/30; G01N 21/6428;
(Continued)

(56) References Cited

U.S. PATENT DOCUMENTS

2011/0077394 A1    3/2011  Bell et al.

FOREIGN PATENT DOCUMENTS

WO        2012083064           6/2012
WO     WO 2012/083064 A1  *   6/2012  ............ A61M 37/00
(Continued)

OTHER PUBLICATIONS

STIC Search Report dated Oct. 20, 2023.*
(Continued)

*Primary Examiner* — Eisa B Elhilo
(74) *Attorney, Agent, or Firm* — JMB Davis Ben-David

(57) ABSTRACT

The invention relates to a compound characterized by general formula (100), wherein $R^1$ and $R^6$ are H or F, $R^2$, $R^3$, $R^4$ and $R^5$ can be any substituent, $R^7$, $R^8$, $R^{N1}$, $R^{N2}$, $R^{N3}$ and $R^{N4}$ are a hydrocarbon moiety, one of $R^9$ and $R^{10}$ is hydrogen and the other one is hydrogen or a saturated carbon atom connected to any substituent, and its use in staining and live cell fluorescence imaging.

(Continued)

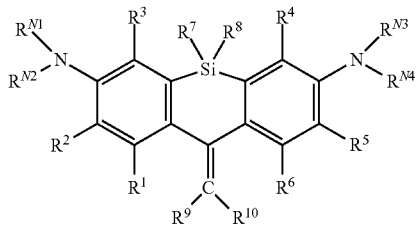

(100)

15 Claims, 6 Drawing Sheets

(51) Int. Cl.
C09K 11/06 (2006.01)
G01N 1/30 (2006.01)
G01N 21/64 (2006.01)
G01N 33/58 (2006.01)

(52) U.S. Cl.
CPC ....... *G01N 21/6456* (2013.01); *G01N 33/582* (2013.01); *C09K 2211/1018* (2013.01); *G01N 2001/302* (2013.01); *G01N 2021/6439* (2013.01)

(58) Field of Classification Search
CPC ............. G01N 21/6456; G01N 33/582; G01N 2001/302; G01N 2021/6439; C07F 7/0816
USPC .......................................................... 8/648
See application file for complete search history.

(56) References Cited

FOREIGN PATENT DOCUMENTS

| WO | 2013029650 | 3/2013 | |
|---|---|---|---|
| WO | WO 2013/029650 A1 * | 3/2013 | ........... G01N 33/582 |
| WO | 2017201531 | 11/2017 | |

OTHER PUBLICATIONS

Yuichiro Koide et al, "Development of an Si-Rhodamine-Based Far-Red to Near-Infrared Fluorescence Probe Selective for Hypochlorous Acid and Its Applications for Biological Imaging", Journal of the American Chemical Society, vol. 133, No. 15, Apr. 20, 2011 (Apr. 20, 2011), p. 5680-5682.

Aaron C et al., "495. Steric Effects in Di- and Tri-arylmethanes. Part VIII.* Electronic Absorption 8pectra of Planar Derivatives of Michler'sHydrol Blue.", Journal of the Chemical Society,Jan. 1, 1963 (Jan. 1, 1963), p. 2655-2662.

* cited by examiner

Table 1: Characteristic values of the compounds:

| Compound | λex | λem | ε (PBS pH = 7.3) | φ (PBS pH = 7.3) |
|---|---|---|---|---|
| PA-SiR 2a | 646 | 668 | - | - |
| SiR* | 645 | 661 | 100'000 | 0.39 |
| PA-SiR -Halo + HaloTag | - | - | 25'000 | 0.37 |

*G. Lukinavičius, K. Umezawa, N. Olivier, A. Honigmann, G. Yang, T. Plass, V. Mueller, L. Reymond, I. R. Corrêa Jr, Z.-G. Luo, et al., *Nat. Chem.* 2013, 5, 132–139.

TUNABLE PHOTOACTIVATABLE SILICON RHODAMINE FLUOROPHORES

CROSS-REFERENCE TO RELATED APPLICATIONS

This is the U.S. National Stage of International Patent Application No. PCT/EP2018/086440 filed on Dec. 20, 2018, which in turn claims the benefit of European Patent Application No. 17209895.6 filed on Dec. 21, 2017 and European Patent Application No. 18168134.7 filed on Apr. 19, 2018.

The present invention relates to a new class of photoactivatable Silicon rhodamine (PA-SiR) fluorophores.

BACKGROUND

Small molecule organic dyes are generally brighter and therefore better suited for single-molecule localisation microscopy (SMLM) than fluorescent proteins, and hence interest in intracellular labelling techniques using synthetic dyes has grown with the advent of super-resolution microscopy. Photoactivatable synthetic dyes are particularly powerful tools for studying cellular processes with high temporal and spatial resolution.

An application of particular interest is the adaption of small molecule dyes to their use with self-labelling protein tags or other protein labelling techniques such as click chemistry with unnatural amino acids, enabling their localization to specific cellular targets.

Rhodamines and their silicon derivatives (SiR) are important classes of fluorophores used in live cell imaging due to their high brightness (high extinction coefficient ($\varepsilon$) and high quantum yield ($\phi$)), their photostability, and their cell permeability. WO2013029650A1 (PCT/EP2011/064750) discusses the present inventors' previous contributions to this field. Photoactivatable ortho-nitrobenzyl analogues can be obtained, but were mostly used in fixed cell microscopy. When applied in live cells, the stoichiometric formation of the coloured and toxic byproduct nitroso-aldehyde is a major disadvantage. In addition, the o-nitrobenzyl group is bulky and adds lipophilicity to the molecule, making the probe less cell permeable than its non-activatable analogue.

Based on the above-mentioned state of the art, the objective of the present invention is to provide a new class of photoactivatable fluorophores with improved properties. This objective is attained by the subject matter of the below presented claims.

SUMMARY OF THE INVENTION

Herein the inventors disclose that in silicon rhodamines the replacement of an aromatic ring by an alkyl chain makes it possible to obtain non-fluorescent, but photoactivatable olefinic silicon rhodamine derivatives with an exocyclic double bond. Photoactivation leads to the protonation of the double bond, which transforms the molecule into a cationic fluorescent molecule. Once photoactivated, the cation is in equilibrium with corresponding adducts, formed by inter- or intramolecular nucleophilic attack (e.g. by water resulting in hydroxylated derivatives), similarly to the equilibrium between the open and closed (=spiro-lactone) forms of the SiR fluorophore. Through chemical modifications or attachment to biomolecules the inventors were able to fine-tune equilibrium and kinetics of exchange between the cationic fluorescent and neutral non-fluorescent adducts.

TERMS AND DEFINITIONS

The term $C_1$-$C_4$ alkyl in the context of the present specification signifies a saturated linear or branched hydrocarbon having 1, 2, 3 or 4 carbon atoms, wherein in certain embodiments one carbon-carbon bond may be unsaturated and one $CH_2$ moiety may be exchanged for oxygen (ether bridge) or nitrogen (NH, or NR with R being methyl, ethyl, or propyl; amino bridge). Non-limiting examples for a $C_1$-$C_4$ alkyl are methyl, ethyl, propyl, prop-2-enyl, n-butyl, 2-methylpropyl, tert-butyl, but-3-enyl, prop-2-inyl and but-3-inyl. In certain embodiments, a $C_1$-$C_4$ alkyl is a methyl, ethyl, propyl or butyl moiety.

A $C_1$-$C_6$ alkyl in the context of the present specification signifies a saturated linear or branched hydrocarbon having 1, 2, 3, 4, 5 or 6 carbon atoms, wherein one carbon-carbon bond may be unsaturated and one $CH_2$ moiety may be exchanged for oxygen (ether bridge) or nitrogen (NH, or NR with R being methyl, ethyl, or propyl; amino bridge). Non-limiting examples for a $C_1$-$C_6$ alkyl include the examples given for $C_1$-$C_4$ alkyl above, and additionally 3-methylbut-2-enyl, 2-methylbut-3-enyl, 3-methylbut-3-enyl, n-pentyl, 2-methylbutyl, 3-methylbutyl, 1,1-dimethylpropyl, 1,2-dimethylpropyl, 1,2-dimethylpropyl, pent-4-inyl, 3-methyl-2-pentyl, and 4-methyl-2-pentyl. In certain embodiments, a $C_5$ alkyl is a pentyl or cyclopentyl moiety and a $C_6$ alkyl is a hexyl or cyclohexyl moiety.

The term unsubstituted $C_n$ alkyl when used herein in the narrowest sense relates to the moiety —$C_nH_{2n}$— if used as a bridge between moieties of the molecule, or —$C_nH_{2n+1}$ if used in the context of a terminal moiety. It may still contain fewer H atoms if a cyclical structure or one or more (non-aromatic) double bonds are present.

The term $C_n$ alkylene in the context of the present specification signifies a saturated linear or branched hydrocarbon comprising one or more double bonds. An unsubstituted alkylene consists of C and H only. A substituted alkylene may comprise one or several substituents as defined herein for substituted alkyl.

The term $C_n$ alkylyne in the context of the present specification signifies a saturated linear or branched hydrocarbon comprising one or more triple bonds and may also comprise one or more double bonds in addition to the triple bond(s). An unsubstituted alkylyne consists of C and H only. A substituted alkylyne may comprise one or several substituents as defined herein for substituted alkyl.

The terms unsubstituted $C_n$ alkyl and substituted $C_n$ alkyl include a linear alkyl comprising or being linked to a cyclical structure, for example a cyclopropane, cyclobutane, cyclopentane or cyclohexane moiety, unsubstituted or substituted depending on the annotation or the context of mention, having linear alkyl substitutions. The total number of carbon and—where appropriate—N, O or other hetero atoms in the linear chain or cyclical structure adds up to n.

Where used in the context of chemical formulae, the following abbreviations may be used: Me is methyl $CH_3$, Et is ethyl —$CH_2CH_3$, Prop is propyl —$(CH_2)_2CH_3$ (n-propyl, n-pr) or —$CH(CH_3)_2$ (iso-propyl, i-pr), but is butyl —$C_4H_9$, —$(CH_2)_3CH_3$, —$CHCH_3CH_2CH_3$, —$CH_2CH(CH_3)_2$ or —$C(CH_3)_3$.

The term substituted alkyl in its broadest sense refers to an alkyl as defined above in the broadest sense that is covalently linked to an atom that is not carbon or hydrogen, particularly to an atom selected from N, O, F, B, Si, P, S, Se, Cl, Br and I, which itself may be—if applicable—linked to one or several other atoms of this group, or to hydrogen, or to an unsaturated or saturated hydrocarbon (alkyl or aryl in their broadest sense). In a narrower sense, substituted alkyl refers to an alkyl as defined above in the broadest sense that is substituted in one or several carbon atoms by groups selected from amine $NH_2$, alkylamine NHR, imide NH, alkylimide NR, amino(carboxyalkyl) NHCOR or NRCOR, hydroxyl OH, oxyalkyl OR, oxy(carboxyalkyl) OCOR, carbonyl O and its ketal or acetal $(OR)_2$, nitril CN, isonitril NC, cyanate CNO, isocyanate NCO, thiocyanate CNS, isothiocyanate NCS, fluoride F, choride Cl, bromide Br, iodide I, phosphonate $PO_3H_2$, $PO_3R_2$, phosphate $OPO_3H_2$ and $OPO_3R_2$, sulfhydryl SH, suflalkyl SR, sulfoxide SOR, sulfonyl $SO_2R$, sulfanylamide $SO_2NHR$, sulfate $SO_3H$ and sulfate ester $SO_3R$, wherein the R substituent as used in the current paragraph, different from other uses assigned to R in the body of the specification, is itself an unsubstituted or substituted $C_1$ to $C_{12}$ alkyl in its broadest sense, and in a narrower sense, R is methyl, ethyl or propyl unless otherwise specified.

It is understood that mention of moieties $SO_3H$ or COOH or other acidic groups imply presence of the deprotonated form in the alternative, assuming appropriate conditions that allow dissociation.

The term amino substituted alkyl or hydroxyl substituted alkyl refers to an alkyl according to the above definition that is modified by one or several amine or hydroxyl groups $NH_2$, NHR, $NR_2$ or OH, wherein the R substituent as used in the current paragraph, different from other uses assigned to R in the body of the specification, is itself an unsubstituted or substituted $C_1$ to $C_{12}$ alkyl in its broadest sense, and in a narrower sense, R is methyl, ethyl or propyl unless otherwise specified. An alkyl having more than one carbon may comprise more than one amine or hydroxyl. Unless otherwise specified, the term "substituted alkyl" refers to alkyl in which each C is only substituted by at most one amine or hydroxyl group, in addition to bonds to the alkyl chain, terminal methyl, or hydrogen.

The term carboxyl substituted alkyl refers to an alkyl according to the above definition that is modified by one or several carboxyl groups COOH, or derivatives thereof, particularly carboxylamides $CONH_2$, CONHR and $CONR_2$, or carboxylic esters COOR, with R having the meaning as laid out in the preceding paragraph and different from other meanings assigned to R in the body of this specification.

Non-limiting examples of amino-substituted alkyl include —$CH_2NH_2$, —$CH_2NHMe$, —$CH_2NHEt$, —$CH_2CH_2NH_2$, —$CH_2CH_2NHMe$, —$CH_2CH_2NHEt$, —$(CH_2)_3NH_2$, —$(CH_2)_3NHMe$, —$(CH_2)_3NHEt$, —$CH_2CH(NH_2)CH_3$, —$CH_2CH(NHMe)CH_3$, —$CH_2CH(NHEt)CH_3$, —$(CH_2)_3CH_2NH_2$, —$(CH_2)_3CH_2NHMe$, —$(CH_2)_3CH_2NHEt$, —$CH(CH_2NH_2)CH_2CH_3$, —$CH(CH_2NHMe)CH_2CH_3$, —$CH(CH_2NHEt)CH_2CH_3$, —$CH_2CH(CH_2NH_2)CH_3$, —$CH_2CH(CH_2NHMe)CH_3$, —$CH_2CH(CH_2NHEOCH_3$, —$CH(NH_2)(CH_2)_2NH_2$, —$CH(NHMe)(CH_2)_2NHMe$, —$CH(NHEt)(CH_2)_2NHEt$, —$CH_2CH(NH_2)CH_2NH_2$, —$CH_2CH(NHMe)CH_2NHMe$, —$CH_2CH(NHEt)CH_2NHEt$, —$CH_2CH(NH_2)(CH_2)_2NH_2$, —$CH_2CH(NHMe)(CH_2)_2NHMe$, —$CH_2CH(NHEt)(CH_2)_2NHEt$, —$CH_2CH(CH_2NH_2)_2$, —$CH_2CH(CH_2NHMe)_2$ and —$CH_2CH(CH_2NHEt)_2$ for terminal moieties and —$CH_2CHNH_2$—, —$CH_2CHNHMe$-, —$CH_2CHNHEt$- for an amino substituted alkyl moiety bridging two other moieties.

Non-limiting examples of hydroxy-substituted alkyl include —$CH_2OH$, —$(CH_2)_2OH$, —$(CH_2)_3OH$, —$CH_2CH(OH)CH_3$, —$(CH_2)_4OH$, —$CH(CH_2OH)CH_2CH_3$, —$CH_2CH(CH_2OH)CH_3$, —$CH(OH)(CH_2)_2OH$, —$CH_2CH(OH)CH_2OH$, —$CH_2CH(OH)(CH_2)_2OH$ and —$CH_2CH(CH_2OH)_2$ for terminal moieties and —CHOH—, —$CH_2CHOH$—, —$CH_2CH(OH)CH_2$—, —$(CH_2)_2CHOHCH_2$—, —$CH(CH_2OH)CH_2CH_2$—, —$CH_2CH(CH_2OH)CH_2$—, —$CH(OH)(CH_2CHOH$—, —$CH_2CH(OH)CH_2OH$, —$CH_2CH(OH)(CH_2)_2OH$ and —$CH_2CHCH_2OHCHOH$— for a hydroxyl substituted alkyl moiety bridging two other moieties.

The term halogen-substituted alkyl refers to an alkyl according to the above definition that is modified by one or several halogen atoms selected (independently) from F, Cl, Br, I.

The term fluoro substituted alkyl refers to an alkyl according to the above definition that is modified by one or several fluoride groups F. Non-limiting examples of fluoro-substituted alkyl include —$CH_2F$, —$CHF_2$, —$CF_3$, —$(CH_2)_2F$, —$(CHF)_2H$, —$(CHF)_2F$, —$C_2F_5$, —$(CH_2)_3F$, —$(CHF)_3H$, —$(CHF)_3F$, —$C_3F_7$, —$(CH_2)_4F$, —$(CHF)_4H$, —$(CHF)_4F$ and —$C_4F_9$.

Non-limiting examples of hydroxyl- and fluoro-substituted alkyl include —$CHFCH_2OH$, —$CF_2CH_2OH$, —$(CHF)_2CH_2OH$, —$(CF_2)_2CH_2OH$, —$(CHF)_3CH_2OH$, —$(CF_2)_3CH_2OH$, —$(CH_2)_3OH$, —$CF_2CH(OH)CH_3$, —$CF_2CH(OH)CF_3$, —$CF(CH_2OH)CHFCH_3$, and —$CF(CH_2OH)CHFCF_3$.

The term aryl in the context of the present invention signifies a cyclic aromatic $C_5$-$C_{10}$ hydrocarbon that may comprise a heteroatom (e.g. N, O, S). Examples of aryl include, without being restricted to, phenyl and naphthyl, and any heteroaryl. A heteroaryl is an aryl that comprises one or several nitrogen, oxygen and/or sulphur atoms. Examples for heteroaryl include, without being restricted to, pyrrole, thiophene, furan, imidazole, pyrazole, thiazole, oxazole, pyridine, pyrimidine, thiazin, quinoline, benzofuran and indole. An aryl or a heteroaryl in the context of the invention additionally may be substituted by one or more alkyl groups.

An aryl methylene in the context of the present invention signifies a $CH_2$ (-methylene) group substituted by an aryl moiety. One non-limiting example of aryl methylene is a benzyl (Bn) group. If used in particular, a heteroaryl methylene in the context of the present invention signifies a $CH_2$ (-methylene) group substituted by a heteroaryl moiety.

A substituted aryl or heteroaryl or aryl methylene may comprise one or several substituents as defined herein for substituted alkyl.

"Capable of forming a hybrid" in the context of the present invention relates to sequences that under the conditions existing within the cytosol of a mammalian cell, are able to bind selectively to their target sequence. Such hybridizing sequences may be contiguously reverse-complimentary to the target sequence, or may comprise gaps, mismatches or additional non-matching nucleotides. The minimal length for a sequence to be capable of forming a hybrid depends on its composition, with C or G nucleotides contributing more to the energy of binding than A or T/U nucleotides, and the backbone chemistry.

"Nucleotides" in the context of the present invention are nucleic acid or nucleic acid analogue building blocks, oligomers of which are capable of forming selective hybrids with RNA oligomers on the basis of base pairing. The term nucleotides in this context includes the classic ribonucleotide building blocks adenosine, guanosine, uridine (and ribosylthymin), cytidine, the classic deoxyribonucleotides deoxyadenosine, deoxyguanosine, thymidine, deoxyuridine and deoxycytidine. It further includes analogues of nucleic acids such as phosphotioates, 2'O-methylphosphothioates, peptide nucleic acids (PNA; N-(2-aminoethyl)-glycine units linked by peptide linkage, with the nucleobase attached to the alpha-carbon of the glycine) or locked nucleic acids (LNA; 2'O, 4'C methylene bridged RNA building blocks). The hybridizing sequence may be composed of any of the above nucleotides, or mixtures thereof.

In the following, the molecules of the invention are discussed in detail. Where ionizable moieties are disclosed, it is understood that any salt, particularly any pharmaceutically acceptable salt of such molecule is encompassed by the invention. The salt comprises the ionized molecule of the invention and an oppositely charged counterion. Non-limiting examples of anionic salt forms include acetate, benzoate, besylate, bitatrate, bromide, carbonate, chloride, citrate, edetate, edisylate, embonate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate, phosphate, diphosphate, salicylate, disalicylate, stearate, succinate, sulfate, tartrate, tosylate, triethiodide and valerate. Non-limiting examples of cationic salt forms include aluminium, benzathine, calcium, ethylene diamine, lysine, magnesium, meglumine, potassium, procaine, sodium, tromethamine and zinc.

It is understood that any position wherein H is present can be substituted by D.

A first aspect of the invention relates to a compound characterized by general formula (100):

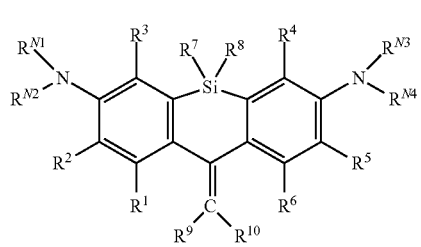

(100)

$R^1$ and $R^6$ are independently selected from hydrogen and fluorine. In certain embodiments, $R^1$ and $R^6$ are hydrogen.

$R^2$, $R^3$, $R^4$ and $R^5$ independently of each other can be any substituent. The skilled person is aware that these positions are highly variable in the art of rhodamine chemistry. If the molecule of the invention is to be connected to, for example, a tag or selective targeting moiety, these positions (in addition to one of $R^9$ and $R^{10}$) offer themselves to this function, as derivatization by an alkyl linker will not greatly affect optical properties.

In certain embodiments, $R^2$, $R^3$, $R^4$ and $R^5$ independently of each other are selected from H and a moiety having a molecular weight between 15 and 250 u (g/mol).

In certain embodiments, $R^2$, $R^3$, $R^4$ and $R^5$ independently of each other are selected from H, halogen, $SO_3H$, $CO_2H$, $NO_2$, $CO_2R$, $SO_2R$ (with R being selected from $C_1$ to $C_4$ unsubstituted alkyl) and an unsubstituted or substituted (particularly unsubstituted or halogen-, amino-, hydroxyl-, $SO_3H$— and/or carboxyl substituted) moiety selected from $C_1$-$C_{20}$ alkyl, $C_3$-$C_8$ cycloalkyl, $C_1$-$C_{20}$ alkoxy, $C_2$-$C_{20}$ alkenyl, $C_2$-$C_{20}$ alkynyl, $C_7$-$C_{20}$ alkylaryl, phenyl and 5- or 6-membered ring heteroaryl, or a combination thereof.

$R^7$ and $R^8$ are independently selected from unsubstituted and substituted, particularly amino-, hydroxy-, halogen-, $SO_3^-$— and/or carboxy-substituted, $C_1$-$C_{12}$ alkyl, $C_3$-$C_8$ cycloalkyl, $C_2$-$C_{12}$ alkylene, $C_2$-$C_{12}$ alkylyne and $C_7$-$C_{12}$ alkylaryl and unsubstituted or substituted 5 - or 6-ring aryl.

In certain embodiments, $R^7$ and $R^8$ are selected from an substituted, particularly amino-, hydroxy-, halogen-, $SO_3^-$— and/or carboxy-substituted, or unsubstituted alkyl, alkenyl, alkenyl, alkylary or aryl, and the total number of carbon atoms in both moieties does not exceed 12. In certain embodiments, this total carbon number does not exceed 10, 8 or even six.

In certain embodiments, $R^7$ and $R^8$ are the same and each comprises 1, 2, 3, 4, 5 or 6 carbon atoms. In certain embodiments, $R^7$ and $R^8$ are both methyl, ethyl, isopropyl, n-propyl, n-butyl, isobutyl or tert-butyl.

In certain embodiments, $R^7$ and $R^8$ are both phenyl or benzyl.

The N substituents $R^{N1}$, $R^{N2}$, $R^{N3}$ and $R^{N4}$ can be varied widely and allow tuning of the optical properties of the compound. The compound may also be attached to a tag or targeting moiety through these positions.

$R^{N1}$, $R^{N2}$, $R^{N3}$ and $R^{N4}$ may be independently selected from H, unsubstituted and substituted, particularly amino-, hydroxy-, halogen-, $SO_3^-$— and/or carboxy-substituted, $C_1$-$C_6$ alkyl, $C_3$-$C_8$ cycloalkyl, $C_1$-$C_4$ acyl (particularly acetyl), and $C_7$-$C_{12}$ alkylaryl (particularly methylene aryl, more particularly benzyl), and unsubstituted phenyl or phenyl substituted by COOH—, COOR, $CONR_2$, unsubstituted alkyl, halogen, O-alkyl, and/or $NO_2$.

Alternatively, $R^{N1}$ together with $R^{N2}$, and/or $R^{N3}$ together with $R^{N4}$ are a $C_3$, $C_4$, $C_6$ unsubstituted or substituted, particularly amino-, hydroxy-, halogen-, $SO_3^-$— and/or carboxy-substituted, alkyl forming a 3-7 sized ring structure. For illustration, if the two substituents on N together are a $C_3$ unsubstituted alkyl, the resulting structure is an azetidine (4-membered ring). The ring structure thus formed may comprise heteroatoms (to form a morpholine, for example), and may be substituted, particularly by short unsubstituted alkyl, (e.g. methyl).

Alternatively, $R^{N1}$ and/or $R^{N3}$ are independently selected from H and unsubstituted and substituted, particularly amino-, hydroxy-, halogen-, $SO_3^-$— and/or carboxy-substituted, $C_1$-$C_8$ alkyl, $C_3$-$C_8$ cycloalkyl, $C_1$-$C_4$ acyl, and $C_7$-$C_{12}$ alkylaryl, and $R^{N2}$ together with $R^2$ or $R^3$, and/or $R^{N4}$ together with $R^4$ or $R^5$, is an unsubstituted or substituted $C_2$, $C_3$ or $C_4$ alkyl, or an unsubstituted or substituted $C_2$, $C_3$ or $C_4$ N-, O-, S-, or Se-alkyl forming a ring structure. It is also possible that the N substituents form two ring structures with $R^2$ and $R^3$, to either of which ring structures the limitations given in this paragraph may apply. Such ring structures are well known in rhodamine chemistry.

In embodiments where only substituents of one N participate in ring, the other N's substituents are selected as laid out in previous paragraph.

One of $R^9$ and $R^{10}$ is hydrogen and the other one is hydrogen or a saturated carbon atom connected to any substituent. In certain embodiments, the moiety connected to the saturated carbon atom is selected from H and a moiety having a molecular weight between 15 and 250 u (g/mol). In certain embodiments, the moiety connected to the saturated carbon atom is selected from H, halogen, $SO_3H$, $CO_2H$, $NO_2$, $CO_2R$, $SO_2R$ (with R being selected from $C_1$ to $C_4$ unsubstituted alkyl) and an unsubstituted or substituted (particularly unsubstituted or halogen-, amino-, hydroxyl-, $SO_3H$— and/or carboxyl substituted) moiety selected from $C_1$-$C_{20}$ alkyl, $C_3$-$C_8$ cycloalkyl, $C_1$-$C_{20}$ alkoxy, $C_2$-$C_{20}$ alkenyl, $C_2$-$C_{20}$ alkynyl, $C_7$-$C_{20}$ alkylaryl, phenyl and 5- or 6-membered ring heteroaryl, or a combination thereof. In particular embodiments, the non-H moiety is an alkyl, alkenyl, or linker moiety connecting the fluorophore system to a binding moiety M.

In certain embodiments, $R^2$, $R^3$, $R^4$ and $R^5$ are independently selected from halogen, H, CN, OH, O(alkyl), O(aryl), SH, S(alkyl), S(aryl), amine, $NO_2$, CHO, COOH, C(O)$NR^{N5}_2$, COO(alkyl), COO(aryl), $PO_3H_2$, $SO_3H$, and $C_1$ to $C_4$ alkyl, alkyl being optionally substituted with one or more heteroatoms independently selected from N, O, and S, halogen, OH, O(alkyl), O(aryl), C(O)$NR^5_2$, SH, S(alkyl), S(aryl), amine, $NO_2$, CHO, $COO^-$, COOH, and with $R^{N5}$ selected from H and unsubstituted or amino-, hydroxyl-, carboxyl or fluoro substituted $C_1$ to $C_6$ alkyl, particularly $R^{N5}$ is selected from H and unsubstituted $C_1$ to $C_3$ alkyl.

In certain embodiments, the compound of the invention is covalently linked to a binding moiety M via any of the substituents $R^1$, $R^2$, $R^3$, $R^4$, $R^5$, $R^6$, $R^7$, $R^8$, $R^9$, $R^{10}$, $R^{N1}$, $R^{N2}$, $R^{N3}$ or $R^{N4}$.

In certain embodiments, the compound is covalently linked (particularly through any one of substituents $R^1$, $R^2$, $R^3$, $R^4$, $R^5$, $R^6$, $R^7$, $R^8$, $R^9$, $R^{10}$, $R^{N1}$, $R^{N2}$, $R^{N3}$ and $R^{N4}$) to a binding moiety M. M is a targeting or tagging moiety that allows the core dye compound to be selectively attached to biomolecules or certain target structures selected from:

M may be a moiety selectively attachable by covalent bond to a protein or nucleic acid under conditions prevailing in cell culture or inside of a living cell. In certain embodiments, M is a moiety able to form an ester bond, an ether bond, an amide bond, a disulfide bond, a Schiff base, or react in a click-chemistry reaction. In certain embodiments, M is selected from —COCH=$CH_2$, allowing Michael addition of SH groups present in proteins, —CO—NHS (N-hydroxysuccinimide), biotin, and an azide or ethyne moiety (click cycloaddition), tetrazine or BCN (bicyclo[6.1.0]nonyne), SCO (Cyclooctyne) or TCO (Transcyclooctene), maleimide to react with SH groups. The skilled artisan is aware of various alternatives of click chemistry partners that may alternatively be employed.

M may alternatively be a moiety a substrate of $O^6$-alkylguanine-DNA-alkyltransferase, particularly a 6-[(4-methylenephenyl)methoxy]-9H-purin-2-amine moiety of formula (110), or a pyrimidine derivative thereof, particularly a moiety of formula (111) or (112),

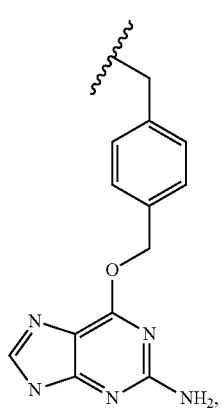
(110)

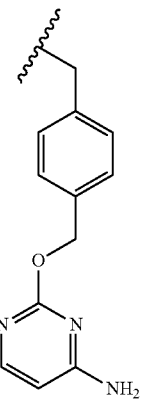
(111)

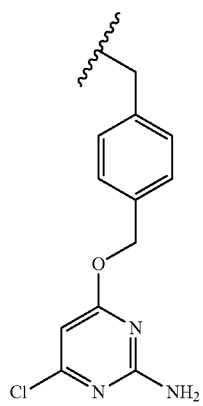
(112)

or a substrate of a haloalkane halotransferase, particularly a 1-chlorohexyl moiety as exemplarily shown below;

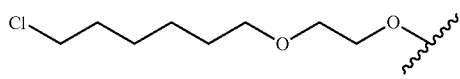 [SMILES: *OCCOCCCCCCCl]

M may also be a substrate of dihydrofolate reductase DHFR, particularly the moiety:

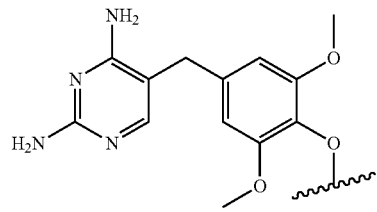 [SMILES: *Oc1c(OC)cc(Cc2cnc(N)nc2N)cc1OC]

If M is selected to function as a targeting moiety for biomolecules, a particularly advantageous approach is to covalently link the dye to a drug or drug-like small molecule with high specificity for a particular protein, nucleic acid or other complex biological structure. Thus, in certain embodiments, M is a moiety capable of selectively interacting non-covalently with a biomolecule (particularly a protein or nucleic acid) under inside of a live cell, wherein said moiety and said biomolecule form a complex having a dissociation constant $k_D$ of $10^{-6}$ mol/l or less. In certain such embodiments, M has a molecular mass of more than 160 u but less than 1000 u, particularly less than 700 u, more particularly less than 500 u, and M comprises up to five hydrogen bond donors (e.g., oxygen and or nitrogen atoms with one H attached), up to ten hydrogen bond acceptors (e.g., oxygen or nitrogen atoms) and is characterized by an octanol-water partition coefficient logP of below 5.6 (any of these characteristics applied to the isolated M moiety, without regard to the rest of compound). These are the so-called "Lipinski" rules of 5 (originally, referring to molecules between 160 and 500 u) for drug-like compounds. M can be any licensed medicinal or veterinary drug or a drug candidate for which affinity data for a particular biomolecule are known.

In certain particular embodiments, M is selected from taxol (see e.g. compound 56), jasplaklinolide (see e.g. compound 49), a bis-benzimide DNA stain (Hoechst dyes 33342, 33258, 34580; see compd 51), pepstatin A (specific staining of lysosomes), and triphenylphosphonium (specific staining of mitochondria).

In certain particular embodiments, M is an oligonucleotide having a sequence length of 10 to 40 nucleotides capable of sequence specifically forming a hybrid with a DNA or RNA sequence, particularly inside a human, animal, plant or bacterial cell.

In certain particular embodiments, M is a lipid. In certain embodiments, M is a lipid selected from a ceramide derivative, a glyceride, or a fatty acid.

In certain embodiments, any one of substituents $R^2$, $R^3$, $R^4$, $R^5$, and one of $R^9$ and $R^{10}$ independently of any other is H or a moiety having a molecular weight between 15 and 1500 u (g/mol) constituted of C, H, D, N, O, Si, P, S, Se F, Cl, Br, I atoms.

In certain particular embodiments, one of substituents $R^2$, $R^3$, $R^4$, $R^5$, $R^9$ and $R^{10}$ is a moiety having a molecular weight between 15 and 1500 u and the other ones are selected from H and unsubstituted or fluoro-, amino-, hydroxyl-, $SO_3H$— and/or carboxyl substituted $C_1$ to $C_4$ alkyl, alkenyl or alkynyl.

In certain particular embodiments, one of substituents $R^2$, $R^3$, $R^4$, $R^5$, $R^9$ and $R^{10}$ is a moiety having a molecular weight between 15 and 1500 u and the other ones are H.

In certain embodiments, the moiety having a molecular weight between 15 and 1500 u is characterized by a general formula —L-M, wherein L is a linker covalently connecting the compound of structure (1) to the binding moiety M as defined above, and L is a covalent bond or a linker consisting of 1 to 50 atoms having an atomic weight of 12 or higher (and H to fill valencies).

In general, the gist of the invention encompasses the attachment of a specific tagging or targeting moiety M to the central fluorophore, and the skilled artisan is aware that a very large number of alternatives exist to link the central fluorophore to M. In certain particular embodiments, the moiety having a molecular weight between 15 and 1500 u is characterized by a general formula

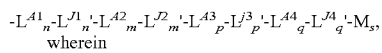

wherein $L^{A1}$, $L^{A2}$, $L^{A3}$ and $L^{A4}$ independently of each other are selected from $C_1$ to $C_{12}$ unsubstituted or amino-, hydroxyl-, carboxyl- or fluoro substituted alkyl or cycloalkyl, $(CH_2-CH_2-O)_r$ or $(CH_2-CH(OH)-CH_2-O)_r$ with r being an integer from 1 to 20, alkylaryl (e.g. benzyl), alkylaryl-alkyl (e.g. $CH_2$-phenyl-$CH_2$), and unsubstituted or alkyl-, halogen-, amino-, alkylamino-, imido-, nitro-, hydroxyl-oxyalkyl-, carbonyl-, carboxyl-, sulfuryl- and/or sulfoxyl substituted aryl or heteroaryl, $L^{J1}$, $L_{J2}$, $L^{J3}$ and $L^{J4}$ independently of each other are selected from $-NR^5C(O)-$, $-C(O)N(R^5)-$ (amide), $-CN-$, $-NC-$ (Schiff base), $-CO-$, $-OC(O)-$, $-C(O)O-$ (ester), $-NR^{N5}-$, $-O-$, $-P(OOH)-$, $-OP(OOH)-$, $-P(OOH)O-$, $-OP(OOH)O-$, $-OP(OOH)O-$, $-S-$, $-SO-$, $SO_2-$, with $R^{N5}$ selected from H and unsubstituted or amino-, hydroxyl-, carboxyl or fluoro substituted $C_1$ to $C_6$ alkyl, particularly $R^{N5}$ is selected from H and unsubstituted $C_1$ to $C_3$ alkyl;

n, n', m, m', p, p', q, q' and s independently from each other are selected from 0 and 1, and M has the meaning defined above.

In certain particular embodiments, L is $-L^{A1}-L^{J1}-L^{A2}{}_m-L^{J2}{}_m'-L^{A3}{}_p$, wherein $-L^{A1}$, $L^{A2}$ and $L^{A3}$ are independently selected from $C_1$ to $C_6$ unsubstituted, amino-, hydroxyl-, carboxyl- or fluoro substituted alkyl or cycloalkyl, and $(CH_2-CH_2-O)_r$ or $(CH_2-CH(OH)-CH_2-O)_r$ with r being an integer from 1 to 4, and $L^{J1}$ and $L^{J2}$ are selected independently from $-NR^5C(O)-$, $-C(O)N(R^5)-$, $-CN-$, $-NC-$, $-CO-$, $-OC(O)-$, $-C(O)O-$, $NR^{N5}-$, $-O-$, and $-S-$, and m, m' and p independently from each other are selected from 0 and 1.

In certain embodiments, $R^7$ and $R^8$ are independently selected from unsubstituted or hydroxyl-, amino- or halogen-substituted $C_1$ to $C_4$ alkyl, alkenyl or alkynyl, unsubstituted or hydroxyl-, amino- or halogen-substituted $C_3$ to $C_6$ cycloalkyl or unsubstituted or hydroxyl-, alkyoxy-, amino- or halogen-substituted phenyl.

In certain particular embodiments, $R^7$ and $R^8$ are methyl, ethyl, n-propyl, isopropyl, n-butyl, isobutyl, tert-butyl, or phenyl. In even more particular embodiments, $R^7$ and $R^8$ are the same.

In certain embodiments, the N substituents on one or both N are selected individually and do not form a ring structure. Herein, $R^{N1}$ and $R^{N2}$, and/or $R^{N3}$ and $R^{N4}$, are independently selected from H, unsubstituted and amino-, hydroxy-, carboxy- and/or fluoro-substituted $C_1$-$C_6$ alkyl, $C_1$-$C_4$ acyl, and $C_3$-$C_6$ cycloalkyl.

In certain particular embodiments, $R^{N1}$ and $R^{N2}$, and/or $R^{N3}$ and $R^{N4}$, are independently selected from H, methyl, ethyl, n-propyl, isopropyl, n-butyl, isobutyl, tert-butyl and $CH_2CF_3$.

In certain embodiments, the N substituents on one or both N are selected together as one linear chain to form a ring structure. Herein, $R^{N1}$ together with $R^{N2}$, and/or $R^{N3}$ together with $R^{N4}$ together are an unsubstituted or alkyl-, amino-, hydroxy-, carboxy- and/or fluoro-substituted $C_3$-$C_6$ alkyl, particularly $-(CH_2)_3-$, $-(CH_2)_4-$, $-(CH_2)_5-$, $-(CH_2)_2O(CH_2)_2-$ or $-(CH_2)_2NR^{NN}(CH_2)_2-$ with $R^{NN}$ being selected from H and unsubstituted $C_1$ to $C_4$ alkyl. In certain embodiments, one or several of the ring carbon atoms may be substituted by methyl.

In certain embodiments, the N substituents on one or both N are selected to form a ring structure bridging the N and positions $R^2/R^5$ and/or $R^3/R^4$ on the dibenzo[b,e]silin-10 (5H)-ylidene ring core.

If one ring connects N and $R^2/R^5$, $R^{N1}$ and/or $R^{N3}$ are independently selected from H, unsubstituted and alkyl- (particularly methyl-), amino-, hydroxy-, carboxy- and/or fluoro-substituted $C_1$-$C_6$ alkyl, $C_1$-$C_4$ acyl, and $C_3$-$C_6$ cycloalkyl, and $R^{N2}$ together with $R^2$ or $R^3$, and/or $R^{N4}$ together with $R^4$ or $R^5$, is an alkyl or heteroalkyl bridge selected from —(CH$_2$)$_2$—, —(CH$_2$)$_3$—, —CH$_2$CH=CH— or —(CH$_2$)$_4$— or —CH$_2$—O—, —CH$_2$—NR$^5$—, —CH$_2$—S—, —CH$_2$—Se—, —(CH$_2$)$_2$O—, —(CH$_2$)$_2$NR$^N$—, —(CH$_2$)$_2$S—, —(CH$_2$)$_2$Se—, —CH$_2$—O—CH$_2$—, —CH$_2$NR$^5$—, —CH$_2$S—CH$_2$—, —CH$_2$—Se—CH$_2$—, —CH$_2$-(1,2)phenyl-, and a mono- or dimethyl substituted derivative of any one of the foregoing alkyl or heteroalkyl bridge moieties. It is understood that when only one ring structure is formed between N and position $R^2/R^5$, the N not participating in the ring structure can be substituted by any of the options laid out above, namely independent or same alkyl or aryl, or one alkyl forming a four to seven membered ring.

In certain particular embodiments, $R^{N1}$ and/or $R^{N3}$ are independently selected from H, unsubstituted and alkyl- (particularly methyl-), amino-, hydroxy-, carboxy- and/or fluoro-substituted $C_1$-$C_6$ alkyl, $C_1$-$C_4$ acyl, and $C_3$-$C_6$ cycloalkyl, and $R^{N2}$ together with $R^2$, and/or $R^{N4}$ together with $R^5$, form an annular structure according to any one of substructures (101) to (104). Methods for introducing substructures as shown in (101) to (109) and (101') to (109') are disclosed in U.S. Pat. Nos. 6,191,278 and 6,130,101, incorporated herein by reference.

(101)

(101')

(102)

(102')

(103)

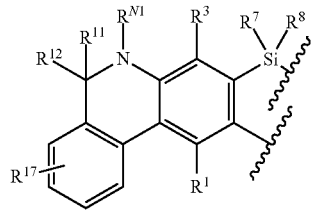

(103')

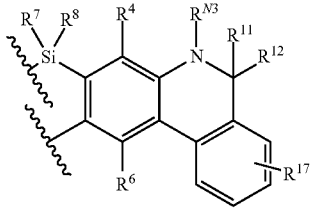

(104)

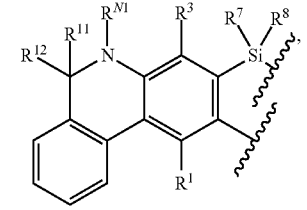

(104')

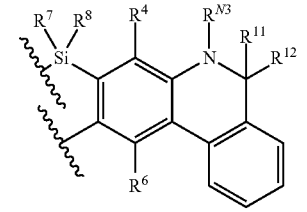

Herein, $R^{11}$, $R^{12}$, $R^{13}$, $R^{14}$, $R^{15}$ and $R^{16}$ are selected from H, unsubstituted or hydroxyl-, amino-, carboxyl-, sulfoxyl- or halogen-substituted $C_1$ to $C_4$ alkyl, halogen, SO$_3$R, COOR', CONR'$_2$ with R' selected from H and unsubstituted $C_1$ to $C_4$ alkyl; $R^{17}$—where applicable—is selected from H unsubstituted or hydroxyl-, amino-, carboxyl-, sulfoxyl- or halogen-substituted $C_1$ to $C_4$ alkyl, halogen, NO$_2$, CN, SO$_3$R, COOR', CONR'$_2$ with R' selected from H and unsubstituted $C_1$ to $C_4$ alkyl; and $R^1$, $R^3$, $R^7$ and $R^8$ can have any of the meanings given elsewhere herein.

In certain particular embodiments of structures (101) to (104), $R^{11}$, $R^{12}$, $R^{13}$, $R^{14}$, $R^{15}$ and $R^{16}$ are selected from H, methyl, CH$_2$—SO$_3$H, Cl and F.

Alternatively, $R^{N1}$ together with $R^3$, and $R^{N2}$ together with $R^2$, and/or $R^{N3}$ together with $R^4$, and $R^{N4}$ together with $R^5$, form a bi-annular structure according to any one of substructures (105) to (107) and/or (105') to (107'):

(105)

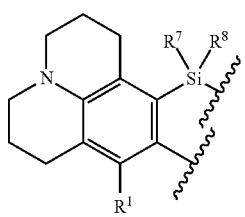

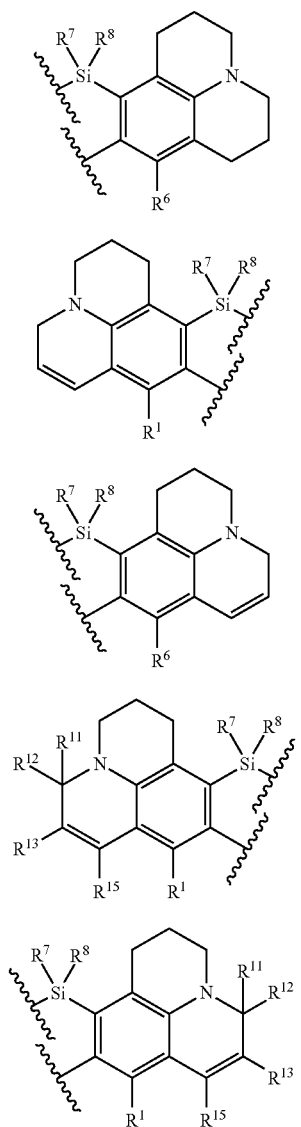

wherein R¹¹, R¹², R¹³, and R¹⁵ are selected from H, unsubstituted or hydroxyl-, amino-, carboxyl-, sulfoxyl- or halogen-substituted $C_1$ to $C_4$ alkyl, halogen, $SO_3R$, COOR', CONR'$_2$ with R selected from H and unsubstituted $C_1$ to $C_4$ alkyl; and R¹, R³, R⁷ and R⁸ can have any of the meanings given elsewhere herein.

In certain particular embodiments of structures (105) to (107), R¹¹, R¹², R¹³, and R¹⁵ are selected from H, methyl, $CH_2$—$SO_3H$, Cl and F.

Alternatively, $R^{N2}$ and/or $R^{N4}$ are independently selected from H, unsubstituted and alkyl-(particularly methyl-), amino-, hydroxy-, carboxy- and/or fluoro-substituted $C_1$-$C_6$ alkyl, $C_1$-$C_4$ acyl, and $C_3$-$C_6$ cycloalkyl, and $R^{N1}$ together with R³, and/or $R^{N3}$ together with R⁴, form an annular structure according to any one of substructures (108) to (109) and/or (108') to (109'):

wherein R¹, R³, R⁷ and R⁸ can have any of the meanings given herein.

In certain particular embodiments, the N substituents together form a four-membered ring (azetidine). Herein, $R^{N1}$ together with $R^{N2}$, and/or $R^{N3}$ together with $R^{N4}$ together are selected from —$(CH_2)_3$—, —$CH_2CHFCH_2$—, —$CH_2CF_2CH_2$—, —$CH_2CH(CH_3)CH_2$—, —$CH_2C(CH_3)_2CH_2$—, $CH_2CH(CN)CH_2$—, $CH_2CH(COOH)CH_2$—, $CH_2CH(CH_2COOH)CH_2$—, —$CH_2CH(OCH_3)CH_2$— and —$CH_2CH(N(CH_3)_2)CH_2$—. In certain more particular embodiments thereof, the substituent is the same for $R^{N1}$ with $R^{N2}$, and $R^{N3}$ with $R^{N4}$.

US2017045501, incorporated herein in by reference, discloses methods for making the above azetidine rings.

In certain particular embodiments, R¹, R⁶ and R⁹ are H.
In certain particular embodiments, R² and R⁵ are F or Cl.
In certain particular embodiments, R¹, R⁶ and R⁹ are H and R² and R⁵ are F or Cl.
In certain particular embodiments, R², R³, R⁴ and R⁵ are selected from H, halogen, $SO_3H$, and unsubstituted and amino-, hydroxy-, carboxy-, $SO_3H$—, and/or halogen-substituted $C_1$-$C_4$ alkyl, $CO_2H$, $CO_2R$, $SO_2R$ with R being selected from $C_1$ to $C_4$ unsubstituted alkyl.
In certain particular embodiments, R⁷ and R⁸ are independently selected from unsubstituted, or halogen-substituted $C_1$ to $C_4$ alkyl or $C_3$ to $C_6$ cycloalkyl and phenyl.
In certain particular embodiments, $R^{N1}$, $R^{N2}$, $R^{N3}$ and $R^{N4}$ are individually unsubstituted or amino-, hydroxyl- or halogen-substituted $C_1$ to $C_4$ alkyl or $C_3$ to $C_6$ cycloalkyl, or $R^{N1}$ together with $R^{N2}$, and $R^{N3}$ together with $R^{N4}$ together with the N form an unsubstituted or methyl-, ethyl- propyl-, or halogen-substituted aziridine, pyrrolidine, piperidine, piperazine or morpholine.

In certain particular embodiments, $R^{10}$ is selected from unsubstituted or amino-, hydroxyl-, carboxyl- and/or halogen-substituted $C_2$ to $C_{12}$ alkyl or $C_3$ to $C_7$ cycloalkyl.

In certain particular embodiments, $R^{10}$ is -$L^{A1}_n$-$L^{J1}_{n'}$-$L^{A2}_m$-$L^{J2}_{m'}$-$L^{A3}_p$-$L^{J3}_{p'}$-$L^{A4}_q$-$L^{J4}_{q'}$-$M_s$, wherein $L^{A1\ldots 4}$, $L^{J1\ldots 4}$, n, n' ... q', s and M have the definitions recited above.

Certain particular embodiments relate to the following selection of features, with all undefined features being selectable from other particular embodiments or general descriptions of the missing features:
$R^1$, $R^6$ and $R^9$ are H, and
$R^2$, $R^3$, $R^4$ and $R^5$ are selected from H, halogen, $SO_3H$, and unsubstituted and amino-, hydroxy-, $SO_3H$—, carboxy- and/or halogen-substituted $C_1$-$C_4$ alkyl, $CO_2H$, $CO_2R$, $SO_2R$ with R being selected from $C_1$ to $C_4$ unsubstituted alkyl.

Another particular combination is:
$R^1$, $R^6$ and $R^9$ are H, and
$R^7$ and $R^9$ are independently selected from unsubstituted or halogen-substituted $C_1$ to $C_4$ alkyl or $C_3$ to $C_6$ cycloalkyl and phenyl.

Another particular combination is:
$R^1$, $R^6$ and $R^9$ are H, and
$R^2$, $R^3$, $R^4$ and $R^5$ are selected from H, halogen, $SO_3H$, and unsubstituted and amino-, hydroxy-, $SO_3H$—, carboxy- and/or halogen-substituted $C_1$-$C_4$ alkyl, $CO_2H$, $CO_2R$, $SO_2R$ with R being selected from $C_1$ to $C_4$ unsubstituted alkyl, and
$R^7$ and $R^8$ are independently selected from unsubstituted or halogen-substituted $C_1$ to $C_4$ alkyl or $C_3$ to $C_6$ cycloalkyl and phenyl.

Another particular combination is:
$R^1$, $R^6$ and $R^9$ are H, and
$R^7$ and $R^9$ are independently selected from unsubstituted or halogen-substituted $C_1$ to $C_4$ alkyl or $C_3$ to $C_6$ cycloalkyl and phenyl, and
$R^{N1}$, $R^{N2}$, $R^{N3}$ and $R^{N4}$ are individually unsubstituted or amino-, hydroxyl- or halogen-substituted $C_1$ to $C_4$ alkyl or $C_3$ to $C_6$ cycloalkyl, or $R^{N1}$ together with $R^{N2}$, and $R^{N3}$ together with $R^{N4}$ together with the N form an unsubstituted or methyl-, ethyl- propyl-, or halogen-substituted aziridine, pyrrolidine, piperidine, piperazine or morpholine and/or Another particular combination is:
$R^1$, $R^6$ and $R^9$ are H, and
$R^2$, $R^3$, $R^4$ and $R^5$ are selected from H, halogen, $SO_3H$, and unsubstituted and amino-, hydroxy-, $SO_3H$—, carboxy- and/or halogen-substituted $C_1$-$C_4$ alkyl, $CO_2H$, $CO_2R$, $SO_2R$ with R being selected from $C_1$ to $C_4$ unsubstituted alkyl, and
$R^{N1}$, $R^{N2}$, $R^{N3}$ and $R^{N4}$ are individually unsubstituted or amino-, hydroxyl- or halogen-substituted $C_1$ to $C_4$ alkyl or $C_3$ to $C_6$ cycloalkyl, or $R^{N1}$ together with $R^{N2}$, and $R^{N3}$ together with $R^{N4}$ together with the N form an unsubstituted or methyl-, ethyl- propyl-, or halogen-substituted aziridine, pyrrolidine, piperidine, piperazine or morpholine.

Another particular combination is:
$R^1$, $R^6$ and $R^9$ are H, and/or
$R^2$, $R^3$, $R^4$ and $R^5$ are selected from H, halogen, $SO_3H$, and unsubstituted and amino-, hydroxy-, $SO_3H$—, carboxy- and/or halogen-substituted $C_1$-$C_4$ alkyl, $CO_2H$, $CO_2R$, $SO_2R$ with R being selected from $C_1$ to $C_4$ unsubstituted alkyl, and/or
$R^7$ and $R^8$ are independently selected from unsubstituted or halogen-substituted $C_1$ to $C_4$ alkyl or $C_3$ to $C_6$ cycloalkyl and phenyl, and/or
$R^{N1}$, $R^{N2}$, $R^{N3}$ and $R^{N4}$ are individually unsubstituted or amino-, hydroxyl- or halogen-substituted $C_1$ to $C_4$ alkyl or $C_3$ to $C_6$ cycloalkyl, or $R^{N1}$ together with $R^{N2}$, and $R^{N3}$ together with $R^{N4}$ together with the N form an unsubstituted or methyl-, ethyl- propyl-, or halogen-substituted aziridine, pyrrolidine, piperidine, piperazine or morpholine and/or
$R^{10}$ is selected from
unsubstituted or amino-, hydroxyl-, carboxyl- and/or halogen-substituted $C_2$ to $C_{12}$ alkyl or $C_3$ to $C_7$ cycloalkyl;
-$L^{A1}_n$-$L^{J1}_{n'}$-$L^{A2}_m$-$L^{J2}_{m'}$-$L^{A3}_p$-$L^{J3}_{p'}$-$L^{A4}_q$-$L^{J4}_{q'}$-$M_s$, wherein $L^{A1\ldots 4}$, $L^{J1\ldots 4}$, n, n' ... q', s and M have the definitions recited above.

Another particular combination is:
$R^1$, $R^2$, $R^3$, $R^4$, $R^5$, $R^6$ and $R^9$ are H,
$R^7$ and $R^8$ are $C_1$ to $C_4$ alkyl or phenyl,
$R^{N1}$, $R^{N2}$, $R^{N3}$ and $R^{N4}$ are individually unsubstituted or amino-, hydroxyl- or fluoro substituted $C_1$ to $C_4$ alkyl, or $R^{N1}$ together with $R^{N2}$, and $R^{N3}$ together with $R^{N4}$ together are —$(CH_2)_3$—, —$(CH_2)_4$—, —$(CH_2)_5$—, —$(CH_2)_2O(CH_2)_2$— or —$(CH_2)_2NH(CH_2)_2$— and
$R^{10}$ is selected from
unsubstituted or amino-, hydroxyl-, carboxyl- and/or fluoro substituted $C_2$ to $C_{12}$ alkyl or $C_3$ to $C_7$ cycloalkyl; or
$R^{10}$ is -$L^{A1}_n$-$L^{J1}_{n'}$-$L^{A2}_m$-$L^{J2}_{m'}$-$L^{A3}_p$-$L^{J3}_{p'}$-$L^{A4}_q$-$L^{J4}_{q'}$-$M_s$, wherein $L^{A1\ldots 4}$, $L^{J1\ldots 4}$, n, n' ... q', s and M have the definitions recited above.

The invention further encompasses the following compounds:
a. 4-(3,7-Bis(dimethylamino)-5,5-dimethyldibenzo[b,e]silin-10(5H)-ylidene)butanoic acid (2a);
b. 4-(3,7-Bis(dimethylamino)-5,5-dimethyldibenzo[b,e]silin-10(5H)-ylidene)-3-methylbutanoic acid (3a);
c. $N^3,N^3,N^7,N^7$,5,5-Hexamethyl-10-propylidene-5,10-dihydrodibenzo[b,e]siline-3,7-diamine (4a);
d. $N^3,N^3,N^7,N^7$,5,5-Hexamethyl-10-methylene-5,10-dihydrodibenzo[b,e]siline-3,7-diamine (5a);
e. 3-(3,7-Bis(dimethylamino)-5,5-dimethyldibenzo[b,e]silin-10(5H)-ylidene)propanoic acid (22);
f. 4-(3,7-Bis(dimethylamino)-5,5-dimethyldibenzo[b,e]silin-10(5H)-ylidene)-2,2-dimethylbutanoic acid (28);
g. 4-(3,7-Bis(dimethylamino)-5,5-diisopropyldibenzo[b,e]silin-10(5H)-ylidene)butanoic acid (6a);
h. 4-(3,7-Bis(dimethylamino)-2,8-difluoro-5,5-dimethyldibenzo[b,e]silin-10(5H)-ylidene)butanoic acid (36)
i. 3-(3,7-Di(azetidin-1-yl)-5,5-dimethyldibenzo[b,e]silin-10(5H)-ylidene)propanoic acid (42);
j. 4-(3,7-Bis(dimethylamino)-5,5-dimethyldibenzo[b,e]silin-10(5H)-ylidene)-N-(2-(2-((6-chlorohexyl)oxy)ethoxy)ethyl)butanamide (44);
k. 2,5-Dioxopyrrolidin-1-yl-4-(3,7-bis(dimethylamino)-5,5-dimethyldibenzo[b,e]silin-10(5H)-ylidene)butanoate (45);
l. N-(4-(((2-Amino-9H-purin-6-yl)oxy)methyl)benzyl)-4-(3,7-bis(dimethylamino)-5,5-dimethyldibenzo[b,e]silin-10(5H)-ylidene)butanamide (47);
m. N-(4-((4R,7R,10S,13S,19S,E)-7-((1 H-Indol-2-yl)methyl)-4-(4-hydroxyphenyl)-8,13,15,19-tetramethyl-2,6,9,12-tetraoxo-1-oxa-5,8,11-triazacyclononadec-15-en-10-yl)butyl)-4-(3,7-bis(dimethylamino)-5,5-dimethyldibenzo[b,e]silin-10(5H)-ylidene)butanamide (49);

n. 4-(3,7-Bis(dimethylamino)-5,5-dimethyldibenzo[b,e]silin-10(5H)-ylidene)-N-(4-(4-(6-(4-methylpiperazin-1-yl)-1H,3'H-[2,5'-bibenzo[d]imidazol]-2'-yl)phenoxy)butyl)butanamide (51);

o. (2αR,4S,4αS,6R,9S,11S,12S,12αR,12βS)-12β-Acetoxy-9-((3-(4-(3,7-bis(dimethylamino)-5,5-dimethyldibenzo[b,e]silin-10(5H)-ylidene)butanamido)-2-hydroxy-3-phenylpropanoyl)oxy)-4,6,11-trihydroxy-4α,8,13,13-tetramethyl-5-oxo-2α,3,4,4α,5,6,9,10,11,12,12α,12β-dodecahydro-1H-7,11-methanocyclodeca[3,4]benzo[1,2-β]oxet-12-yl benzoate (53);

p. 8-(4-(3,7-Bis(dimethylamino)-5,5-dimethyldibenzo[b,e]silin-10(5H)-ylidene)butanamido)octanoic acid (55);

q. (2αR,4S,4αS,6R,9S,11S,12S,12αR,12βS)-12β-Acetoxy-9-((3-(8-(4-(3,7- bis(dimethylamino)-5,5-dimethyldibenzo[b,e]silin-10(5H)-ylidene)butanamido)octanamido)-2-hydroxy-3-phenylpropanoyl)oxy)-4,6,11-trihydroxy-4α,8,13,13-tetramethyl-5-oxo-2α,3,4,4α,5,6,9,10,11,12,12α,12β-dodecahydro-1H-7,11-methanocyclodeca[3,4]benzo[1,2-β]oxet-12-yl benzoate (56);

r. 4-(3,7-Bis(dimethylamino)-5,5-dimethyldibenzo[b,e]silin-10(5H)-ylidene)-N-(4-(6-methyl-1,2,4,5-tetrazin-3-yl)benzyl)butanamide (58);

s. 4-(3,7-Bis(dimethylamino)-5,5-diisopropyldibenzo[b,e]silin-10(5H)-ylidene)-N-(2-(2-((6-chlorohexyl)oxy)ethoxy)ethyl)butanamide (59);

t. 4-(3,7-Bis(dimethylamino)-5,5-diisopropyldibenzo[b,e]silin-10(5H)-ylidene)-N-(21-chloro-8-oxo-3,6,12,15-tetraoxa-9-azahenicosyl)butanamide (64);

u. 1-(4-(3,7-Bis(dimethylamino)-5,5-diisopropyldibenzo[b,e]silin-10(5H)-ylidene)butanamido)-N-(2-(2-((6-chlorohexyl)oxy)ethoxy)ethyl)-3,6,9,12-tetraoxapentadecan-15-amide (65);

v. N-(4-(((2-Amino-9H-purin-6-yl)oxy)methyl)benzyl)-4-(3,7-bis(dimethylamino)-5,5-diisopropyldibenzo[b,e]silin-10(5H)-ylidene)butanamide (66);

w. 3-((4-(((2-Amino-9H-purin-6-yl)oxy)methyl)benzyl)amino)-2-(4-(3,7-bis(dimethylamino)-5,5-diisopropyldibenzo[b,e]silin-10(5H)-ylidene)butanamido)-3-oxopropane-1-sulfonic acid (69);

x. N-(4-((4R,7R,10S,13S,19S,E)-7-((1H-Indol-2-yl)methyl)-4-(4-hydroxyphenyl)-8,13,15,19-tetramethyl-2,6,9,12-tetraoxo-1-oxa-5,8,11-triazacyclononadec-15-en-10-yl)butyl)-4-(3,7-bis(dimethylamino)-5,5-diisopropyldibenzo[b,e]silin-10(5H)-ylidene)butanamide (70);

y. N-(4-(((2-Amino-9H-purin-6-yl)oxy)methyl)benzyl)-4-(3,7-bis(dimethylamino)-2,8-difluoro-5,5-dimethyldibenzo[b,e]silin-10(5H)-ylidene)butanamide (71);

z. N-(4-((4R,7R,10S,13S,19S,E)-7-((1H-Indo-2-yl)methyl)-4-(4-hydroxyphenyl)-8,13,15,19-tetramethyl-2,6,9,12-tetraoxo-1-oxa-5,8,11-triazacyclononadec-15-en-10-yl)butyl)-4-(3,7-bis(dimethylamino)-2,8-difluoro-5,5-dimethyldibenzo[b,e]silin-10(5H)-ylidene)butanamide (72).

Another aspect of the invention relates to the use of a compound according to any one of the preceding aspects and embodiments of the invention in a method of staining a biological sample.

Further, a method to stain a sample is encompassed by the invention, wherein the method comprising the steps of:

a. contacting the sample with a compound according to any one of the preceding aspects, b. illuminating the sample with light of a wavelength ranging from 280 to 450 nm, particularly in the range of 280-405 nm.

c. recording the presence and location of said compound in said sample by illuminating the sample with an appropriate excitation wavelength λ, particularly a λ close to the maximum of the excitation spectrum of 646 nm;

d. and recording light emitted from said sample at an appropriate emission wavelength λ, particularly a λ close to the maximum of the emission spectrum of 668 nm.

In order to avoid activation of the fluorophore prior to the measurement, illumination of the dye or the sample containing the dye compound of the invention with light of the photoactivating wavelength must be avoided.

Wherever alternatives for single separable features such as, for example, $R^1$, $R^2$, $R^{N1}$ or $R^{10}$ are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

EXAMPLES

Example 1

General Description of All Species Involved in this Study

Photoactivatable silicon rhodamines were synthesised in three steps from commercially available starting materials in analogy to a previously published synthesis (Grimm et al., ACS Cent. Sci. 2017, 3, 975-985).

Figure 1:
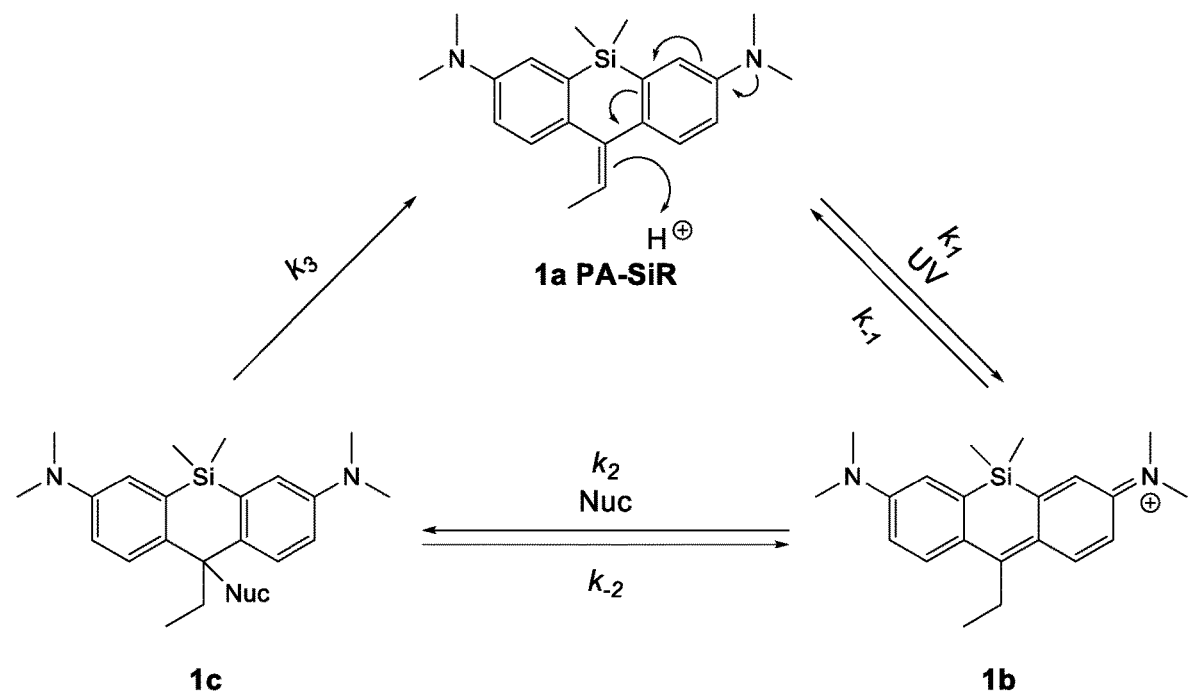
FIG. 1 shows (A) structures of PA-SiR 1a, the fluorescent cation 1b and the non-fluorescent compound 1c. (B) Top UV-Vis spectra of PA-SiR 2a (20 μm in PBS) before and after activation by UV irradiation (2 min). The spectra of the activated solution were measured every 1 min. Bottom Change of absorbance after activation at four different wavelengths over time. (C) Excitation and emission spectrum of the cation 2b.
Figure 1B:
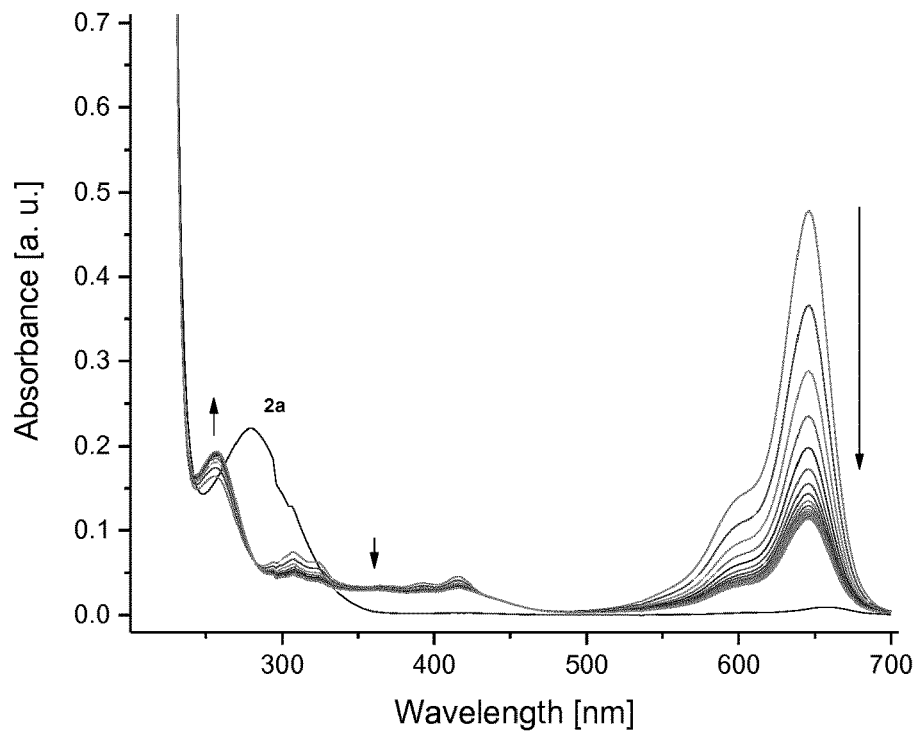
Figure 1B:
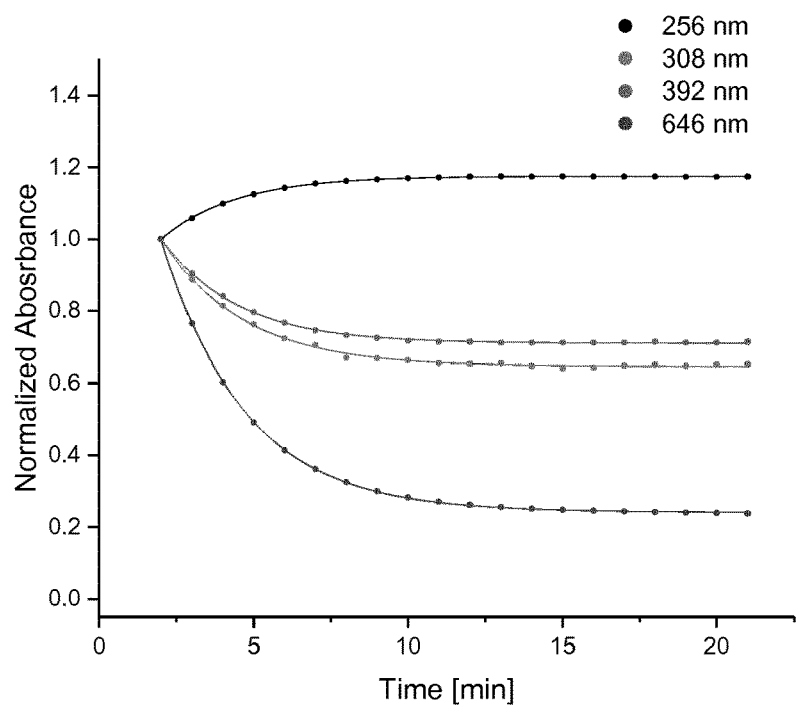
Figure 1:
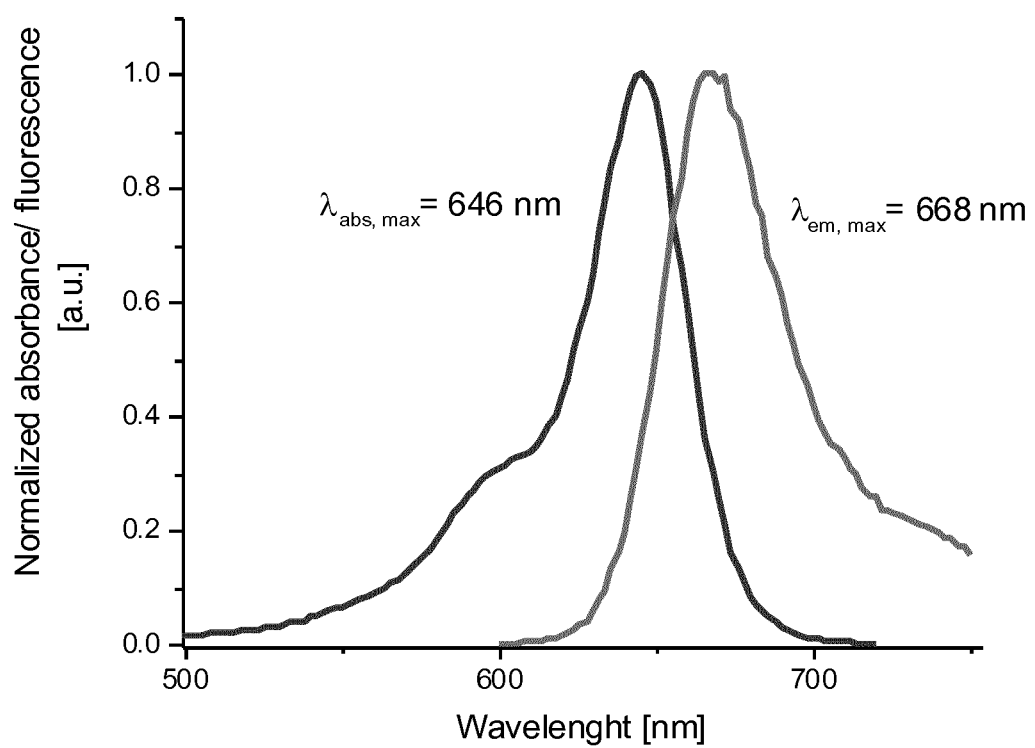

Upon UV irradiation of an aqueous solution of PA-SiR 2a, the fluorescent and blue-coloured cation 2b is forming (FIG. 1A), as confirmed by LC-MS. Compound 2b has an excitation maximum at 646 nm and an emission maximum at 668 nm. The extinction coefficient is 25,000 $M^{-1}cm^{-1}$ (in PBS at pH 7.3) and the quantum yield in aqueous solution was measured to be 0.37, whereas 2a shows only absorbance in the UV-range (FIGS. 1B and C and Table 1). However, the blue solution of 2b undergoes discoloration over time (FIG.

1C). It was shown by $^1$H NMR that the discoloration observed by UV-Vis spectroscopy, which takes place on a time scale of roughly 10 min, could be assigned to the formation of a new species. The new species corresponds to the hydroxylated form 2c (LC-MS) as the fluorescent cation 2b is attacked by nucleophiles at the electrophilic central carbon. Thus, 2b is in equilibrium with the hydroxylated form 2c in aqeous solution, which leads to the discoloration of the blue solution within 10 min. The thermodynamics and kinetics of these reactions are discussed in more detail below.

Example 2

Fine-Tuning of the Equilibria Between Fluorescent Cation and the Non-Fluorescent Compounds In order to study the kinetic properties of the second equilibrium (FIG. 1A, $k_2$ and $k_{-2}$), UV-Vis spectroscopy was used. In order to achieve the highest possible time resolution, the photoactivation was carried out in the spectrometer. These measurements revealed a dependence of the photoactivation and the second equilibrium between 1b and 1c (both kinetics and thermodynamics) on pH and solvent polarity (FIG. 2B). Effects such as solubility, pH, nucleophilicity and electrophilicity of the involved species play an important role.

Figure 2A:
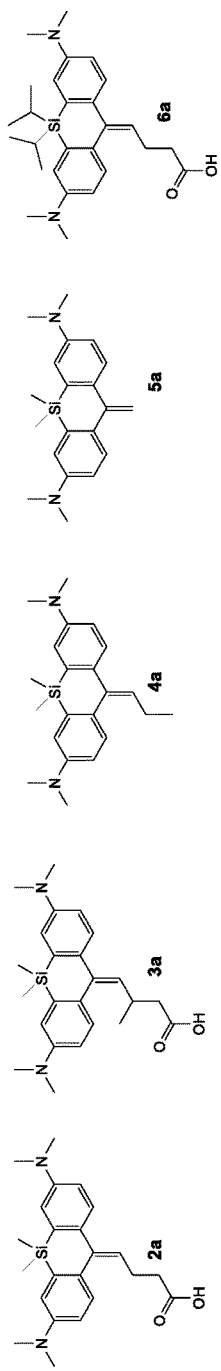
FIG. 2 shows (A) structures of the measured PA-SiR's. (B) Decay of absorbance at 646 nm normalized to the initial value reached after photoactivation of each compound. Compounds were dissolved in PBS/ACN (10 μM, 7:3, F) except 2a in PBS pH=7.3, 11.1 or 3.1, where the pH was adjusted by addition of HCl and NaOH. (C) Different PA-SiR probes together with the measurement on their respective protein-tag (10 μM PBS, M).
Figure 2B:
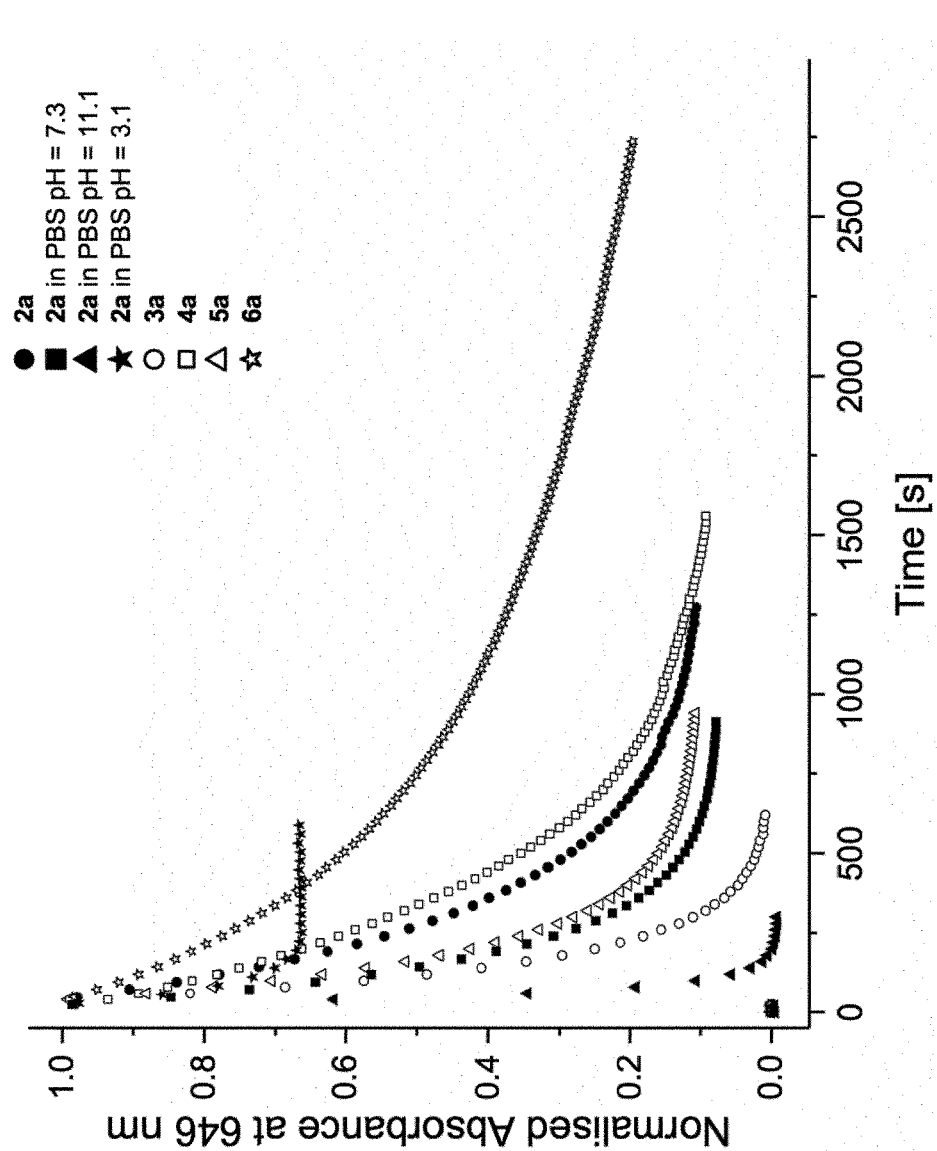

Moreover, similar UV-Vis analysis of several analogues illustrated the influence on this equilibrium of different substituents at various positions (FIG. 2). It was shown that the ratio of the fluorescent cation 1b to hydroxylated compound 1c could be tuned in both directions in comparison to the standard compound 2a by structural changes at the periphery.

Figure 2C:
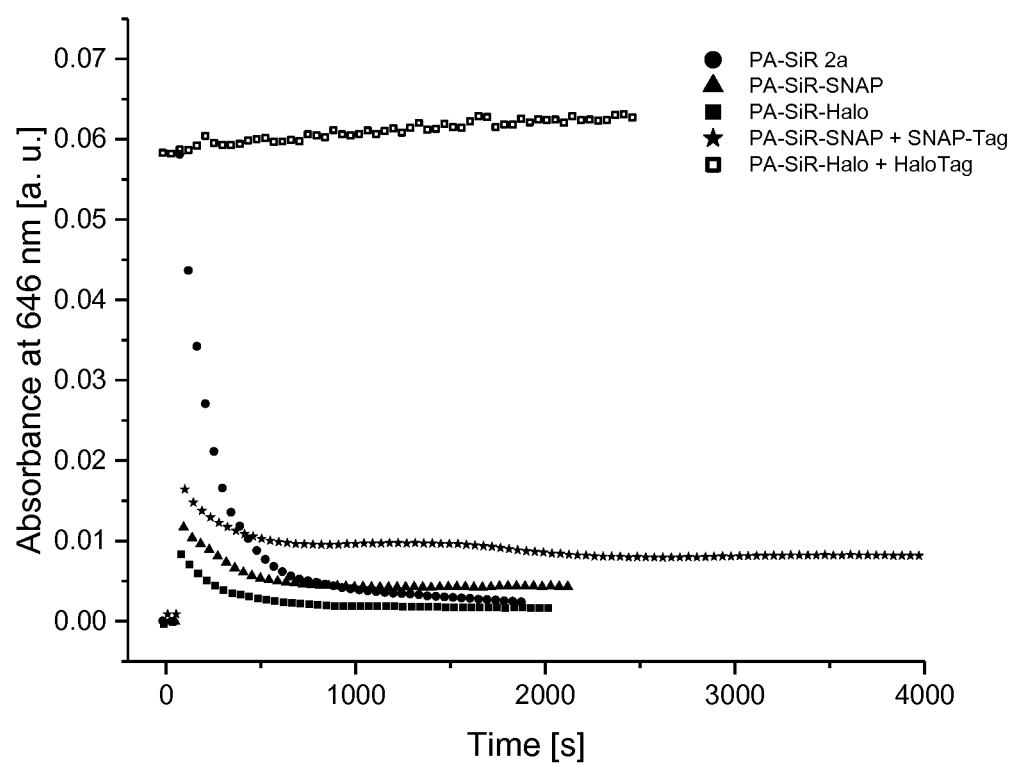

Since both the kinetic properties and the equilibrium of the second step could be tuned by chemical modifications and changes in solvent, the inventors hypothesised that also the microenvironment of protein surfaces can influence the stability of the fluorescent cation 1 b. Therefore, SNAP-tag and HaloTag substrates were synthesised and reacted with their respective protein tags. It could be shown that the same fluorophore showed different behaviour on the two protein-tags (FIG. 2C). A stable signal was achieved on the surface of HaloTag. In contrast, with SNAP-tag a fast decay was seen. The difference in decay rates permits to distinguish different molecular species such as SNAP and HaloTag labelled with the same PA-SiR. The decay rate also reports on the environment of the activated fluorophore.

Figure 3:
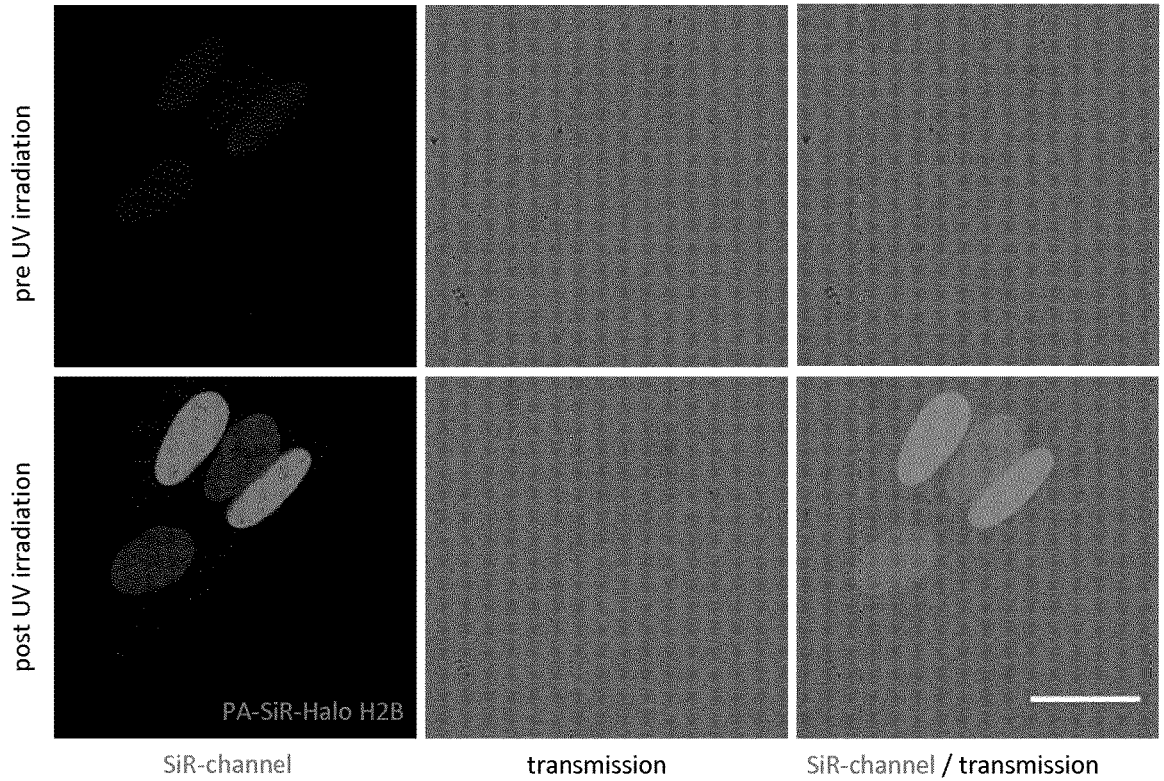
FIG. 3 U2OS cells expressing HaloTag-H2B fusion stained with PA-SiR-Halo for 1 h (1 μM) and washed once for 3 min. Images were taken before and after irradiation with the 355 nm laser on a confocal microscope. Scale bar 30 μm.

Motivated by the versatility of the compounds the inventors synthesised corresponding probes from PA-SIR and various ligands (PA-SiR-Halo, PA-SiR-SNAP, PA-SiR-Actin, PA-SiR-DNA, PA-SiR-Tubulin) and tested them for applications in live-cell imaging. The olefinic structure is not charged and therefore ideal to pass the plasma membrane. The compounds showed good cell-permeability and could be activated efficiently in live cells in both widefield (DAPI channel) and confocal microscopy (355 nm laser). PA-SiR-SNAP and PA-SiR-Halo probes were successfully localised in Hela cells expressing either SNAP-tag or HaloTag in the nucleus. PA-SiR-Halo was also successfully localised to H2B (FIG. 3). PA-SiR-Actin, PA-SiR-DNA and PA-SiR-Tubulin were localised to their targets.

Example 3

General Procedure A for the Silane Introduction

3-Bromo-N,N-dimethylaniline (13) (3.20 g, 16.00 mmol, 2.0 eq.) was dissolved in dry $Et_2O$ (45 mL) and cooled down to −78° C. sec-BuLi (14.0 mL, 18.40 mmol, 2.3 eq., 1.3 M in cyclohexane) was added dropwise over 15 min and the mixture was stirred for 30 min at −78° C. Dichlorodimethylsilane (14) (1.0 mL, 8.00 mmol, 1.0 eq.) was added dropwise over 10 min at −78° C. The mixture was stirred for 10 min at −78° C. and then warmed up to room temperature and stirred for 1 h. The mixture was quenched with aqueous saturated $NaHCO_3$ solution. The aqueous layer was extracted with $Et_2O$ (3×150 mL) and the combined organic layers were dried over $MgSO_4$, filtered and evaporated to afford the crude product.

Example 4

General Procedure B for the Bromination

A solution of 15 (1.85 g, 6.18 mmol, 1.0 eq.) and ammonium acetate (95 mg, 1.24 mmol, 0.2 eq.) in ACN (30 mL) was cooled down to 0° C. NBS (2.3 g, 12.98 mmol, 2.1 eq.) was added portion wise over 10 min. The mixture was stirred at 0° C. for 30 min and then warmed up to room temperature and stirred for 2 h. A mixture of aqueous saturated $NaHCO_3$ solution and water 1:1 was added. The aqueous layer was extracted with $CH_2Cl_2$ (3×100 mL) and the combined organic layers were dried over $MgSO_4$, filtered and evaporated to afford the crude product.

Example 5

General Procedure C for the Ring Closure

A solution of 16 (365 mg, 0.8 mmol, 1.0 eq.) in dry THF (8 mL) was cooled down to −78° C. sec-BuLi (1.4 mL, 1.76 mmol, 2.2 eq., 1.3 M in cyclohexane) was added dropwise over 5 min and the mixture was stirred for 30 min at −78° C. A solution of glutaric anhydride (17) (100 mg, 0.88 mmol, 1.1 eq.) in dry THF (1.0 mL) was added to the mixture. The mixture was stirred at −78° C. for 15 min and then warmed up to room temperature and stirred for 30 min. Acetic acid (2 mL) was added to the mixture. The blue mixture was adsorbed on $SiO_2$ (2 g).

Example 6

Materials and Methods

All chemical reagents and anhydrous solvents for synthesis were purchased from commercial suppliers (Acros, Apollo, Armar, Bachchem, Biomatrik, Fluka, Fluorochem, LC Laboratories, Merck, Reseachem, Roth, Sigma-Aldrich and TCI) and used without further purification. BG-NH$_2$ 48 and Halo-NHBoc 43 were available in the Johnsson group. Jasplakinolide-NHBoc 48 was obtained from a custom synthesis. Composition of mixed solvents is given by volume ratio (v/v). Reactions in the absence of air and moisture were performed in oven-dried glassware under Ar or N2 atmosphere. Flash column chromatography was performed using a CombiFlash Rf system (Teledyne ISCO) using $SiO_2$ RediSep® Rf columns at 25° C. The used solvent compositions are reported individually in parentheses. Analytical thin layer chromatography was performed on glass plates coated with silica gel 60 F254 (Merck). Visualisation was achieved using UV light (254 nm). Evaporation in vacuo was performed at 25-60° C. and 900-10 mbar. $^1$H, $^{13}$C, and $^{19}$F NMR spectra were recorded on AV 400 and AV 600 Bruker spectrometers at 400 MHz or 600 MHz ($^1$H), 101 MHz or 151 MHz ($^{13}$C), 377 MHz or 566 MHz ($^{19}$F)

respectively. All spectra were recorded at 298 K. Chemical shifts δ are reported in ppm downfield from tetramethylsilane using the residual deuterated solvent signals as an internal reference (CDCl$_3$: $\delta_H$=7.26 ppm, $\delta_C$=77.16 ppm; CD$_3$OD: $\delta_H$=3.31 ppm, $\delta_C$=49.00 ppm; DMSO-d$_6$: $\delta_H$=2.50 ppm, $\delta_C$=39.52 ppm; ACN-d$_3$: $\delta_H$=1.94 ppm, $\delta_C$=118.26 ppm). For $^1$H, $^{13}$C and $^{19}$F NMR, coupling constants J are given in Hz and the resonance multiplicity is described as s (singlet), d (doublet), t (triplet), q (quartet), quint (quintet), sext (sextet), sept (septet), m (multiplet) and br. (broad). High-resolution mass spectrometry (HRMS) was performed by the MS-service of the EPF Lausanne (SSMI) on a Waters Xevo® G2-S Q-Tof spectrometer with electron spray ionisation (ESI). Liquid chromatography coupled to mass spectrometry (LC-MS) was performed on a Shimadzu MS2020 connected to a Nexera UHPLC system equipped with a Waters ACQUITY UPLC BEH C18 (1.7 µm, 2.1×50 mm) column. Buffer A: 0.05% HCOOH in H$_2$O Buffer B: 0.05% HCOOH in ACN. Analytical gradient was from 10% to 90% B within 6 min with 0.5 mL/min flow unless otherwise stated. Preparative reverse phase high-performance liquid chromatography (RP-HPLC) was carried out on a Dionex system equipped with an UltiMate 3000 diode array detector for product visualisation on a Waters Symmetry C18 column (5 µm, 3.9×150 mm) or on a Waters SunFire™ Prep C18 OBD™ (5 µm, 10×150 mm) column. Buffer A: 0.1% TFA in H$_2$O Buffer B: ACN. Typical gradient was from 10% to 90% B within 32 min with 3 or 4 mL/min flow.

Example 7

In Vitro Characterization and Microscopy

General Considerations

Three different UV light sources were used in the following experiments: a transilluminator (Biometra TI 1, 312 nm, high), a photography flash (Agfatronic 261B, plastic cover removed), a monochromator (Polychrome V, FEI, at 330 nm for 12 s) abbreviated as T, F and M. PBS (6.7 mm, Lonza) was used in all experiments.

$^1$H NMR Analysis

PA-SiR 2a (1 mg, 2.5 µmol) was dissolved in PBS/D$_2$O (1 mL, 90:10) and NaOH (1 µL, 5 M) was added to achieve better solubility as PA-SiR 2a was isolated as its TFA salt (pH=7-8, pH paper). $^1$H NMR spectra were measured on a Bruker AV 600 spectrometer at 600 MHz and 298 K. Chemical shifts δ are reported in ppm downfield from tetramethylsilane using the DMSO signal ($\delta_H$=2.50 ppm) instead of the residual deuterated solvent signal as an internal reference. Spectra were measured with either NS=128 using a water suppression pre-saturation sequence. UV irradiation was performed outside of the spectrometer for the indicated times (T). After each irradiation step the NMR sample was transferred to the NMR spectrometer.

LC-MS Analysis

PA-SiR 2a was dissolved in water (50 µM). UV irradiation was performed in a quartz cuvette (Hellma Analytics) for the indicated times (T). Aliquots were taken to measure LC-MS at defined time points using an analytical gradient from 10% to 100% B within 6 min with 0.5 mL/min flow.

Fluorescence Measurements and Determination of Quantum Yield

Fluorescence spectra were measured on an Infinite M1000 (Tecan) plate reader. Quantum yields were determined using a Quantaurus QY (Hamamatsu).

UV-Vis Analysis

PA-SiRs were prepared as stock solutions in dry DMSO and diluted in PBS or PBS/ACN such that the final concentration of DMSO did not exceed 5% v/v. PBS solutions of different pH were adjusted by addition of HCl or NaOH solution using a pH meter.

Full Absorbance Spectra Measurements of PA-SiR 2a

Solutions were prepared in PBS (10 µm or 20 µM) at the indicated pH. UV irradiation was performed outside of the spectrometer for the indicated period (T). Absorbance spectra were recorded using a SHIMADZU UV spectrophotometer (UV-1800) and 1 cm fluorescence quartz cuvettes (Hellma Analytics). Spectra were recorded every minute.

pH Dependence of PA-SiR 2a

Solutions of 2a in PBS (10 µM) at the desired pH were prepared in 1 cm fluorescence quartz cuvette (Hellma Analytics). UV irradiation was performed directly inside the spectrophotometer during the running experiment at a fixed distance (F, single flash). Kinetic absorbance measurements were recorded on a Perkin-Elmer Lambda 950 spectrophotometer at 646 nm.

UV-Vis Analysis of Various PA-SiRs

Solutions were prepared in PBS/ACN (10 µM, 7:3) in 1 cm fluorescence quartz cuvettes (Hellma Analytics). UV irradiation was performed directly inside the spectrophotometer during the running experiment at a fixed distance (F, single flash). Kinetic absorbance measurements were recorded on a Perkin-Elmer Lambda 950 spectrophotometer at 646 nm.

UV-Vis Analysis of PA-SiR-Halo and PA-SiR-SNAP

SNAP-tag protein and HaloTag protein were available in the Johnsson lab as 5.3 and 3.6 mM solutions in HEPES-Glycerol (1:1). PA-SiR-Halo and PA-SiR-SNAP were dissolved in PBS (10 µM) and protein (20 µM, 2.0 equiv.) was added. The mixture was incubated for 1 h (HaloTag) or 2 h (SNAP-tag) before UV-Vis measurement. UV irradiation was performed directly inside the spectrophotometer during the running experiment at a fixed distance (M, 12 s). Kinetic absorbance measurements were recorded on a Jasco V770 spectrophotometer equipped with a Peltier cooling element (PAC743R) at 646 nm.

Plasmids

Mammalian expression vectors with a SNAP-tag-NLS or SNAP-tag-Halo-tag-NLS fusion construct were available in the Johnsson lab. H2B-Halo was constructed from a pEBTet plasmid and the commercially available pCLIPf-H2B plasmid (NEB).

Cell Culture and Transfection

HeLa or U2OS cells were cultured in high-glucose DMEM media with GlutaMAX-1 (Life Technologies) supplemented with 10% FBS (Life Technologies) in a humidified 5% CO$_2$ incubator at 37° C. Cells were split every 3-4 days or at confluency.

Cells were seeded on glass bottom 35 mm dishes (Mattek) one day before imaging. Transient transfection of cells was performed using Lipofectamine™ 2000 reagent (Life Technologies) according to the manufacturer's recommendations: DNA (2.5 µg) was mixed with OptiMEM I (100 µL, Life Technologies) and Lipofectamine™ 2000 (6 µL) was mixed with OptiMEM I (100 µL). The solutions were incubated for 5 min at room temperature. They were mixed and incubated for 20 min at room temperature. Prepared DNA-Lipofectamine complex was added to a glass bottom 35 mm dish with cells at 50-70% confluency. After 6 h incubation in a humidified 5% CO$_2$ incubator at 37° C. the medium was changed to a fresh high-glucose DMEM medium with GlutaMAX-1 supplemented with 10% FBS. The cells were incubated for 1-2 days before imaging.

Staining

Cells were stained with 1-3 μM PA-SiR (1-2 h, 37° C.), washed with phenol-red free DMEM medium (Life Technologies) or PBS (once for 3 min, 37° C.) and imaged in the same medium.

Widefield Microscopy

Imaging was performed using a Leica DMI6000B microscope equipped with a Hamamatsu-C9100 EM-CCD camera and a HCX PL APO 100.0×1.47 Oil objective and a standard Cy5 filter set was used. Activation of the fluorophores was achieved by irradiation with the DAPI-channel at 100% for 10-20 s. The same settings (exposure time=150 ms, gain=3, EM-gain=800, transmission=12.5%) were used for the images taken before and after UV irradiation in the SiR-channel.

Confocal Microscopy

Confocal imaging was performed on a Leica DMi8 microscope equipped with a Leica TCS SP8 X scanhead, a white light laser, a 355 nm laser (Coherent) and HC PL APO 63×1.47 Oil objective. The 355 nm laser was used to perform the photoactivation.

All images were processed with Fiji.

Example 9

Synthesis 3,3'-(Dimethylsilanediyl)bis(N,N-dimethylaniline) (15)

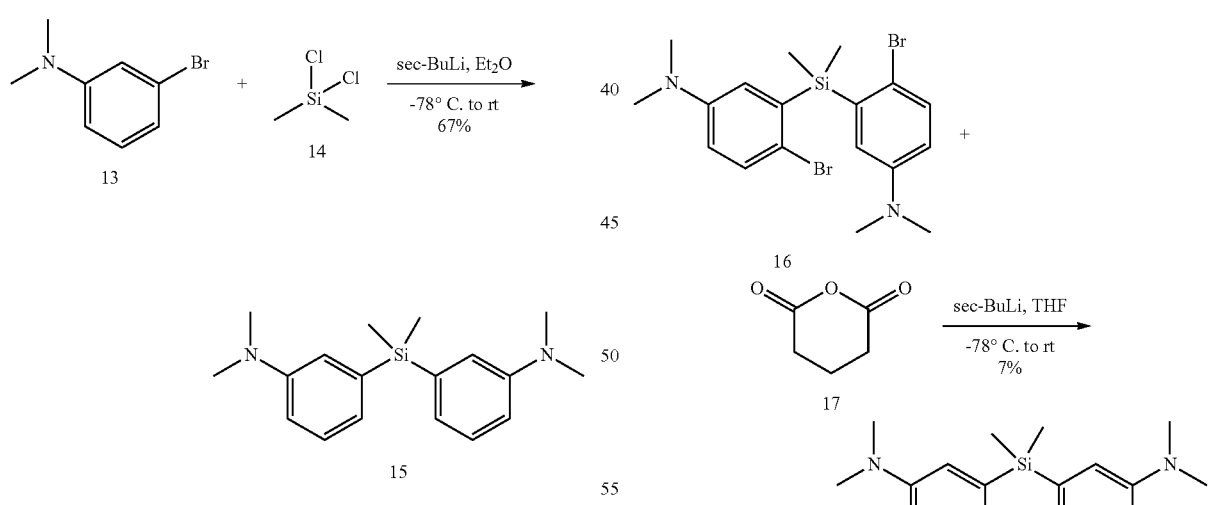

Following general procedure, A, flash column chromatography (SiO$_2$, hexane/EtOAc 100:0→70:30) gave 15 (1.598 g, 67%) as a colourless oil.

$^1$H NMR (400 MHz, CDCl$_3$) δ=0.56 (s, 6H), 2.94 (s, 12H), 6.78 (ddd, J=8.3, 2.8, 1.0 Hz, 2H), 6.92-6.98 (m, 4H), 7.22-7.31 ppm (m, 2H); $^{13}$C NMR (101 MHz, CDCl$_3$) δ=−2.01, 40.82, 113.68, 117.28, 118.46, 121.49, 122.86, 128.60, 139.07, 150.05 ppm; HRMS (ESI): m/z calcd for C$_{18}$H$_{27}$N$_2$Si$^+$ [M+H]$^+$ 299.1938, found 299.1940; LCMS (LC, 10% to 90%): t$_R$=3.31 min.

3,3'-(Dimethylsilanediyl)bis(4-bromo-N,N-dimethylaniline) (16)

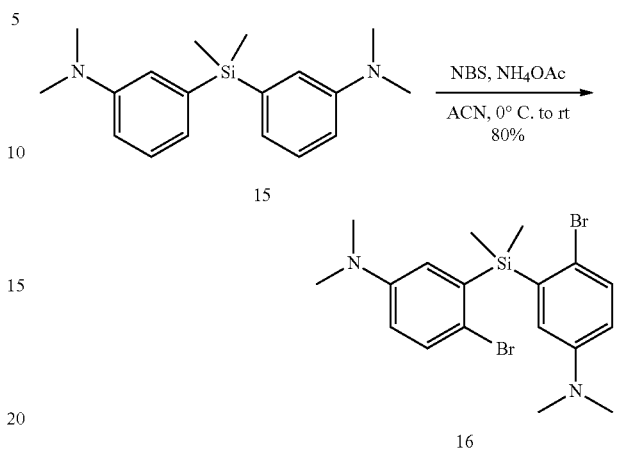

Following general procedure B, flash column chromatography (SiO$_2$, hexane/CH$_2$Cl$_2$ 100:0→0:100) gave 16 (2.270 g, 80%) as a beige solid.

$^1$H NMR (400 MHz, CDCl$_3$) δ =0.75 (s, 6H), 2.88 (s, 12H), 6.60 (dd, J=8.7, 3.2 Hz, 2H), 6.84 (d, J=3.2 Hz, 2H), 7.35 ppm (d, J=8.7 Hz, 2H); $^{13}$C NMR (101 MHz, CDC$_3$) δ=−0.79, 40.71, 115.40, 116.94, 121.92, 133.10, 138.87, 149.03 ppm; HRMS (ESI): m/z calcd for C$_{18}$H$_{25}$Br$_2$N$_2$Si$^+$ [M+H]$^+$ 455.0148, found 455.0145; LCMS (LC, 10% to 100%): t$_R$=5.18 min.

4-(3,7-Bis(dimethylamino)-5,5-dimethyldibenzo[b,e]silin-10(5H)-ylidene)butanoicacid (2a)

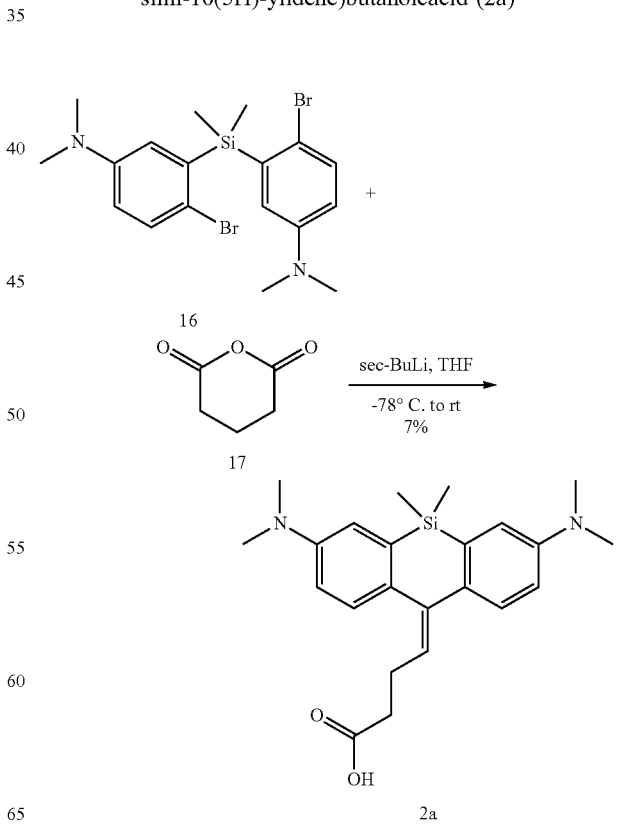

Following general procedure C, flash column chromatography (SiO$_2$, CH$_2$Cl$_2$/MeOH 100:0→90:10) and RP-HPLC (3 mL/min, 10% to 90% B in 32 min) gave 2a (23 mg, 7%) as a green solid.

$^1$H NMR (400 MHz, CD$_3$OD) δ=0.50 (s, 6H), 2.44 (t, J=7.2 Hz, 2H), 2.68 (d, J=7.4 Hz, 2H), 3.21 (s, 6H), 3.24 (s, 6H), 5.98 (t, J=7.3 Hz, 1H), 7.40 (ddd, J=39.8, 8.5, 2.7 Hz, 2H), 7.51-7.69 ppm (m, 4H); $^{13}$C NMR (101 MHz, CD$_3$OD) δ=−1.11, 26.63, 34.76, 45.68, 46.39, 120.02, 121.75, 123.67, 123.77, 128.57, 131.34, 134.12, 138.48, 140.26, 140.97, 143.25, 143.43, 144.46, 150.16, 176.34 ppm; HRMS (ESI): m/z calcd for C$_{23}$H$_{29}$N$_2$O$_2$Si$^-$ [M−H]$^{31}$ 393.2004, found 393.1992; LCMS (LC, 10% to 100%): t$_R$=2.58 min.

4-(3,7-Bis(dimethylamino)-5,5-dimethyldibenzo[b,e]silin-10(5H)-ylidene)-3-methylbutanoic acid (3a)

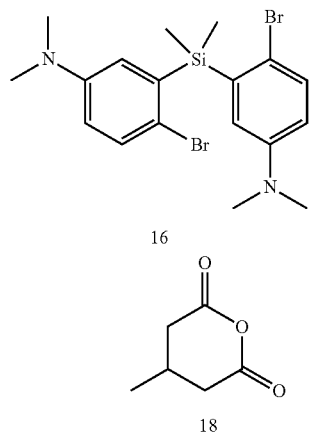

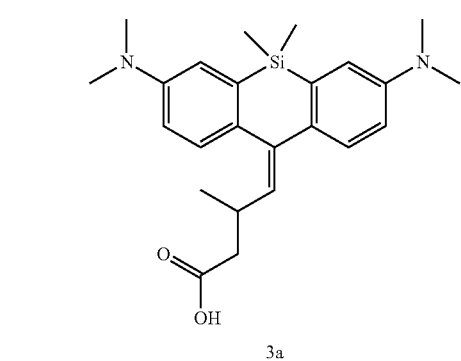

Following general procedure C, flash column chromatography (SiO$_2$, CH$_2$Cl$_2$/MeOH 100:0→90:10) and RP-HPLC (3 mL/min, 10% to 65% B in 32 min) gave 3a (0.9 mg, 0.6%) as a light blue solid.

$^1$H NMR (400 MHz, DMSO-d$_6$) δ=0.37 (s, 6H), 1.04 (d, J=7.0 Hz, 3H), 2.26 (br. s, 3H, overlaps with the residual solvent signal), 2.52 (s, 1H, overlaps with the residual solvent signal), 2.92-2.97 (m, 12H), 5.51 (d, J=10.3 Hz, 1H), 6.77-6.95 (m, 2H), 7.03 (s, 2H), 7.21-7.38 ppm (m, 2H); HRMS (ESI): m/z calcd for C$_{24}$H$_{31}$N$_2$O$_2$Si$^-$ [M−H]$^-$ 407.2160, found 407.2155; LCMS (LC, 10% to 100%): t$_R$=2.64 min.

N$^3$,N$^3$,N$^7$,N$^7$,5,5-Hexamethyl-10-propylidene-5,10-dihydrodibenzo[b,e]siline-3,7-diamine (4a)

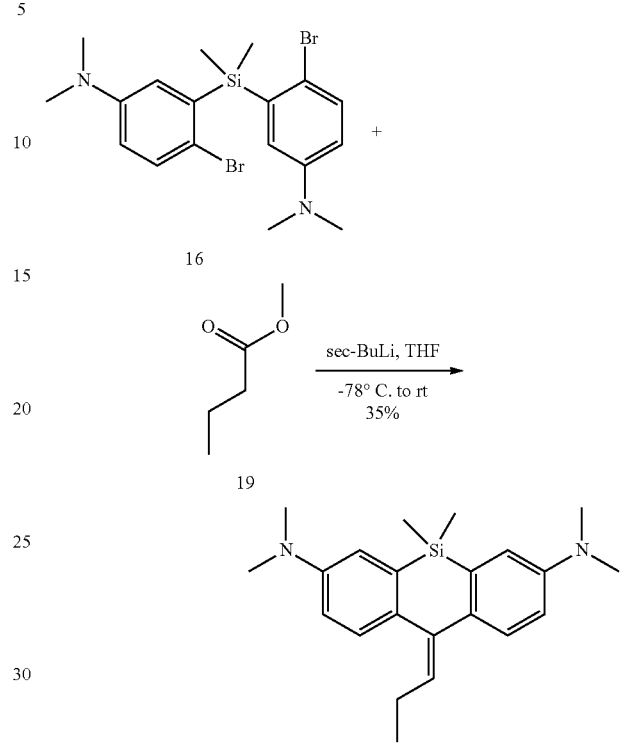

Following general procedure C, flash column chromatography (SiO$_2$, hexane/EtOAc 90:10→70:30) and RP-HPLC (3 mL/min, 10% to 100% B in 32 min) gave 4a (61 mg, 35%) as a white solid.

$^1$H NMR (400 MHz, CDCl$_3$) δ=0.42 (s, 6H), 1.02 (t, J=7.4 Hz, 3H), 2.40 (p, J=7.4 Hz, 2H), 2.94 (s, 6H), 2.97 (s, 6H), 5.73 (t, J=7.3 Hz, 1H), 6.74 (td, J=8.4, 2.8 Hz, 2H), 6.91 (d, J=2.9 Hz, 1H), 6.97 (d, J=2.8 Hz, 1H), 7.29 (d, J=8.5 Hz, 1H), 7.39 ppm (d, J=8.5 Hz, 1H).

N$^3$,N$^3$,N$^7$,N$^7$,5,5-Hexamethyl-10-methylene-5,10-dihydrodibenzo[b,e]siline-3,7-diamine (5a)

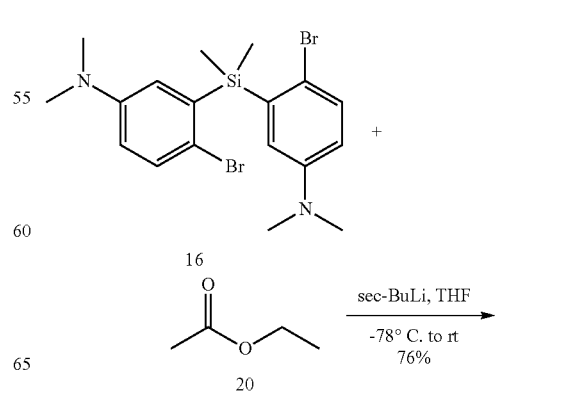

-continued

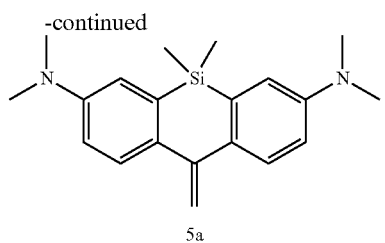

5a

Following general procedure C, washing of the crystals with MeOH gave 5a (195 mg, 76%) as a colourless solid.

$^1$H NMR (400 MHz, CDCl$_3$) δ=0.44 (s, 6H), 2.99 (s, 12H), 5.41 (s, 2H), 6.79 (dd, J=8.7, 2.8 Hz, 2H), 6.93 (d, J=2.8 Hz, 2H), 7.59 ppm (d, J=8.7 Hz, 2H); $^{13}$C NMR (101 MHz, CDCl$_3$) δ=−2.14, 40.85, 111.33, 114.17, 115.88, 126.93, 134.83, 135.20, 147.69, 149.17 ppm; HRMS (ESI): m/z calcd for C$_{20}$H$_{27}$N$_2$Si$^+$ [M+H]$^+$ 323.1938, found 323.1936; LCMS (LC, 10% to 100%): t$_R$=3.79 min.

3-(3,7-Bis(dimethylamino)-5,5-dimethyldibenzo[b,e]silin-10(5H)-ylidene)propanoic acid (22)

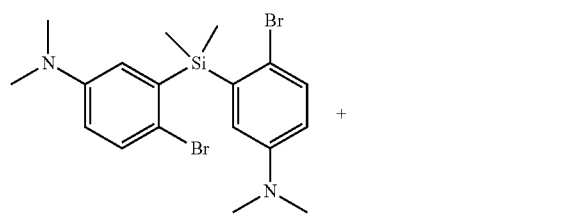

Following general procedure C, flash column chromatography (SiO$_2$, DCM/MeOH 100:0→90:10) gave 22 (46 mg, 24%) as a green solid.

$^1$H NMR (400 MHz, CD$_3$CN) δ=0.36-0.50 (br. s, 6H), 3.09 (s, 6H), 3.12 (s, 6H), 3.34 (d, J=7.5 Hz, 2H), 6.06 (t, J=7.5 Hz, 1H), 7.25 (dd, J=8.5, 2.7 Hz, 1H), 7.41 (dd, J=8.5, 2.7 Hz, 1H), 7.44 (d, J=8.5 Hz, 1H), 7.50 (d, J=2.7 Hz, 1H), 7.55-7.62 ppm (m, 2H); $^{13}$C NMR (101 MHz, CD$_3$CN) δ=35.56, 44.04, 45.48, 121.04, 122.09, 123.23, 125.15, 127.88, 130.45, 137.61, 138.75, 139.07, 142.38, 144.34, 146.14, 147.53, 172.88 ppm (two signals are hidden by the residual solvent signal).

3,7-Bis(dimethylamino)-4',4',5,5-tetramethyl-3',4'-dihydro-5H,5'H-spiro[dibenzo[b,e]siline-10,2'-furan]-5'-one (24)

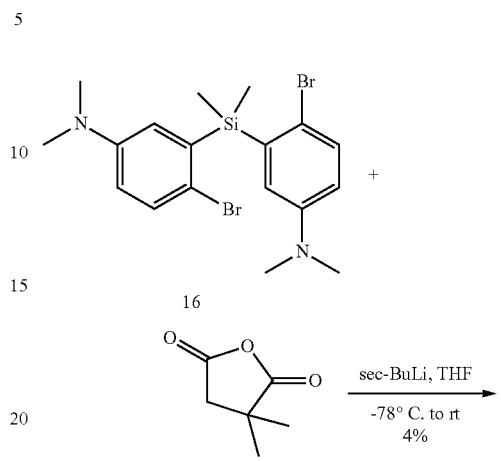

Following general procedure C, flash column chromatography (SiO$_2$, hexane/EtOAc 70:30→0:100) and RP-HPLC (3 mL/min, 10% to 100% B in 32 min) gave 24 (8.4 mg, 4%) as a white solid.

$^1$H NMR (400 MHz, DMSO-d$_6$) δ=0.45 (s, 3H), 0.59 (s, 3H), 1.10 (s, 6H), 2.28 (s, 2H), 2.96 (s, 12H), 6.87-6.97 (m, 2H), 7.09-7.20 (m, 2H), 7.33 ppm (d, J=8.7 Hz, 2H); $^{13}$C NMR (101 MHz, DMSO-d$_6$) δ=−2.83, 0.35, 26.86, NMe$_2$ hidden by the residual solvent signal, 40.93, 56.27, 83.83, 114.08, 116.97, 122.44, 133.63, 141.72, 147.69, 182.28 ppm; HRMS (ESI): m/z calcd for C$_{24}$H$_{33}$N$_2$O$_2$Si$^+$ [M+H]$^+$ 409.2306, found 409.2304; LCMS (LC, 10% to 100%): t$_R$=3.95 min.

3,7-Bis(dimethylamino)-10-isopropyl-5,5-dimethyl-5,10-dihydrodibenzo[b,e]silin-10-ol (26)

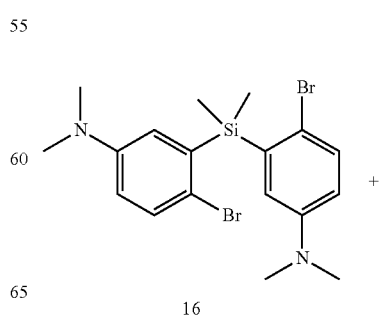

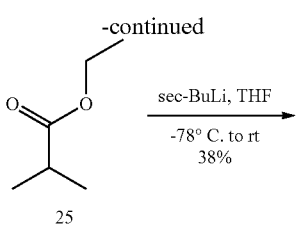

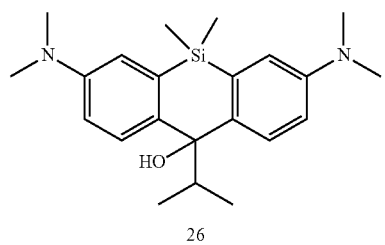

Following general procedure C, flash column chromatography (SiO$_2$, hexane/EtOAc 90:10→50:50) gave 26 (68 mg, 38%) as a white solid.

$^1$H NMR (400 MHz, CDCl$_3$) δ=0.45 (s, 3H), 0.48 (s, 3H), 0.70 (d, J=6.8 Hz, 6H), 2.97 (s, 12H), 6.82 (dd, J=8.8, 2.9 Hz, 2H), 6.93 (d, J=2.9 Hz, 2H), 7.75 ppm (d, J=8.8 Hz, 2H); $^{13}$C NMR (101 MHz, CDCl$_3$) δ=−0.62, 0.57, 18.19, 40.85, 43.42, 79.44, 113.52, 117.00, 127.22, 134.53, 141.39, 148.52 ppm.

4-(3,7-Bis(dimethylamino)-5,5-dimethyldibenzo[b,e]silin-10(5H)-ylidene)-2,2-dimethylbutanoic acid (28)

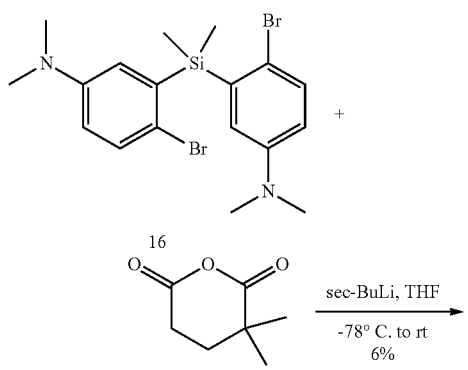

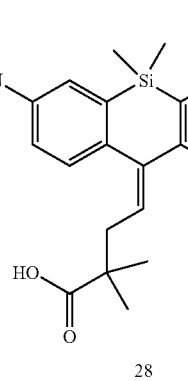

Following general procedure C, flash column chromatography (SiO$_2$, hexane/EtOAc 100:0→0:100) gave 28 (12 mg, 6%) as a green solid.

$^1$H NMR (400 MHz, CDCl$_3$) δ=0.41 (s, 6H), 1.16 (s, 6H), 2.71 (d, J=7.1 Hz, 2H), 2.94 (s, 6H), 2.98 (s, 6H), 5.73 (t, J=7.1 Hz, 1H), 6.74 (ddd, J=8.5, 6.7, 2.8 Hz, 2H), 6.91 (d, J=2.8 Hz, 1H), 6.96 (d, J=2.8 Hz, 1H), 7.26 (d, J=8.5 Hz, 1H), 7.38 ppm (d, J=8.5 Hz, 1H).

3,3'-(Diisopropylsilanediyl)bis(N,N-dimethylaniline) (30)

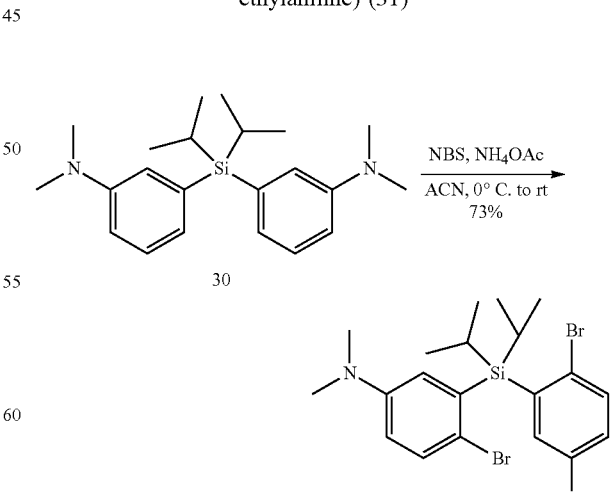

Following general procedure A, flash column chromatography (SiO$_2$, hexane/EtOAc 100:0→80:20) gave 30 (0.440 g, 31%) as a colourless oil.

$^1$H NMR (400 MHz, CDCl$_3$) δ=0.99 (d, J=7.4 Hz, 12H), 1.56 (hept, J=7.3 Hz, 2H), 2.93 (s, 12H), 6.81 (ddd, J=8.3, 2.7, 1.0 Hz, 2H), 6.91-7.01 (m, 4H), 7.21-7.31 ppm (m, 2H); $^{13}$C NMR (101 MHz, CDCl$_3$) δ=10.06, 17.82, 40.96, 113.65, 120.91, 125.16, 128.13, 133.91, 149.74 ppm; HRMS (ESI): m/z calcd for C$_{22}$H$_{35}$N$_2$Si$^+$ [M+H]$^+$ 355.2564, found 355.2567; LCMS (LC, 10% to 100%): t$_R$=4.87 min.

3,3'-(Diisopropylsilanediyl)bis(4-bromo-N,N-dimethylaniline) (31)

Following general procedure B, flash column chromatography (SiO$_2$, hexane/CH$_2$Cl$_2$ 100:0→0:100) gave 31 (1.087 g, 73%) as a white solid.

$^1$H NMR (400 MHz, CDCl$_3$) δ=1.17 (d, J=7.5 Hz, 12H), 2.00 (p, J=7.4 Hz, 2H), 2.92 (s, 12H), 6.60 (dd, J=8.8, 3.3 Hz, 2H), 6.97 (d, J=3.2 Hz, 2H), 7.33 ppm (d, J=8.7 Hz, 2H); $^{13}$C NMR (101 MHz, CDCl$_3$) δ=12.68, 19.12, 40.80, 115.10, 117.63, 122.75, 133.40, 136.75, 148.57 ppm; HRMS (ESI): m/z calcd for C$_{22}$H$_{33}$Br$_2$N$_2$Si$^+$ [M+H]$^+$ 511.0774, found 511.0779; LCMS (LC, 10% to 100%): $t_R$=5.73 min.

4-(3,7-Bis(dimethylamino)-5,5-diisopropyldibenzo[b,e]silin-10(5H)-ylidene)butanoic acid (6a)

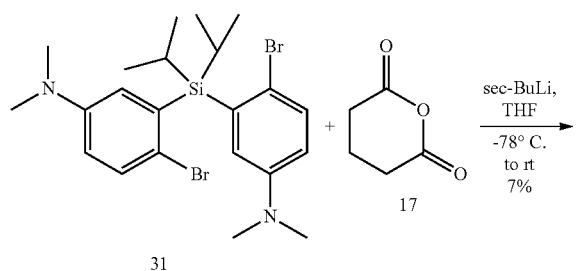

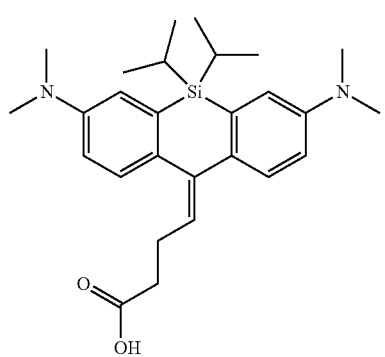

Following general procedure C, flash column chromatography (SiO$_2$, hexane/EtOAc 100:0→50:50) and RP-HPLC (3 mL/min, 10% to 90% B in 32 min) gave 6a (6.7 mg, 7%) as a light blue solid.

$^1$H NMR (400 MHz, CD$_3$OD) δ=1.09 (dd J=7.7 Hz, 12H), 1.50-1.65 (m, 2H), 2.41 (t, J=7.4 Hz, 2H), 2.65 (q, J=7.6 Hz, 2H), 3.20 (s, 6H), 3.24 (s, 6H), 5.90 (t, J=7.2 Hz, 1H), 7.37 (dd, J=8.6, 2.7 Hz, 1H), 7.48-7.61 (m, 4H), 7.69 ppm (d, J=8.5 Hz, 1H); $^{13}$C NMR (101 MHz, CD$_3$OD) δ=12.87, 18.43, 26.94, 34.84, 44.48, 45.82, 118.48, 120.96, 122.99, 123.90, 128.71, 131.61, 133.71, 134.66, 135.99, 141.75, 142.16, 143.85, 145.71, 150.46, 176.48 ppm; HRMS (ESI): m/z calcd for C$_{27}$H$_{37}$N$_2$O$_2$Si$^-$ [M−H]$^-$ 449.2630, found 449.2622; LCMS (LC, 10% to 90%): $t_R$=3.92 min.

5-Bromo-2-fluoro-N,N-dimethylaniline (33)

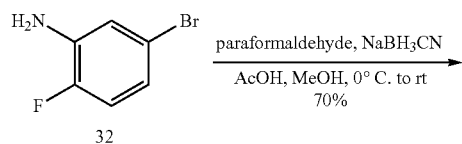

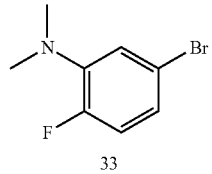

A solution of 5-bromo-2-fluoroaniline (32) (5.0 g, 26.3 mmol, 1.0 eq.) in MeOH (30 mL) was treated with acetic acid (40 mL) and paraformaldehyde (3.9 g, 131.6 mmol, 5.0 eq.). The mixture was cooled down to 0° C. and stirred for 15 min. NaBH$_3$CN (5.0 g, 78.9 mmol, 3.0 eq.) was added portion wise to the mixture over 10 min. The mixture was warmed up to room temperature and was stirred for 16 h. The mixture was evaporated and then neutralised with aqueous NaOH solution (4 mL, 5 M). The aqueous layer was extracted with CH$_2$Cl$_2$ (3×100 mL). The combined organic layers were dried over MgSO$_4$, filtered and evaporated to afford the crude product. Flash column chromatography (SiO$_2$, hexane/EtOAc 100:0→85:15) gave 33 (3.990 g, 70%) as a yellow oil.

$^1$H NMR (400 MHz, CDCl$_3$) δ=2.85 (d, J=1.0 Hz, 6H), 6.86 (dd, J=12.6, 8.4 Hz, 1H), 6.90-6.99 ppm (m, 2H); $^{13}$C NMR (101 MHz, CDCl$_3$) δ=42.68 (d, J=4.5 Hz), 116.87 (d, J=3.3 Hz), 117.58 (d, J=22.8 Hz), 121.18 (d, J=3.9 Hz), 123.28 (d, J=7.9 Hz), 142.10 (d, J=9.7 Hz), 154.07 ppm (d, J=245.3 Hz); $^{19}$F NMR (376 MHz, CDCl$_3$) δ=−124.69--124.58 ppm (m); HRMS (ESI): m/z calcd for C$_8$H$_{10}$BrFN$^+$ [M+H]$^+$ 217.9975, found 217.9978; LCMS (LC, 10% to 90%): $t_R$=4.09 min.

5,5'-(Dimethylsilanediyl)bis(2-fluoro-N,N-dimethylaniline) (34)

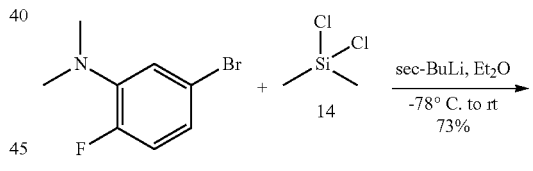

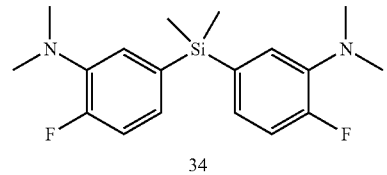

Following general procedure A, flash column chromatography (SiO$_2$, hexane/EtOAc 100:0→85:15) gave 34 (2.110 g, 73%) as a yellow oil.

$^1$H NMR (400 MHz, CDCl$_3$) δ=0.52 (s, 6H), 2.83 (d, J=0.9 Hz, 12H), 6.98-7.06 ppm (m, 6H); $^{13}$C NMR (101 MHz, CDCl$_3$) δ=−1.86, 43.01 (d, J=3.9 Hz), 115.92 (d, J=19.8 Hz), 123.97 (d, J=3.4 Hz), 127.57 (d, J=7.5 Hz), 134.00 (d, J=4.3 Hz), 140.33 (d, J=8.0 Hz), 156.31 ppm (d, J=248.0 Hz); $^{19}$F NMR (376 MHz, CDCl$_3$) δ=−121.34--121.21 ppm (m); HRMS (ESI): m/z calcd for C$_{18}$H$_{25}$F$_2$N$_2$Si$^+$ [M+H]$^+$ 335.1750, found 335.1754; LCMS (LC, 10% to 90%): $t_R$=4.89 min.

5,5'-(Dimethylsilanediyl)bis(4-bromo-2-fluoro-N,N-dimethylaniline) (35)

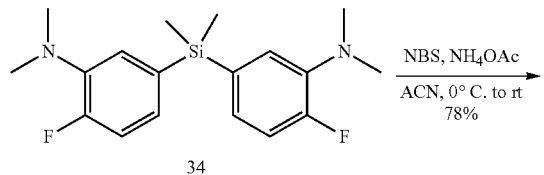

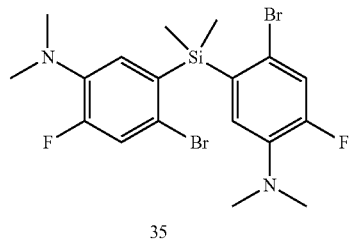

Following general procedure B, flash column chromatography (SiO₂, hexane/CH₂Cl₂ 100:0→0:100) gave 35 (2.329 g, 78%) as a beige solid.

¹H NMR (400 MHz, CDCl₃) δ=0.74 (s, 6H), 2.80 (d, J=1.0 Hz, 12H), 6.94 (d, J=10.2 Hz, 2H), 7.20 ppm (d, J=12.5 Hz, 2H); ¹³C NMR (101 MHz, CDCl₃) δ=−0.80, 42.70 (d, J=4.0 Hz), 119.91 (d, J=8.6 Hz), 120.90 (d, J=23.2 Hz), 126.70 (d, J=4.0 Hz), 134.08 (d, J=4.0 Hz), 139.37 (d, J=7.5 Hz), 155.57 ppm (d, J=252.7 Hz); ¹⁹F NMR (376 MHz, CDCl₃) δ=−118.89 ppm (t, J=11.3 Hz); HRMS (ESI): m/z calcd for C₁₈H₂₃Br₂F₂N₂Si⁺ [M+H]⁺ 490.9960, found 490.9954; LCMS (LC, 10% to 100%): $t_R$=5.50 min.

4-(3,7-Bis(dimethylamino)-2,8-difluoro-5,5-dimethyldibenzo[b,e]silin-10(5H)-ylidene)butanoic acid (36)

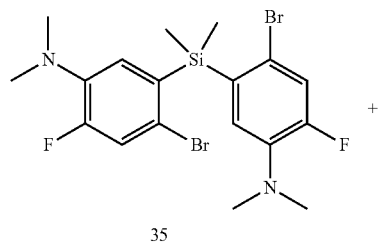

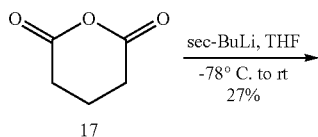

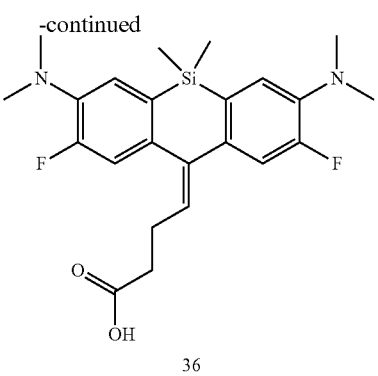

Following general procedure C, flash column chromatography (SiO₂, hexane/EtOAc 80:20→0:100) and RP-HPLC (3 mL/min, 10% to 90% B in 32 min) gave 36 (24 mg, 27%) as a white solid.

¹H NMR (400 MHz, ACN-d₃) δ=0.45 (s, 6H), 2.45 (t, J=7.1 Hz, 2H), 2.61-2.68 (m, 2H), 3.08 (d, J=12.9 Hz, 12H), 5.98 (t, J=7.2 Hz, 1H), 7.33 (ddd, J=13.5, 12.1, 1.1 Hz, 2H), 7.50-7.63 ppm (m, 2H); ¹³C NMR (101 MHz, CD₃OD) δ=−1.27, 26.48, 34.67, 44.58 (d, J=3.2 Hz), 45.20 (d, J=2.8 Hz), 115.24 (d, J=20.2 Hz), 117.95 (d, J=20.4 Hz), 124.85, 133.20 (d, J=4.2 Hz), 133.95, 134.29, 134.82 (d, J=4.3 Hz), 139.92, 140.07, 142.25 (d, J=6.8 Hz), 149.66 (d, J=8.1 Hz), 155.32 (d, J=87.3 Hz), 157.79 (d, J=87.8 Hz), 176.37 ppm; ¹⁹F NMR (376 MHz, ACN-d₃) δ=−122.40−−122.10 (m), −122.07−−120.43 ppm (m); HRMS (ESI): m/z calcd for C₂₃H₂₇F₂N₂O₂Si⁻ [M−H]⁻ 429.1815, found 429.1816; LCMS (LC, 10% to 90%): $t_R$=4.22 min.

1-(3-Bromophenyl)azetidine (39)

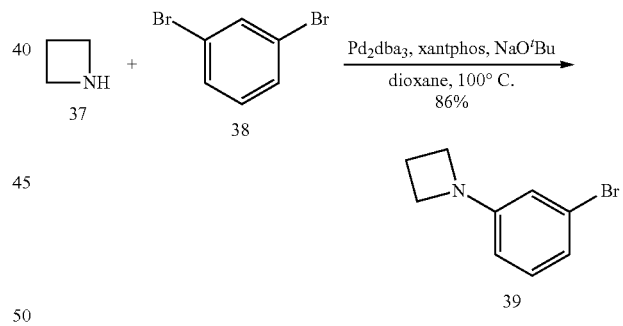

A solution of 1,3-dibromobenzene (38) (2.3 g, 10.0 mmol, 1.5 eq.), Pd₂dba₃ (305 mg, 0.3 mmol, 0.05 eq.), xantphos (387 mg, 0.7 mmol, 0.1 eq.) and NaOᵗBu (1.9 g, 20.0 mmol, 3.0 eq.) in 1,4-dioxane (50 mL) was degassed with argon for 5 min. Azetidine (37) (452 μL, 6.7 mmol, 1.0 eq.) was added and the mixture was again degassed with argon for 10 min. The mixture was stirred at 100° C. for 2 h. The mixture was let cool down to room temperature and was diluted with EtOAc and aqueous saturated NaHCO₃ solution. The organic layer was washed with aqueous saturated NaHCO₃ (2×50 mL), brine, dried over MgSO₄, filtered and evaporated to afford the crude product. Flash column chromatography (SiO₂, hexane/EtOAc 100:0→80:20) gave 39 (1.224 g, 86%) as a yellow oil.

¹H NMR (400 MHz, CDCl₃) δ=2.37 (p, J=7.3 Hz, 2H), 3.87 (t, J=7.3 Hz, 4H), 6.34 (ddd, J=8.1, 2.2, 0.9 Hz, 1H), 6.56 (t, J=2.1 Hz, 1H), 6.82 (ddd, J=7.9, 1.9, 0.9 Hz, 1H), 7.04 ppm (t, J=8.0 Hz, 1H); $^{13}$C NMR (101 MHz, CDCl$_3$) δ=16.99, 52.42, 109.93, 114.17, 120.00, 123.14, 130.29, 153.32 ppm; HRMS (ESI): m/z calcd for C$_9$H$_{11}$BrN$^+$ [M+H]$^+$ 212.0069, found 221.0065; LCMS (LC, 10% to 90%): t$_R$=4.17 min.

Bis(3-(azetidin-1-yl)phenyl)dimethylsilane (40)

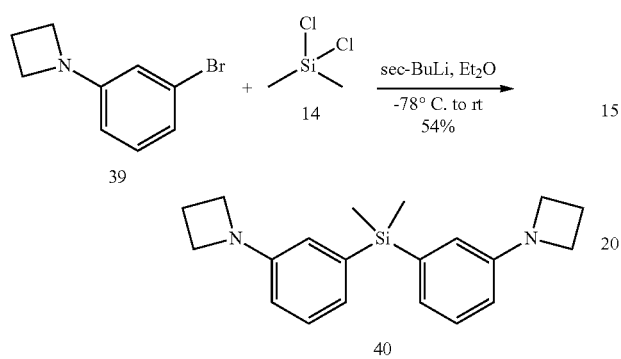

Following general procedure A, flash column chromatography (SiO$_2$, hexane/EtOAc 100:0→60:40) gave 40 (0.473 g, 54%) as a colourless oil.

$^1$H NMR (400 MHz, CDCl$_3$) δ=0.51 (s, 6H), 2.34 (p, J=7.2 Hz, 4H), 3.86 (t, J=7.2 Hz, 8H), 6.47 (ddd, J=8.1, 2.4, 0.8 Hz, 2H), 6.61 (d, J=2.1 Hz, 2H), 6.90 (dt, J=7.2, 1.1 Hz, 2H), 7.20 ppm (t, J=7.6 Hz, 2H); $^{13}$C NMR (101 MHz, CDCl$_3$) δ=−2.09, 17.17, 52.61, 112.27, 116.87, 123.43, 128.35, 138.92, 151.64 ppm; HRMS (ESI): m/z calcd for C$_{20}$H$_{27}$N$_2$Si$^+$ [M+H]$^+$ 323.1938, found 323.1944; LCMS (LC, 10% to 90%): t$_R$=4.88 min.

Bis(5-(azetidin-1-yl)-2-bromophenyl)dimethylsilane (41)

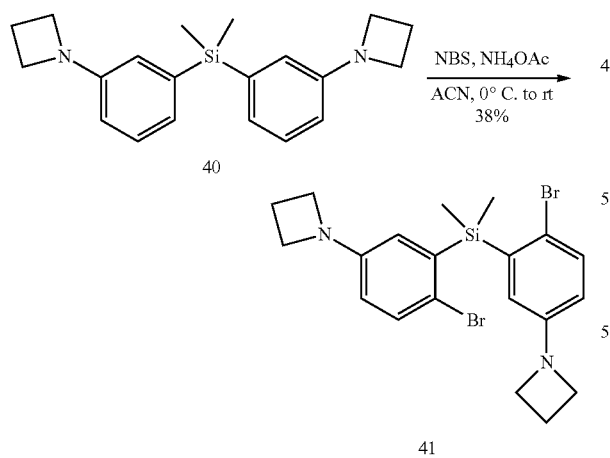

Following general procedure B, flash column chromatography (SiO$_2$, hexane/EtOAc 100:0→80:20) gave 41 (0.085 g, 38%) as a beige solid.

$^1$H NMR (400 MHz, CDCl$_3$) δ=0.71 (s, 6H), 2.33 (p, J=7.2 Hz, 4H), 3.81 (t, J=7.2 Hz, 8H), 6.31 (dd, J=8.5, 2.9 Hz, 2H), 6.51 (d, J=3.0 Hz, 2H), 7.31 ppm (d, J=8.5 Hz, 2H); $^{13}$C NMR (101 MHz, CDCl$_3$) δ=−0.89, 17.04, 52.59, 114.15, 117.54, 120.40, 132.95, 138.93, 150.62 ppm; HRMS (ESI): m/z calcd for C$_{20}$H$_{25}$Br$_2$N$_2$Si$^+$ [M+H]$^+$ 479.0148, found 479.0146; LCMS (LC, 10% to 100%): t$_R$=5.40 min.

3-(3,7-Di(azetidin-1-yl)-5,5-dimethyldibenzo[b,e]silin-10(5H)-ylidene)propanoic acid (42)

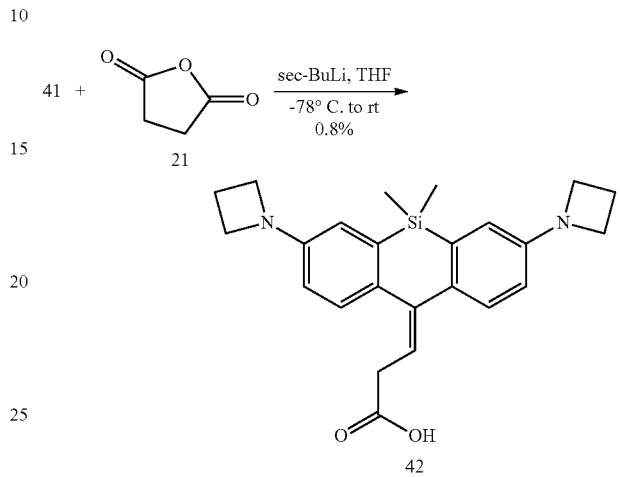

A solution of 41 (91 mg, 0.19 mmol, 1.0 eq.) in dry THF (3 mL) was cooled down to −78° C. sec-BuLi (0.4 mL, 0.56 mmol, 3.0 eq., 1.3 M in cyclohexane) was added dropwise over 5 min and the mixture was stirred for 30 min at −78° C. A solution of succinic anhydride (21) (21 mg, 0.21 mmol, 1.1 eq.) in dry THF (1.0 mL) was added to the mixture. The mixture was stirred at −78° C. for 15 min and then warmed up to room temperature and stirred for 30 min. Saturated ammonium chloride solution was added and extracted with EtOAc (2×25 mL). The combined organic layers were dried over MgSO$_4$, filtered and evaporated to afford the crude product. Flash column chromatography (SiO$_2$, hexane/EtOAc 90:10→70:30) and RP-HPLC (3 mL/min, 10% to 90% B in 32 min) gave 42 (0.63 mg, 0.8%) as a light blue solid.

$^1$H NMR (400 MHz, CD$_3$CN) δ=0.33 (m, 6H), 2.34-2.37 (m, 4H, hidden by residual solvent signal), 3.28 (d, J=6.8 Hz, 2H), 3.89 (td, J=7.2, 3.3 Hz, 8H), 5.80 (t, J=7.6 Hz, 1H), 6.49 (ddd, J=11.0, 8.3, 2.6 Hz, 2H), 6.68 (d, J=2.6 Hz, 1H), 6.73 (d, J=2.5 Hz, 1H), 7.22 (d, J=8.3 Hz, 1H), 7.32 ppm (d, J=8.4 Hz, 1H).

4-(3,7-Bis(dimethylamino)-5,5-dimethyldibenzo[b,e]silin-10(5H)-ylidene)-N-(2-(2-((6-chlorohexyl)oxy)ethoxy)ethyl)butanamide (44, PA-SiR-Halo)

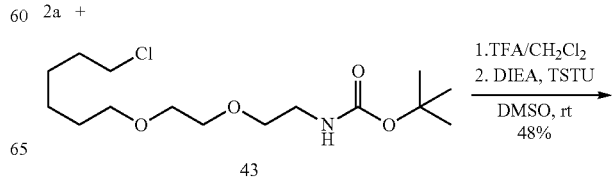

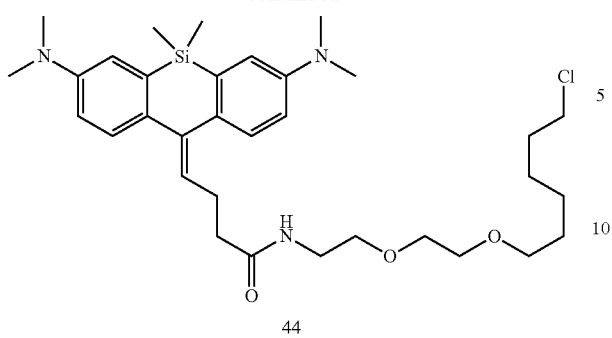

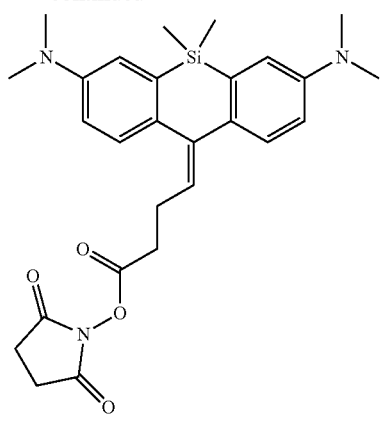

A solution of 2a (1.8 mg, 4.5 μmol, 1.0 eq.) in DMSO (250 μL) was treated with DIEA (2.2 μL, 13.5 μmol, 3.0 eq.) and TSTU (1.6 mg, 5.4 μmol, 1.2 eq.). The mixture was shaken for 20 min at room temperature. In a separate vial a solution of Halo-NHBoc 43 (2.0 mg, 6.2 μmol, 1.4 eq.) in CH$_2$Cl$_2$/TFA (8:2, 80 μL) was shaken for 5 min. The solution was evaporated and dried on the high vacuum for 1 h. The residue was taken up in DMSO (50 μL) and added to the other mixture. The mixture was shaken for 10 min and then acidified with TFA (3 μL). RP-HPLC (3 mL/min, 10% to 90% B in 32 min) gave 44 (1.3 mg, 48%) as a light blue solid.

$^1$H NMR (400 MHz, CD$_3$OD) δ=0.45 (s, 6H), 1.30-1.47 (m, 4H), 1.56 (p, J=6.8 Hz, 2H), 1.73 (p, J=6.9 Hz, 2H), 2.34 (t, J=7.3 Hz, 2H), 2.69 (q, J=7.3 Hz, 2H), 3.10 (s, 6H), 3.14 (s, 6H), 3.16-3.26 (m, 2H), 3.33 (d, J=5.7 Hz, 3H, overlaps with the residual solvent signal), 3.40-3.52 (m, 8H), 5.85 (t, J=7.2 Hz, 1H), 7.09 (d, J=8.6 Hz, 1H), 7.22 (d, J=8.4 Hz, 1H), 7.28 (s, 1H), 7.35 (s, 1H), 7.41 (d, J=8.5 Hz, 1H), 7.53 (d, J=8.5 Hz, 1H), 8.02-8.12 ppm (m, 1H); HRMS (ESI): m/z calcd for C$_{63}$H$_{51}$ClN$_3$O$_3$Si$^+$ [M+H]$^+$ 600.3383, found 600.3386; LCMS (LC, 10% to 100%): t$_R$=3.61 min.

2,5-Dioxopyrrolidin-1-yl-4-(3,7-bis(dimethylamino)-5,5-dimethyldibenzo[b,e]silin-10(5H)-ylidene)butanoate (45)

A solution of 2a (5.1 mg, 13.0 μmol, 1.0 eq.) in DMSO (300 μl) was treated with DIEA (6.0 μL, 39 μmol, 3.0 eq.) and TSTU (4.7 mg, 15.6 μmol, 1.2 eq.). The mixture was shaken for 30 min at room temperature and then acidified with TFA (2 μL). RP-HPLC (3 mL/min, 0% to 90% B in 32 min) gave 45 (2.1 mg, 33%) as a light green solid.

$^1$H NMR (400 MHz, CD$_3$OD) δ=0.51 (br. s, 6H), 2.77-2.89 (m, 8H), 3.21 (s, 6H), 3.26 (s, 6H), 5.98-6.09 (m, 1H), 7.31 (dd, J=8.4, 2.8 Hz, 1H), 7.46 (dd, J=8.4, 2.7 Hz, 1H), 7.51 (d, J=2.7 Hz, 1H), 7.55 (d, J=8.5 Hz, 1H), 7.59 (d, J=2.7 Hz, 1H), 7.68 ppm (d, J=8.5 Hz, 1H); $^{13}$C NMR (101 MHz, CD$_3$OD) δ=−1.78, 24.76, 25.08, 30.31, 42.65, 44.22, 116.61, 119.21, 120.15, 121.18, 127.08, 129.51, 133.26, 136.90, 138.08, 138.48, 139.02, 140.84, 141.30, 142.95, 168.29, 170.40 ppm; HRMS (ESI): m/z calcd for C$_{27}$H$_{34}$N$_3$O$_4$Si$^+$ [M+H]$^+$ 492.2312, found 492.2311; LCMS (LC, 10% to 90%): t$_R$=3.50 min.

N-(4-(((2-Amino-9H-purin-6-yl)oxy)methyl)benzyl)-4-(3,7-bis(dimethylamino)-5,5-dimethyldibenzo[b,e]silin-10(5H)-ylidene)butanamide (47, PA-SiR-SNAP)

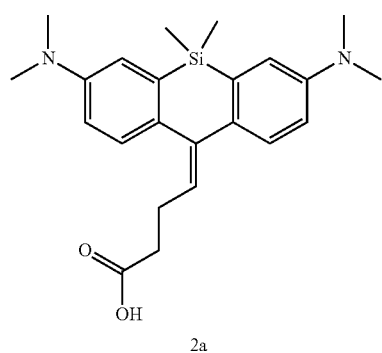

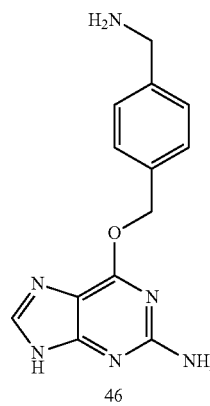

-continued

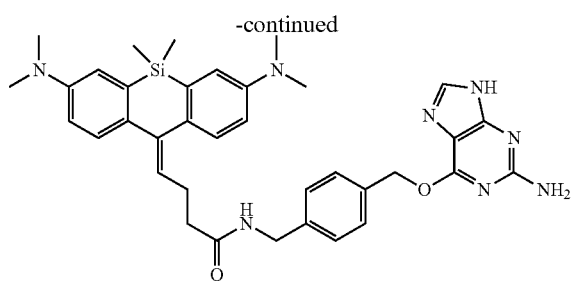

47

A solution of 45 (1.2 mg, 3.0 μmol, 1.0 eq.) in DMSO (100 μl) was treated with DIEA (1.5 μL, 9 μmol, 3.0 eq.) and BG-NH₂ 46 (1.0 mg, 3.8 μmol, 1.3 eq.). The mixture was shaken for 10 min at room temperature and then acidified with TFA (2 μL). RP-HPLC (3 mL/min, 0% to 90% B in 32 min) gave 47 (1.5 mg, 77%) as a green solid.

$^1$H NMR (600 MHz, DMSO-d$_6$) δ=0.35 (br. s, 8H (should be 6H)), 2.24 (t, J=7.4 Hz, 2H), 2.55-2.65 (m, 1H, overlaps with the residual solvent signal), 2.92 (s, 6H), 2.94 (s, 6H), 4.23 (d, J=5.9 Hz, 2H), 5.48 (s, 2H), 5.66 (t, J=7.0 Hz, 1H), 6.80-6.87 (m, 2H), 6.97-7.05 (m, 2H), 7.22 (d, J=7.9Hz, 2H), 7.26 (d, J=8.5 Hz, 1H), 7.29 (d, J=8.5 Hz, 1H), 7.39 (d, J=8.0 Hz, 2H), 8.35 (t, J=6.0 Hz, 1H), 8.94 ppm (s, 1H); HRMS (ESI): m/z calcd for C$_{36}$H$_{43}$N$_8$O$_2$Si$^+$ [M+H]$^+$ 647.3278, found 647.3274; LCMS (LC, 10% to 100%): t$_R$=2.41 min.

N-(4-((4R,7R,10S,13S,19S,E)-7-((1H-Indol-2-yl)methyl)-4-(4-hydroxyphenyl)-8,13,15,19-tetramethyl-2,6,9,12-tetraoxo-1-oxa-5,8,11-triazacyclononadec-15-en-10-yl)butyl)-4-(3,7-bis(dimethylamino)-5,5-dimethyldibenzo[b,e]silin-10(5H)-ylidene)butanamide (49, PA-SiR-Actin)

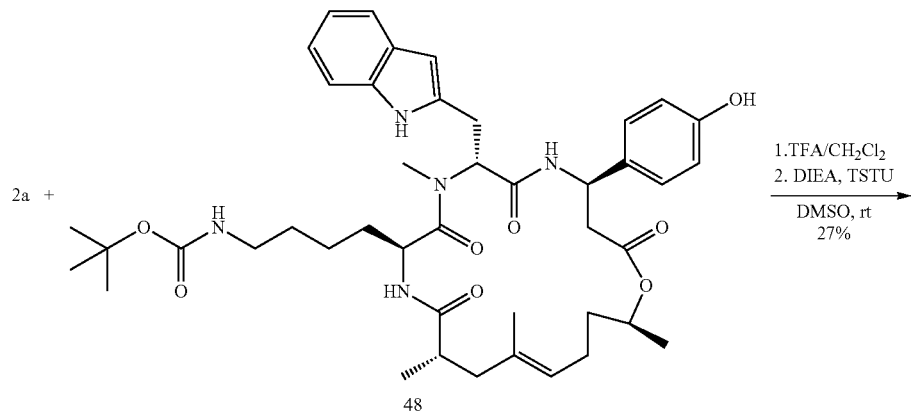

48

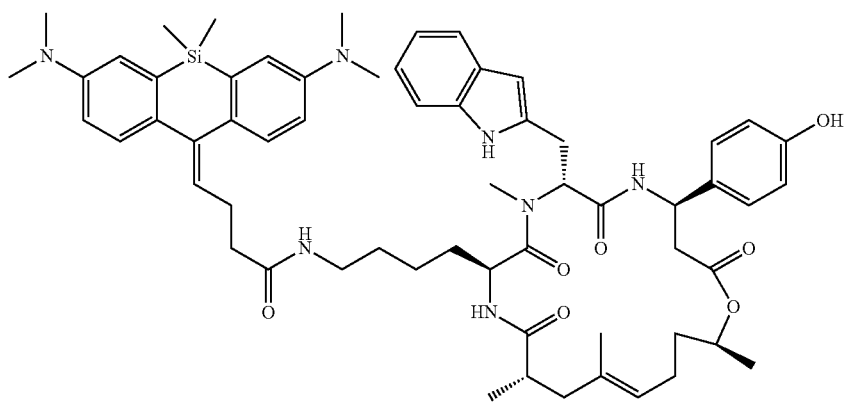

49

A solution of 2a (1.8 mg, 4.5 µmol, 1.0 eq.) in DMSO (300 µL) was treated with DIEA (2.2 µL, 13.5 µmol, 3.0 eq.) and TSTU (1.6 mg, 5.4 µmol, 1.2 eq.). The mixture was shaken for 20 min at room temperature. In a separate vial a solution of jasplakinolide-NHBoc 48 (3.8 mg, 5.0 µmol, 1.1 eq.) in CH$_2$Cl$_2$/TFA (8:2, 80 µL) was shaken for 2 min. The solution was evaporated and dried on the high vacuum for 1 h. The residue was taken up in DMSO (50 µL) and added to the other mixture. The mixture was shaken for 30 min and then acidified with TFA (3 µL). RP-HPLC (3 mL/min, 10% to 90% B in 32 min) gave 49 (1.3 mg, 27%) as a light blue solid.

$^1$H NMR (400 MHz, DMSO-d$_6$) δ=0.37 (s, 6H), 0.73-0.83 (m, 4H), 0.89 (d, J=6.8 Hz, 3H), 1.06 (p, J=7.1, 6.7 Hz, 1H), 1.15 (d, J=6.3 Hz, 3H), 1.19-1.29 (m, 6H), 1.30-1.41 (m, 1H), 1.42-1.55 (m, 5H), 1.75-1.91 (m, 2H), 2.08-2.20 (m, 3H), 2.58-2.71 (m, 2H), 2.72-2.93 (m, 2H), 2.93-2.96 (m, 12H), 3.00 (s, 3H), 4.44-4.58 (m, 1H), 4.66 (h, J=6.3 Hz, 1H), 4.91 (t, J=7.1 Hz, 1H), 5.18 (ddd, J=11.6, 8.8, 3.1 Hz, 1H), 5.50 (dd, J=11.3, 5.2 Hz, 1H), 5.65 (t, J=7.1 Hz, 1H), 6.64-6.72 (m, 2H), 6.77-6.88 (m, 2H), 6.93 (t, J=7.4 Hz, 1H), 6.97-7.06 (m, 3H), 7.09-7.15 (m, 2H), 7.23-7.34 (m, 3H), 7.66 (t, J=7.7 Hz, 2H), 7.73 (t, J=5.6 Hz, 1H), 8.64 (d, J=8.8 Hz, 1H), 9.30 (br. s, 1H), 10.78 ppm (d, J=2.3 Hz, 1H); HRMS (ESI): m/z calcd for C$_{61}$H$_{80}$N$_7$O$_7$Si$^+$ [M+H]$^+$ 1050.5883, found 1050.5902; LCMS (LC, 10% to 90%): t$_R$=3.91 min.

4-(3,7-Bis(dimethylamino)-5,5-dimethyldibenzo[b,e]silin-10(5H)-ylidene)-N-(4-(4-(6-(4-methylpiperazin-1-yl)-1H,3'H-[2,5'-bibenzo[d]imidazol]-2'-yl)henoxy)butyl)butanamide (51, PA-SiR-DNA)

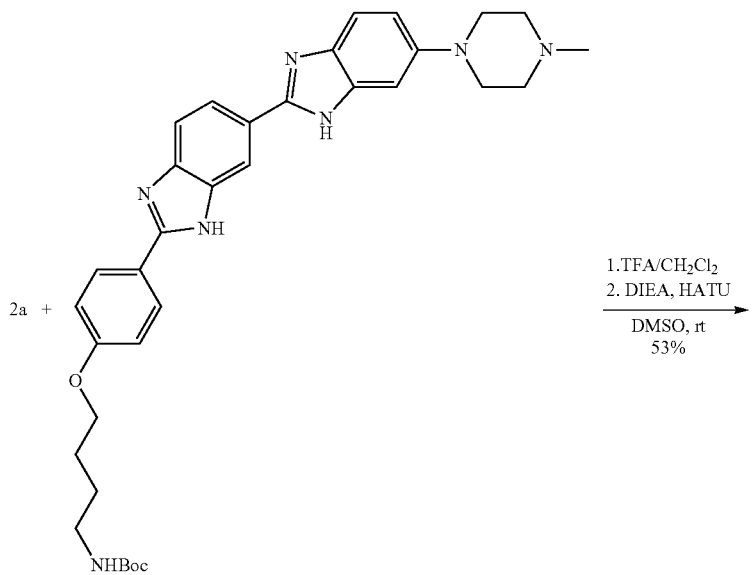

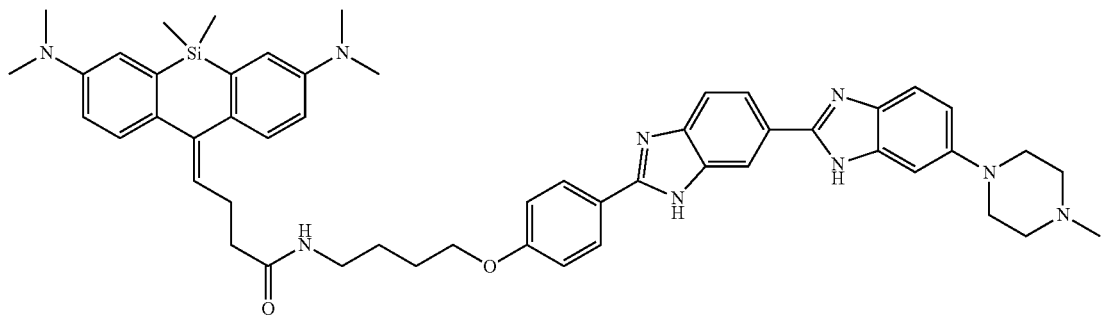

A solution of 2a (1.1 mg, 3.0 µmol, 1.0 eq.) in DMSO (150 µL) was treated with DIEA (1.5 µL, 9.0 µmol, 3.0 eq.) and HATU (1.4 mg, 3.6 µmol, 1.2 eq.). The mixture was shaken for 20 min at room temperature. In a separate vial a solution of 50 (2.1 mg, 3.6 µmol, 1.2 eq.) in CH$_2$Cl$_2$/TFA (8:2, 80 µL) was shaken for 5 min. The solution was evaporated and dried on the high vacuum for 1 h. The residue was taken up in DMSO (50 µL) and added to the other mixture. The mixture was shaken for 15 min and then acidified with TFA (3 µL) and diluted with water (200 µL). RP-HPLC (3 mL/min, 0% to 90% B in 32 min) gave 51 (1.4 mg, 53%) as a light green solid.

$^1$H NMR (400 MHz, CD$_3$OD) δ=0.49 (d, J=7.8 Hz, 6H), 1.59-1.75 (m, 2H), 1.75-1.89 (m, 2H), 2.36 (t, J=7.3 Hz, 2H), 2.71 (q, J=7.3 Hz, 2H), 3.02 (s, 3H), 3.15 (s, 6H), 3.17 (s, 6H), 3.25 (t, J=6.9 Hz, 2H), 3.61-3.77 (m, 4H), 3.90-4.03 (m, 4H), 4.07 (t, J=6.2 Hz, 2H), 5.93 (t, J=7.2 Hz, 1H), 7.14 (d, J=8.7 Hz, 2H), 7.23 (dd, J=8.5, 2.7 Hz, 1H), 7.29-7.35 (m, 2H), 7.38-7.44 (m, 2H), 7.45-7.52 (m, 2H), 7.58 (d, J=8.5 Hz, 1H), 7.73 (d, J=9.0 Hz, 1H), 7.90 (d, J=8.6 Hz, 1H), 8.04 (dd, J=8.6, 1.7 Hz, 1H), 8.11 (d, J=8.6 Hz, 2H), 8.40 ppm (d, J=1.7 Hz, 1H); HRMS (ESI): m/z calcd for C$_{52}$H$_{62}$N$_9$O$_2$Si$^+$ [M+H]$^+$ 872.4790, found 872.4797; LCMS (LC, 10% to 100%): t$_R$=2.42 min.

(2αR,4S,4αS,6R,9S,11S,12S,12αR,12βS)-12β-Acetoxy-9-((3-(4-(3,7-bis(dimethylamino)-5,5-dimethyldibenzo[b,e]silin-10(5H)-ylidene)butanamido)-2-hydroxy-3-phenylpropanoyl)oxy)-4,6,11-trihydroxy-4α,8,13,13-tetramethyl-5-oxo-2α,3,4,4α,5,6,9,10,11,12,12α,12β-dodecahydro-1H-7,11-methanocyclodeca[3,4]benzo[1,2-β]oxet-12-yl benzoate (53)

2a +

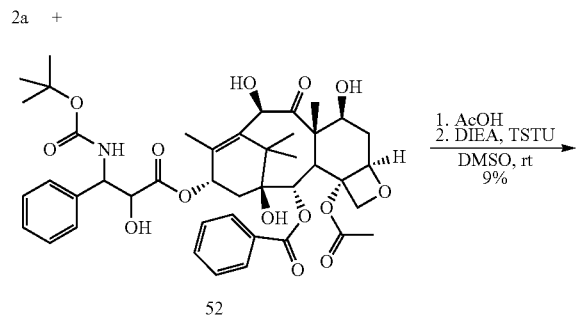

52

1. AcOH
2. DIEA, TSTU
DMSO, rt
9%

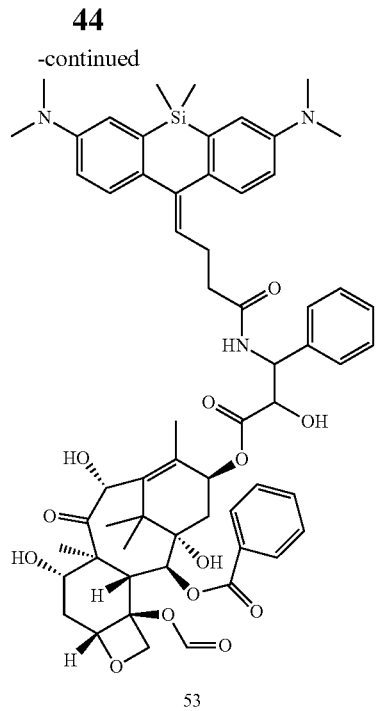

53

A solution of 2a (1.8 mg, 4.6 µmol, 1.0 eq.) in DMSO (130 µL) was treated with DIEA (2.3 µL, 13.8 µmol, 3.0 eq.) and TSTU (1.7 mg, 5.5 µmol, 1.2 eq.). The mixture was shaken for 20 min at room temperature. In a separate vial a solution of docetaxel (52) (20 mg, 25.2 µmol, 5.5 eq.) in formic acid (370 µL) was shaken for 45 min. The solution was evaporated, coevaporated with toluene (3×500 µL) and dried on the high vacuum for 1 h. The residue was taken up in DMSO (200 µL) and a quarter of this solution (50 µL, 6.3 µmol, 1.4 eq.) was added to the other mixture. The mixture was shaken for 1 h and then acidified with TFA (3 µL). RP-HPLC (3 mL/min, 10% to 90% B in 32 min) gave 53 (0.47 mg, 9%) as a light blue solid.

HRMS (ESI): m/z calcd for C$_{61}$H$_{74}$N$_3$O$_{13}$Si$^+$ [M+H]$^+$ 1084.4985, found 1084.5005; LCMS (LC, 10% to 90%): t$_R$=2.74 min.

8-(4-(3,7-Bis(dimethylamino)-5,5-dimethyldibenzo[b,e]silin-10(5H)-ylidene)butanamido)octanoic acid (55)

2a +

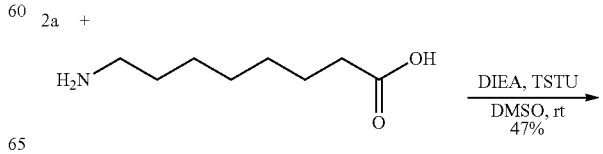

54

DIEA, TSTU
DMSO, rt
47%

-continued

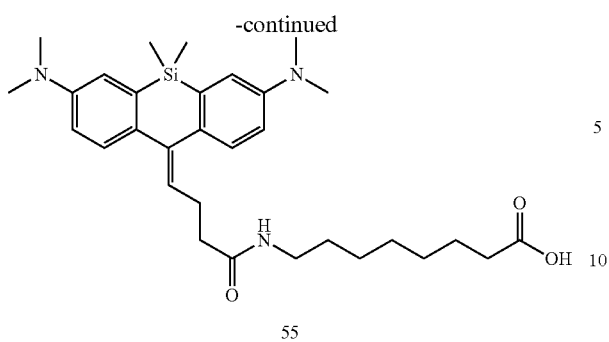

55

A solution of 2a (1.6 mg, 4.0 μmol, 1.0 eq.) in DMSO (120 μL) was treated with DIEA (4.6 μL, 28.0 μmol, 7.0 eq.) and TSTU (1.4 mg, 4.8 μmol, 1.2 eq.). The mixture was shaken for 20 min at room temperature. Amino-octanoic acid (54) (1.5 mg, 9.2 μmol, 2.3 eq.) was added to the mixture. The mixture was shaken for 10 min and then acidified with TFA (3 μL). RP-HPLC (3 mL/min, 10% to 90% B in 32 min) gave 55 (1.0 mg, 47%) as a blue solid.

HRMS (ESI): m/z calcd for $C_{31}H_{46}N_3O_3Si^+$ [M+H]$^+$ 536.3303, found 536.3293; LCMS (LC, 10% to 90%): $t_R$=2.92 min.

(2αR,4S,4αS,6R,9S,11S,12S,12αR,12βS)-12β-Acetoxy-9-((3-(8-(4-(3,7-bis(dimethylamino)-5,5-dimethyldibenzo[b,e]silin-10(5H)-ylidene)butanamido) octanamido)-2-hydroxy-3-phenylpropanoyl)oxy)-4, 6,11-trihydroxy-4α,8,13,13-tetramethyl-5-oxo-2α,3, 4,4α,5,6,9,10,11,12,12α,12β-dodecahydro-1H-7,11-methanocyclodeca[3,4]benzo[1,2-β]oxet-12-yl benzoate (56, PA-SiR-Tubulin)

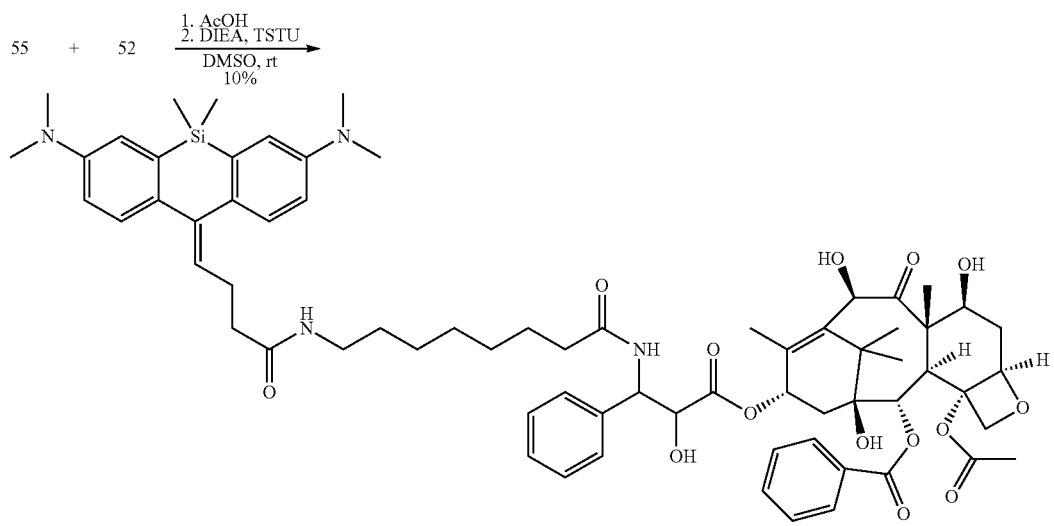

56

A solution of 55 (1.0 mg, 2.0 μmol, 1.0 eq.) in DMSO (120 ∞L) was treated with DIEA (1.0 μL, 6.0 μmol, 3.0 eq.) and TSTU (0.7 mg, 2.4 μmol, 1.2 eq.). The mixture was shaken for 20 min at room temperature. In a separate vial a solution of docetaxel (52) (20 mg, 25.2 μmol, 12.6 eq.) in formic acid (370 μL) was shaken for 45 min. The solution was evaporated, coevaporated with toluene (3×500 μL) and dried on the high vacuum for 1 h. The residue was taken up in DMSO (200 μL) and a tenth of this solution (20 μL, 2.5 μmol, 1.3 eq.) was added to the other mixture. The combined mixture was shaken for 1 h and then acidified with TFA (3 μL). RP-HPLC (3 mL/min, 10% to 90% B in 32 min) gave 56 (0.24 mg, 10%) as a blue solid.

HRMS (ESI): m/z calcd for $C_{69}H_{89}N_4O_{14}Si^+$ $[M+H]^+$ 1225.6139, found 1225.6103; LCMS (LC): $t_R$=3.72 min, 10% to 90% gradient.

4-(3,7-Bis(dimethylamino)-5,5-dimethyldibenzo[b,e]silin-10(5H)-ylidene)-N-(4-(6-methyl-1,2,4,5-tetrazin-3-yl)benzyl)butanamide (58)

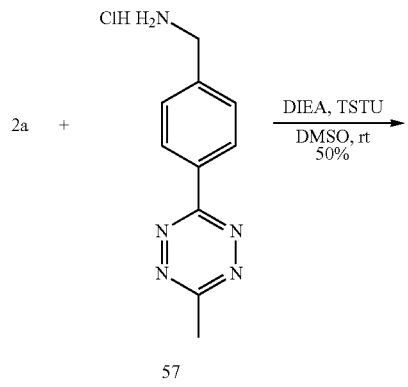

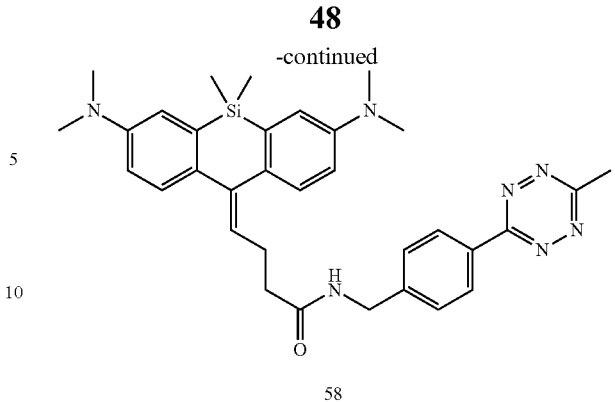

A solution of 2a (1.0 mg, 2.5 μmol, 1.0 eq.) in DMSO (120 μL) was treated with DIEA (2.1 μL, 12.5 μmol, 5.0 eq.) and TSTU (0.9 mg, 3.0 μmol, 1.2 eq.). The mixture was shaken for 20 min at room temperature. Me-Tetrazine-$NH_2 \cdot HCl$ (57) (0.7 mg, 3.0 μmol, 1.2 eq.) was added to the mixture. The mixture was shaken for 10 min and then acidified with TFA (3 μL). RP-HPLC (3 mL/min, 10% to 90% B in 32 min) gave 58 (0.70 mg, 50%) as a purple solid.

$^1$H NMR (400 MHz, $CD_3OD$) δ=0.41 (s, 6H), 2.46 (t, J=6.9 Hz, 2H), 2.78 (q, J=7.0 Hz, 2H), 3.04 (s, 3H), 3.13 (s, 6H), 3.22 (s, 6H), 4.42-4.50 (m, 2H), 5.96 (t, J=7.1 Hz, 1H), 7.17 (d, J=8.6 Hz, 1H), 7.35 (s, 2H), 7.39-7.44 (m, 2H), 7.42-7.50 (m, 2H), 7.56 (d, J=8.5 Hz, 1H), 8.28-8.34 (m, 2H), 8.60 ppm (t, J=6.0 Hz, 1H); HRMS (ESI): m/z calcd for $C_{33}H_{40}N_7OSi^+$ $[M+H]^+$ 578.3058, found 578.3051; LCMS (LC, 10% to 90%): $t_R$=3.31 min.

4-(3,7-Bis(dimethylamino)-5,5-diisopropyldibenzo[b,e]silin-10(5H)-ylidene)-N-(2-(2-((6-chlorohexyl)oxy)ethoxy)ethyl)butanamide (59)

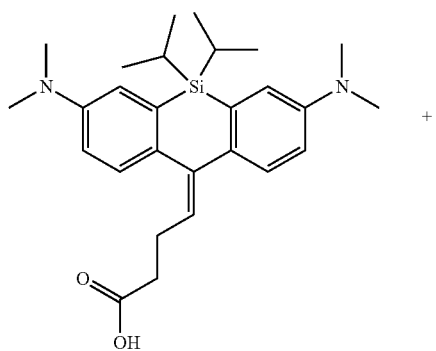

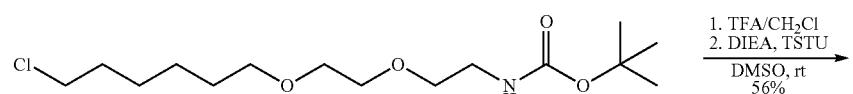

-continued

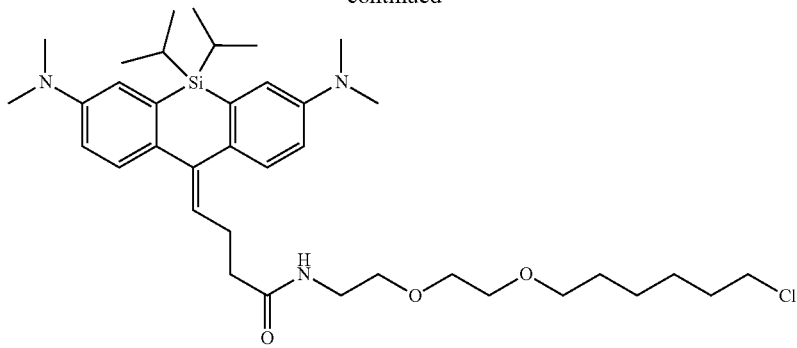

59

A solution of 6a (1.3 mg, 3.0 μmol, 1.0 eq.) in DMSO (150 μL) was treated with DIEA (1.5 μL, 9.0 μmol, 3.0 eq.) and TSTU (1.1 mg, 3.6 μmol, 1.2 eq.). The mixture was shaken for 20 min at room temperature. In a separate vial a solution of Halo-NHBoc 43 (1.3 mg, 4.0 μmol, 1.3 eq.) in CH₂Cl₂/TFA (8:2, 80 μL) was shaken for 3 min. The solution was evaporated and dried on the high vacuum for 1 h. The residue was taken up in DMSO (50 μL) and added to the other mixture. The mixture was shaken for 10 min and then acidified with TFA (3 μL). RP-HPLC (3 mL/min, 10% to 90% B in 32 min) gave 59 (1.02 mg, 55%) as a blue oil.

$^1$H NMR (400 MHz, CD$_3$CN) δ=1.03 (d, J=7.4 Hz, 12H), 1.29-1.44 (m, 4H), 1.48-1.57 (m, 4H), 1.69-1.76 (m, 2H), 2.19 (t, J=7.4 Hz, 2H), 2.51-2.63 (m, 2H), 3.03 (s, 6H), 3.04 (s, 6H), 3.23-3.31 (m, 2H), 3.37 (d, J=6.5 Hz, 2H), 3.42 (d, J=5.7 Hz, 2H), 3.48-3.53 (m, 4H), 3.56-3.61 (m, 2H), 5.72 (t, J=7.2 Hz, 1H), 6.43 (s, 1H), 7.04 (dd, J=8.5, 2.7 Hz, 1H), 7.14-7.22 (m, 1H), 7.26 (d, J=2.7 Hz, 1H), 7.33 (d, J=2.7 Hz, 1H), 7.41 (d, J=8.5 Hz, 1H), 7.51 ppm (d, J=8.6 Hz, 1H); HRMS (ESI): m/z calcd for C$_{37}$H$_{59}$ClN$_3$O$_3$Si$^+$ [M+H]$^+$ 656.4009, found 656.4009; LCMS (LC, 10% to 90%): t$_R$=5.09 min.

(9H-Fluoren-9-yl)methyl(21-chloro-8-oxo-3,6,12,15-tetraoxa-9-azahenicosyl)carbamate (61)

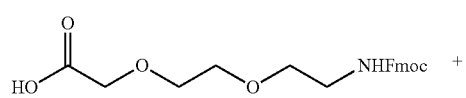

60

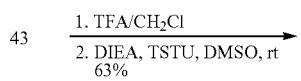

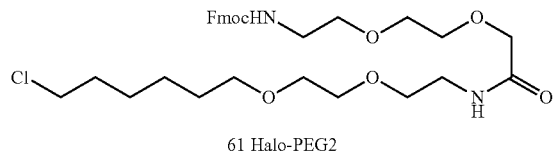

61 Halo-PEG2

A solution of Fmoc-N-PEG2-AcOH 60 (21.2 mg, 55.0 μmol, 1.1 eq.) in DMSO (625 μL) was treated with DIEA (41 μL, 250.0 μmol, 5.0 eq.) and TSTU (18.1 mg, 60.0 μmol, 1.2 eq.). The mixture was shaken for 20 min at room temperature. In a separate vial a solution of Halo-NHBoc 43 (16.2 mg, 50.0 μmol, 1.0 eq.) in CH₂Cl₂/TFA (8:2, 750 μL) was shaken for 5 min. The solution was evaporated and dried on the high vacuum for 1 h. The residue was taken up in DMSO (100 μL) and added to the other mixture. The mixture was shaken for 10 min and then acidified with TFA (20 μL). RP-HPLC (4 mL/min, 10% to 90% B in 32 min) gave Halo-PEG2 61 (19 mg, 63%) as a colourless oil.

$^1$H NMR (400 MHz, ACN-d$_3$) δ=1.23-1.34 (m, 2H), 1.34-1.42 (m, 2H), 1.43-1.54 (m, 2H), 1.61-1.78 (m, 2H), 3.26 (q, J=5.5 Hz, 2H), 3.27-3.40 (m, 4H), 3.39-3.47 (m, 4H), 3.46-3.52 (m, 4H), 3.52-3.64 (m, 6H), 3.89 (s, 2H), 4.22 (t, J=6.7 Hz, 1H), 4.37 (d, J=6.6 Hz, 2H), 5.90 (s, 1H), 7.16 (s, 1H), 7.33 (t, J=7.5 Hz, 2H), 7.41 (t, J=7.4 Hz, 2H), 7.65 (d, J=7.4 Hz, 2H), 7.83 ppm (d, J=7.5 Hz, 2H); $^{13}$C NMR (101 MHz, ACN-d$_3$) δ=26.10, 27.34, 30.23, 33.27, 39.19, 41.54, 46.17, 48.12, 66.69, 70.33, 70.56, 70.61, 70.64, 70.88, 70.95, 71.53, 71.71, 120.93, 126.01, 128.05, 128.60, 142.13, 145.22, 157.34, 170.79 ppm; HRMS (ESI): m/z calcd for C$_{31}$H$_{44}$ClN$_2$O$_7$$^+$ [M+H]$^+$ 591.2832, found 591.2831; LCMS (LC, 10% to 90%): t$_R$=3.42 min.

(9H-Fluoren-9-yl)methyl(28-chloro-15-oxo-3,6,9,12,19,22-hexaoxa-16-azaoctacosyl)carbamate (63)

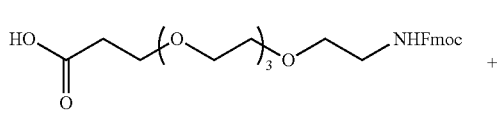

62

4-(3,7-Bis(dimethylamino)-5,5-diisopropyldibenzo[b,e]silin-10(5H)-ylidene)-N-(21-chloro-8-oxo-3,6,12,15-tetraoxa-9-azahenicosyl)butanamide (64)

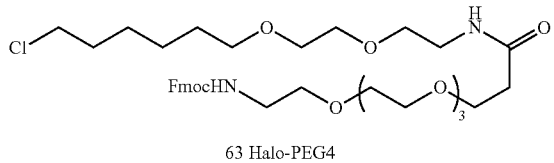

63 Halo-PEG4

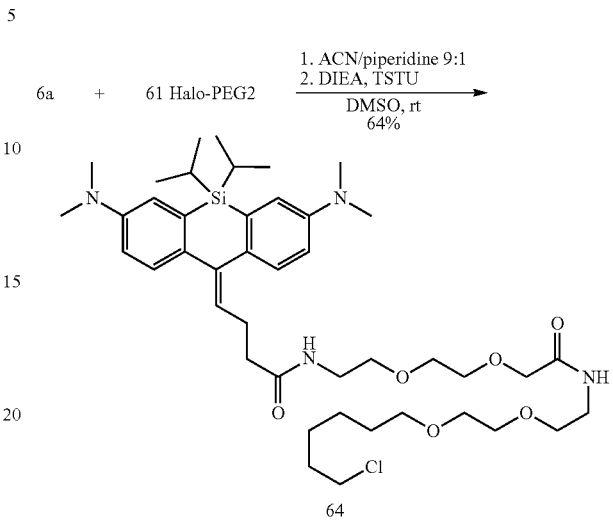

64

A solution of Fmoc-N-PEG4-CH₂-AcOH 62 (27.0 mg, 55.0 μmol, 1.1 eq.) in DMSO (625 μL) was treated with DIEA (41 μL, 250.0 μmol, 5.0 eq.) and TSTU (18.1 mg, 60.0 μmol, 1.2 eq.). The mixture was shaken for 20 min at room temperature. In a separate vial a solution of Halo-NHBoc 43 (16.2 mg, 50.0 μmol, 1.0 eq.) in CH₂Cl₂/TFA (8:2, 750 μL) was shaken for 5 min. The solution was evaporated and dried on the high vacuum for 1 h. The residue was taken up in DMSO (50 μL) and added to the other mixture. The mixture was shaken for 10 min and then acidified with TFA (20 μL). RP-HPLC (4 mL/min, 10% to 90% B in 32 min) gave Halo-PEG4 63 (19 mg, 55%) as colourless oil.

¹H NMR (400 MHz, ACN-d₃) δ=1.27-1.45 (m, 4H), 1.46-1.58 (m, 2H), 1.68-1.80 (m, 2H), 2.34 (t, J=6.1 Hz, 2H), 3.23 (q, J=5.5 Hz, 2H), 3.29 (q, J=5.6 Hz, 2H), 3.39 (t, J=6.6 Hz, 2H), 3.44-3.58 (m, 22H), 3.63 (t, J=6.1 Hz, 2H), 4.23 (t, J=6.8 Hz, 1H), 4.35 (d, J=6.8 Hz, 2H), 5.80 (s, 1H), 6.69 (s, 1H), 7.34 (td, J=7.4, 1.1 Hz, 2H), 7.42 (t, J=7.4 Hz, 2H), 7.66 (d, J=7.5 Hz, 2H), 7.83 ppm (d, J=7.5 Hz, 2H); ¹³C NMR (101 MHz, ACN-d₃) δ=26.13, 27.34, 30.27, 33.28, 37.32, 39.85, 41.52, 46.18, 48.12, 66.78, 67.82, 70.19, 70.37, 70.70, 70.91, 70.94, 70.97, 71.07, 71.13, 71.57, 120.93, 126.06, 128.06, 128.62, 142.12, 145.21, 157.29, 171.97 ppm; HRMS (ESI): m/z calcd for $C_{36}H_{54}ClN_2O_9^+$ [M+H]⁺ 693.3512, found 693.3514; LCMS (LC, 10% to 90%): $t_R$=4.19 min.

A solution of 6a (1.1 mg, 2.5 μmol, 1.0 eq.) in DMSO (120 μL) was treated with DIEA (2 μL, 12.5 μmol, 5.0 eq.) and TSTU (0.9 mg, 3.0 μmol, 1.2 eq.). The mixture was shaken for 20 min at room temperature. In a separate vial a solution of Halo-PEG2 61 (1.8 mg, 3.0 μmol, 1.2 eq.) in ACN/piperidine (9:1, 100 μL) was shaken for 15 min. The solution was evaporated and dried on the high vacuum for 1 h. The residue was taken up in DMSO (50 μL) and added to the other mixture. The mixture was shaken for 10 min and then acidified with TFA (3 μL). RP-HPLC (3 mL/min, 10% to 100% B in 32 min) gave 64 (1.29 mg, 64%) as a blue oil.

HRMS (ESI): m/z calcd for $C_{43}H_{70}ClN_4O_6Si^+$ [M+H]⁺ 801.4748, found 801.4742; LCMS (LC, 10% to 90%): $t_R$=4.05 min.

1-(4-(3,7-Bis(dimethylamino)-5,5-diisopropyldibenzo[b,e]silin-10(5H)-ylidene)butanamido)-N-(2-(2-((6-chlorohexyl)oxy)ethoxy)ethyl)-3,6,9,12-tetraoxapentadecan-15-amide (65)

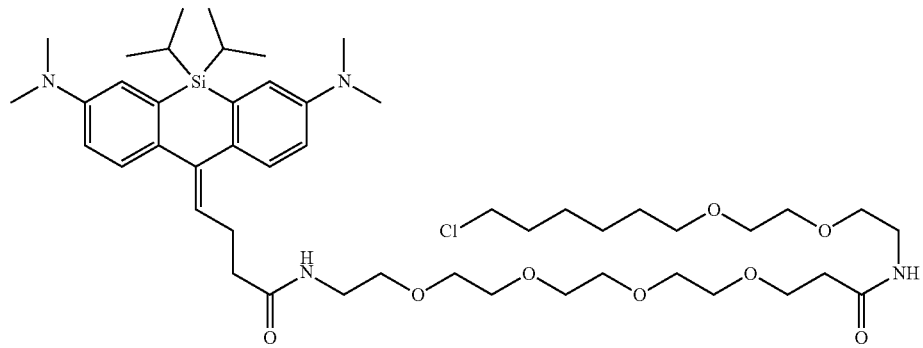

65

A solution of 6a (1.1 mg, 2.5 µmol, 1.0 eq.) in DMSO (120 µL) was treated with DIEA (2 µL, 12.5 µmol, 5.0 eq.) and TSTU (0.9 mg, 3.0 µmol, 1.2 eq.). The mixture was shaken for 20 min at room temperature. In a separate vial a solution of Halo-PEG4 63 (1.8 mg, 3.0 µmol, 1.2 eq.) in ACN/piperidine (9:1, 100 µL) was shaken for 15 min. The solution was evaporated and dried on the high vacuum for 1 h. The residue was taken up in DMSO (50 µL) and added to the other mixture. The mixture was shaken for 10 min and then acidified with TFA (3 µL). RP-HPLC (3 mL/min, 10% to 100% B in 32 min) gave 65 (0.48 mg, 21%) as a blue oil.

HRMS (ESI): m/z calcd for $C_{48}H_{80}ClN_4O_8Si^+$ [M+H]$^+$ 903.5428, found 903.5424; LCMS (LC, 10% to 90%): $t_R$=4.37 min.

N-(4-(((2-Amino-9H-purin-6-yl)oxy)methyl)benzyl)-4-(3,7-bis(dimethylamino)-5,5-diisopropyldibenzo[b,e]silin-10(5H)-ylidene)butanamide (66)

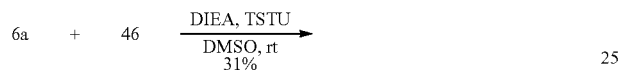

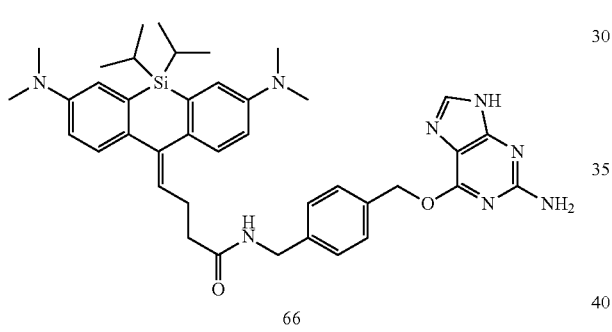

A solution of 6a (1.5 mg, 3.3 µmol, 1.0 eq.) in DMSO (150 µl) was treated with DIEA (1.6 µL, 9.9 µmol, 3.0 eq.) and TSTU (1.2 mg, 4.0 µmol, 1.2 eq.) was shaken for 20 min. BG-NH$_2$ 46 (1.1 mg, 4.0 µmol, 1.2 eq.) was added. The mixture was shaken for 10 min at room temperature and acidified with TFA (2 µL). RP-HPLC (3 mL/min, 10% to 90% B in 32 min) gave 66 (0.73 mg, 31%) as a light blue solid.

$^1$H NMR (400 MHz, DMSO-d$_6$) δ=0.99 (d, J=7.4 Hz, 12H), 1.37-1.53 (m, 2H), 2.20 (t, J=7.5 Hz, 2H), 2.52-2.59 (m, 2H), 2.93 (s, 6H), 2.95 (s, 6H), 4.23 (d, J=5.7 Hz, 2H), 5.50 (s, 2H), 5.59 (t, J=7.0 Hz, 1H), 6.85 (d, J=8.6 Hz, 1H), 6.90 (d, J=8.2 Hz, 1H), 6.99 (s, 2H), 7.21-7.32 (m, 3H), 7.35 (d, J=8.6 Hz, 1H), 7.45 (d, J=7.8 Hz, 2H), 8.38 (t, J=5.9 Hz, 1H), 8.43-8.47 ppm (m, 1H); HRMS (ESI): m/z calcd for $C_{40}H_{51}N_8O_2Si^+$ [M+H]$^+$ 703.3899, found 703.3901; LCMS (LC, 10% to 90%): $t_R$=3.44 min.

2-Amino-3-((4-(((2-amino-9H-purin-6-yl)oxy)methyl)benzyl)amino)-3-oxopropane-1-sulfonic acid (68)

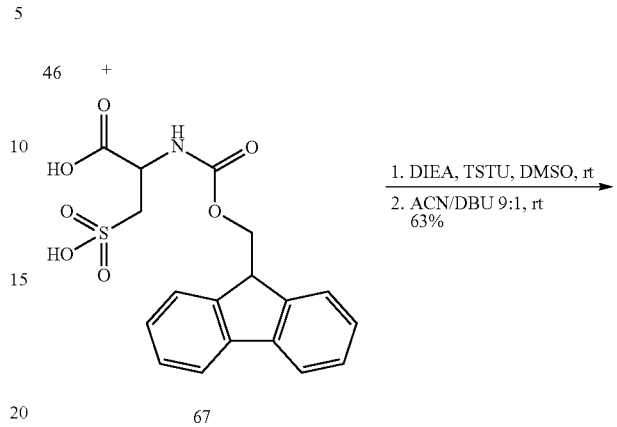

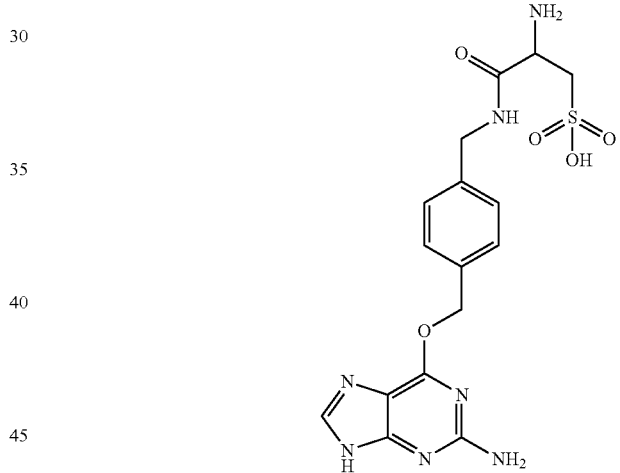

A solution of Fmoc-cysteic-acid (67) (8.6 mg, 22.0 µmol, 1.1 eq.) in DMSO (250 µl) was treated with DIEA (165 µL, 100.0 µmol, 5.0 eq.) and TSTU (7.2 mg, 24.0 µmol, 1.2 eq.) was shaken for 20 min. BG-NH$_2$ 46 (5.4 mg, 20.0 µmol, 1.0 eq.) was added and the mixture was shaken for 45 min at room temperature. The mixture was poured into Et$_2$O (2 mL) and the precipitate was washed with Et$_2$O (2×1 mL). The solid was redissolved in ACN/DBU 9:1 (500 µL) and shaken for 10 min. The mixture was acidified with TFA (2 µL) and diluted with water and DMSO. RP-HPLC (4 mL/min, 10% to 70% B in 32 min) gave 68 (5 mg, 62%) as a light blue solid.

HRMS (ESI): m/z calcd for $C_{16}H_{20}N_7O_5S^+$ [M+H]$^+$ 422.1241, found 422.1241; LCMS (LC, 10% to 90%): $t_R$=0.73 min.

3-((4-(((2-Amino-9H-purin-6-yl)oxy)methyl)benzyl) amino)-2-(4-(3,7-bis(dimethylamino)-5,5-diisopropyldibenzo[b,e]silin-10(5H)-ylidene)butanamido)-3-oxopropane-1-sulfonic acid (69)

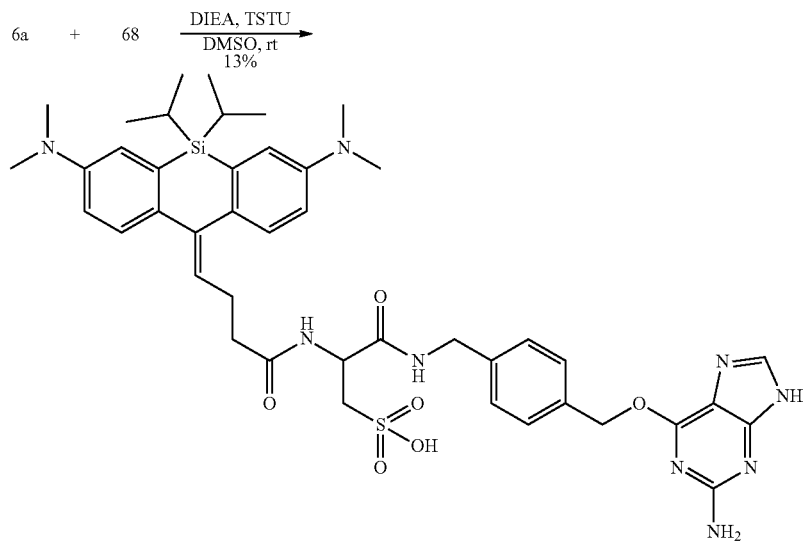

69

A solution of 6a (1.1 mg, 2.5 μmol, 1.0 eq.) in DMSO (120 μl) was treated with DIEA (24 μL, 150.0 μmol, 60.0 eq.) and TSTU (0.9 mg, 3.0 μmol, 1.2 eq.) was shaken for 10 min. 68 (1.2 mg, 3.0 μmol, 1.2 eq.) was added. The mixture was shaken for 10 min at room temperature and then acidified with TFA (20 μL). RP-HPLC (3 mL/min, 10% to 90% B in 32 min) gave 69 (0.27 mg, 13%) as a light blue solid.

HRMS (ESI): m/z calcd for $C_{43}H_{56}N_9O_6SSi^+$ $[M+H]^+$ 854.3838, found 854.3823; LCMS (LC, 10% to 90%): $t_R$=2.64 min.

N-(4-((4R,7R,10S,13S,19S,E)-7-((1H-Indol-2-yl)methyl)-4-(4-hydroxyphenyl)-8,13,15,19-tetramethyl-2,6,9,12-tetraoxo-1-oxa-5,8,11-triazacyclononadec-15-en-10-yl)butyl)-4-(3,7-bis(dimethylamino)-5,5-diisopropyldibenzo[b,e]silin-10(5H)-ylidene)butanamide (70)

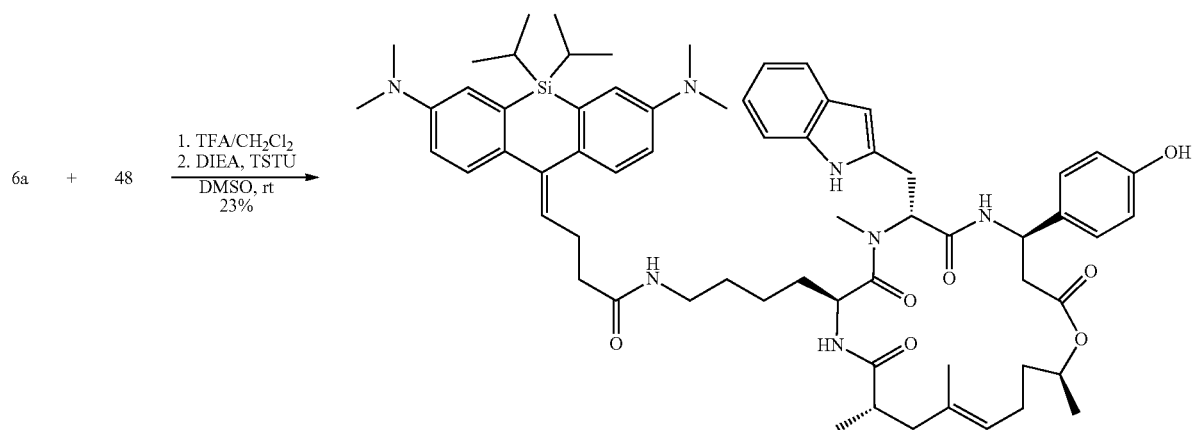

70

A solution of 6a (1.3 mg, 3.0 µmol, 1.0 eq.) in DMSO (150 µL) was treated with DIEA (1.5 µL, 9.0 µmol, 3.0 eq.) and TSTU (1.1 mg, 3.6 µmol, 1.2 eq.). The mixture was shaken for 20 min at room temperature. In a separate vial a solution of jasplakinolide-NHBoc 48 (2.8 mg, 3.6 µmol, 1.2 eq.) in CH$_2$Cl$_2$/TFA (8:2, 80 µL) was shaken for 3 min. The solution was evaporated and dried on the high vacuum for 1 h. The residue was taken up in DMSO (50 µL) and added to the other mixture. The mixture was shaken for 10 min and then acidified with TFA (3 µL). RP-HPLC (3 mL/min, 0% to 90% B in 32 min) gave 70 (0.75 mg, 23%) as a light blue solid.

$^1$H NMR (400 MHz, CD$_3$CN) δ=0.95-1.02 (m, 4H), 1.00-1.09 (m, 13H), 1.11 (d, J=6.3 Hz, 4H), 1.27-1.39 (m, 4H), 1.48-1.62 (m, 2H), 1.78-1.89 (m, 5H), 2.20-2.34 (m, 4H), 2.40-2.52 (m, 2H), 2.62-2.71 (m, 3H), 2.71-2.88 (m, 2H), 2.95 (s, 3H), 3.04 (s, 6H), 3.09 (s, 6H), 3.20 (s, 3H), 4.69 (q, J=5.9 Hz, 1H), 4.74-4.80 (m, 1H), 4.96 (t, J=6.9 Hz, 1H), 5.10-5.19 (m, 1H), 5.54 (dt, J=10.1, 5.0 Hz, 1H), 5.82 (t, J=7.3 Hz, 1H), 6.59 (d, J=6.9 Hz, 2H), 6.76 (d, J=6.5 Hz, 2H), 6.98-7.05 (m, 4H), 7.09-7.11 (m, 2H), 7.28-7.40 (m, 4H), 7.44-7.54 (m, 2H), 7.59 (dd, J=13.1, 8.2 Hz, 2H), 8.35-8.53 (m, 1H), 10.11 ppm (s, 1H); HRMS (ESI): m/z calcd for C$_{65}$H$_{88}$N$_7$O$_7$Si$^+$ [M+H]$^+$ 1106.6509, found 1106.6520; LCMS (LC, 10% to 90%): t$_R$=4.86 min.

N-(4-(((2-Amino-9H-purin-6-yl)oxy)methyl)benzyl)-4-(3,7-bis(dimethylamino)-2,8-difluoro-5,5-dimethyldibenzo[b,e]silin-10(5H)-ylidene)butanamide (71)

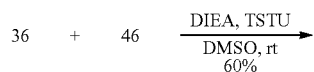

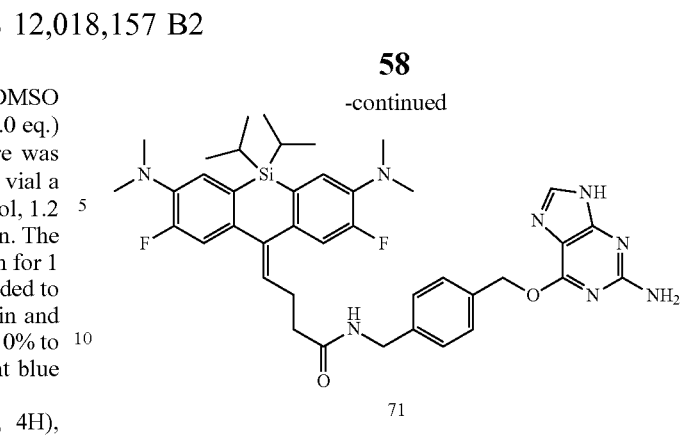

71

A solution of 36 (1.2 mg, 2.7 µmol, 1.0 eq.) in DMSO (120 µl) was treated with DIEA (1.3 µL, 8.1 µmol, 3.0 eq.) and TSTU (1.0 mg, 3.2 µmol, 1.2 eq.) was shaken for 20 min. BG-NH$_2$ 46 (0.9 mg, 3.2 µmol, 1.2 eq.) was added. The mixture was shaken for 10 min at room temperature and then acidified with TFA (2 µL). RP-HPLC (3 mL/min, 10% to 90% B in 32 min) gave 71 (1.1 mg, 60%) as a white solid.

$^1$H NMR (400 MHz, CD$_3$OD) δ=0.40 (s, 6H), 2.35-2.45 (m, 2H), 2.72 (t, J=7.1 Hz, 2H), 2.93 (s, 6H), 2.94 (s, 6H), 4.37 (d, J=4.3 Hz, 2H), 5.60 (s, 2H), 5.87 (t, J=7.2 Hz, 1H), 7.18 (d, J=9.8 Hz, 1H), 7.22 (d, J=10.0 Hz, 1H), 7.25-7.33 (m, 4H), 7.34-7.42 (m, 2H), 8.34 (s, 1H), 8.52 ppm (t, J=6.0 Hz, 1H); $^{19}$F NMR (376 MHz, CD$_3$OD) δ=-123.44--123.20 (m), -123.13--122.77 ppm (m); HRMS (ESI): m/z calcd for C$_{36}$H$_{41}$F$_2$N$_8$O$_2$Si$^+$ [M+H]$^+$ 683.3084, found 683.3082; LCMS (LC, 10% to 90%): t$_R$=3.50 min.

N-(4-((4R,7R,10S,13S,19S,E)-7-((1H-Indol-2-yl)methyl)-4-(4-hydroxyphenyl)-8,13,15,19-tetramethyl-2,6,9,12-tetraoxo-1-oxa-5,8,11-triazacyclononadec-15-en-10-yl)butyl)-4-(3,7-bis(dimethylamino)-2,8-difluoro-5,5-dimethyldibenzo[b,e]silin-10(5H)-ylidene)butanamide (72)

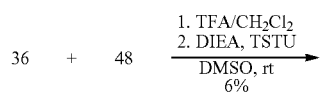

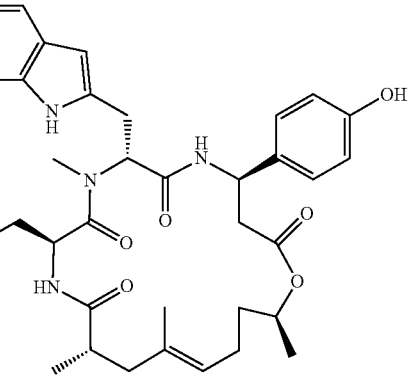

72

A solution of 36 (1.3 mg, 3.0 µmol, 1.0 eq.) in DMSO (120 µL) was treated with DIEA (1.5 µL, 9.0 µmol, 3.0 eq.) and TSTU (1.1 mg, 3.6 µmol, 1.2 eq.). The mixture was shaken for 20 min at room temperature. In a separate vial a solution of jasplakinolide-NHBoc 48 (2.8 mg, 3.6 µmol, 1.2 eq.) in CH$_2$Cl$_2$/TFA (8:2, 80 µL) was shaken for 2 min. The solution was evaporated and dried on the high vacuum for 1 h. The residue was taken up in DMSO (50 µL) and added to the other mixture. The mixture was shaken for 10 min and then acidified with TFA (3 µL). RP-HPLC (3 mL/min, 10% to 90% B in 32 min) gave 72 (0.22 mg, 6%) as a white solid.

$^1$H NMR (400 MHz, CD$_3$OD) δ=0.46 (s, 6H), 0.73-1.01 (m, 4H), 1.05 (d, J=6.8 Hz, 3H), 1.16 (d, J=6.3 Hz, 3H), 1.18-1.26 (m, 1H), 1.29 (s, 3H), 1.29-1.47 (m, 2H), 1.50-1.71 (m, 5H), 1.81-1.94 (m, 3H), 2.34 (q, J=7.0 Hz, 2H), 2.59 (ddd, J=10.4, 6.9, 3.0 Hz, 1H), 2.70 (dd, J=8.9, 5.1 Hz, 3H), 2.80-3.01 (m, 2H), 3.03 (d, J=1.2 Hz, 9H), 3.08 (s, 6H), 4.70 (t, J=5.7 Hz, 1H), 4.78-4.84 (m, 1H), 5.02 (t, J=7.0 Hz, 1H), 5.24 (td, J=9.1, 4.0 Hz, 1H), 5.56-5.66 (m, 1H), 5.93 (t, J=7.3 Hz, 1H), 6.69-6.75 (m, 2H), 6.93-7.03 (m, 3H), 7.03-7.09 (m, 2H), 7.24-7.39 (m, 3H), 7.46 (dd, J=11.2, 9.3 Hz, 2H), 7.56-7.63 (m, 1H), 8.39 ppm (d, J=8.5 Hz, 1H); HRMS (ESI): m/z calcd for $C_{61}H_{78}F_2N_7O_7Si^+$ $[M+H]^+$ 1086.5695, found 1086.5704; LCMS (LC, 10% to 90%): $t_R$=4.85 min.

Abbreviations

ACN, acetonitrile; NBS, N-bromosuccinimide; PBS, phosphate buffered saline; secBuLi secondary butyl lithium;

The invention claimed is:
1. A compound characterized by general formula (100):

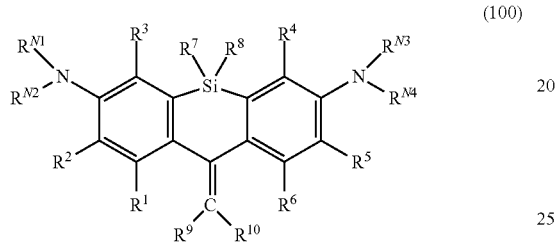

(100)

wherein
$R^1$ and $R^6$ are independently selected from hydrogen and fluorine;
$R^2$, $R^3$, $R^4$ and $R^5$ independently of each other is selected from H, halogen, $SO_3H$, $CO_2H$, $NO_2$, $CO_2R$, $SO_2R$, with R being selected from $C_1$ to $C_4$ unsubstituted alkyl, and an unsubstituted or substituted moiety selected from $C_1$-$C_{20}$ alkyl, $C_3$-$C_8$ cycloalkyl, $C_1$-$C_{20}$ alkoxy, $C_2$-$C_{20}$ alkenyl, $C_2$-$C_{20}$ alkynyl, $C_7$-$C_{20}$ alkylaryl, phenyl and 5- or 6-membered ring heteroaryl, or a combination thereof;
$R^7$ and $R^8$ are independently selected from:
unsubstituted and substituted $C_1$-$C_{12}$ alkyl, $C_3$-$C_8$ cycloalkyl, $C_2$-$C_{12}$ alkylene, $C_2$-$C_{12}$ alkylyne and $C_7$-$C_{12}$ alkylaryl; and
unsubstituted or substituted 5- or 6-ring aryl,
$R^{N1}$, $R^{N2}$, $R^{N3}$ and $R^{N4}$ are:
independently selected from H, unsubstituted and substituted $C_1$-$C_8$ alkyl, $C_3$-$C_8$ cycloalkyl, $C_1$-$C_4$ acyl, and $C_7$-$C_{12}$ alkylaryl, and unsubstituted phenyl or phenyl substituted by COOH—, COOR, $CONR_2$, unsubstituted alkyl, halogen, O-alkyl, and $NO_2$; or
$R^{N1}$ together with $R^{N2}$, and/or $R^{N3}$ together with $R^{N4}$ are a $C_3$, alkyl, $C_4$ alkyl, or $C_6$ unsubstituted or substituted alkyl forming a 3-7 sized ring structure; or
$R^{N1}$ and/or $R^{N3}$ are independently selected from H and unsubstituted and substituted $C_1$-$C_8$ alkyl, $C_3$-$C_8$ cycloalkyl, and $C_7$-$C_{12}$ alkylaryl, and $R^{N2}$ together with $R^2$ or $R^3$, and/or $R^{N4}$ together with $R^4$ or $R^5$, is an unsubstituted or substituted $C_2$ alkyl, $C_3$ alkyl, or $C_4$ alkyl, or an unsubstituted or substituted $C_2$ alkyl $C_3$ alkyl or $C_4$ N-, O-, S-, or Se-alkyl;
one of $R^9$ and $R^{10}$ is hydrogen and the other one is hydrogen or a saturated carbon atom connected to a moiety selected from H, halogen, $SO_3H$, $CO_2H$, $NO_2$, $CO_2R$, $SO_2R$, with R being selected from $C_1$ to $C_4$ unsubstituted alkyl, and an unsubstituted or substituted moiety selected from $C_1$-$C_{20}$ alkyl, $C_3$-$C_8$ cycloalkyl, $C_1$-$C_{20}$ alkoxy, $C_2$-$C_{20}$ alkenyl, $C_2$-$C_{20}$ alkynyl, $C_7$-$C_{20}$ alkylaryl, phenyl and 5- or 6-membered ring heteroaryl, or a combination thereof; and wherein optionally the compound is covalently linked to a binding moiety M via any of the substituents.

2. The compound according to claim 1, wherein the compound is covalently linked to a binding moiety M selected from:
a. a moiety selectively attachable by covalent bond to a protein or nucleic acid under conditions prevailing in cell culture or inside of a living cell, or from
b. a substrate of $O^6$-alkylguanine-DNA-alkyltransferase, selected from a 6-[(4-methylenephenyl)methoxy]-9H-purin-2-amine moiety of formula (110), a pyrimidine derivative of formula (111) or (112),

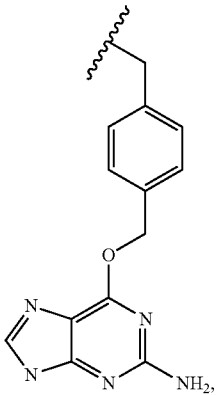

(110)

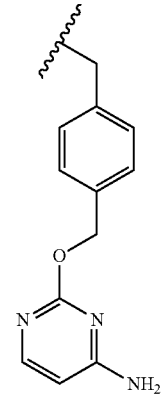

(111)

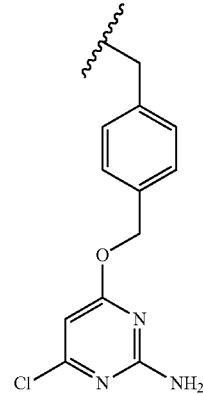

(112)

c. a substrate of a haloalkane halotransferase, or from
d. a substrate of dihydrofolate reductase,
e. a moiety capable of selectively interacting non-covalently with a biomolecule under conditions prevailing in a live cell, wherein said moiety and said biomolecule form a complex having a dissociation constant $k_D$ of $10^{-6}$ mold or less
f. a lipid selected from a ceramide derivative, a glyceride, or a fatty acid.

3. The compound according to claim 1, wherein any one of substituents $R^2$, $R^3$, $R^4$, $R^5$, and one of $R^9$ and $R^{10}$ independently of any other is H or a moiety having a molecular weight between 15 and 1500 u (g/mol).

4. The compound according to claim 3, wherein said moiety having a molecular weight between 15 and 1500 u is characterized by a general formula —L-M, wherein L is a linker covalently connecting the compound to the binding moiety M as defined above, and L is a covalent bond or a linker consisting of 1 to 50 atoms having an atomic weight of 12 or higher.

5. The compound according to claim 4, wherein L is -$L^{A1}$-$L^{J1}$-$L^{A2}_m$-$L^{J2}_{m'}$-$L^{A3}_p$-, wherein
$L^{A1}$, $L^{A2}$ and $L^{A3}$ are independently selected from $C_1$ to $C_6$ unsubstituted, amino-, hydroxyl-, carboxyl- or fluoro substituted alkyl or cycloalkyl, and $(CH_2-CH_2-O)_r$ or $(CH_2-CH(OH)-CH_2-O)_r$ with r being an integer from 1 to 4, and
$L^{J1}$ and $L^{J2}$ are selected independently from —$NR^5C(O)$—, —$C(O)N(R^5)$—, —CN—, —NC—, —CO—, —OC(O)—, —C(O)O—, $NR^{N5}$—, —O—, and —S—, wherein $R^{N5}$— is H and unsubstituted $C_1$ and $C_6$ alkyl or amino-, hydroxyl-, carboxyl or fluoro substituted $C_1$ to $C_6$ alkyl and
m, m' and p independently from each other are selected from 0 and 1.

6. The compound according to claim 1, wherein $R^7$ and $R^8$ are independently selected from
unsubstituted alkyl, alkenyl or alkynyl; or hydroxyl-, amino- or halogen-substituted $C_1$ to $C_4$ alkyl, alkenyl or alkynyl,
unsubstituted $C_3$ to $C_6$ cycloalkyl; or hydroxyl-, amino- or halogen- substituted $C_3$ to $C_6$ cycloalkyl or
unsubstituted phenyl or hydroxyl-, alkyoxy-, amino- or halogen-substituted phenyl.

7. The compound according to claim 1, wherein
a. $R^{N1}$ and $R^{N2}$, and/or $R^{N3}$ and $R^{N4}$, are independently selected from H, unsubstituted $C_1$-$C_6$ alkyl, $C_1$-$C_4$ acyl, and $C_3$-$C_6$ cycloalkyl; and amino-, hydroxy-, carboxy- and/or fluoro-substituted $C_1$-$C_6$ alkyl, $C_1$-$C_4$ acyl, and $C_3$-$C_6$ cycloalkyl,
b. $R^{N1}$ together with $R^{N2}$, and/or $R^{N3}$ together with $R^{N4}$ together are an unsubstituted $C_3$-$C_6$ alkyl; or alkyl-, amino-, hydroxy-, carboxy- and fluoro-substituted $C_3$-$C_6$ alkyl;
c. $R^{N1}$ and/or $R^{N3}$ are independently selected from H, unsubstituted and alkyl-, amino-, hydroxy-, carboxy- and fluoro-substituted $C_1$-$C_6$ alkyl, $C_1$-$C_4$ acyl, and $C_3$-$C_6$ cycloalkyl, and $R^{N2}$ together with $R^2$ or $R^3$, and/or $R^{N4}$ together with $R^4$ or $R^5$, is an alkyl or heteroalkyl bridge selected from —$(CH_2)_2$—, —$(CH_2)_3$—, —$CH_2CH=CH$— or —$(CH_2)_4$— or —$CH_2$—O—, —$CH_2$—$NR^5$—, —$CH_2$—S—, —$CH_2$—Se—, —$(CH_2)_2O$—, —$(CH_2)_2NR^N$—, —$(CH_2)_2S$—, —$(CH_2)_2Se$—, —$CH_2$—O—$CH_2$—, —$CH_2NR^5$—, —$CH_2S$—$CH_2$—, —$CH_2$—Se—$CH_2$—, —$CH_2$-(1,2)phenyl-, and a mono- or dimethyl substituted derivative of any one of the foregoing alkyl or heteroalkyl bridge moieties;
d. $R^{N1}$ and/or $R^{N3}$ are independently selected from H, unsubstituted and alkyl-, amino-, hydroxy-, carboxy- and fluoro-substituted $C_1$-$C_6$ alkyl, $C_1$-$C_4$ acyl, and $C_3$-$C_6$ cycloalkyl, and $R^{N2}$ together with $R^2$, and/or $R^{N4}$ together with $R^5$, form an annular structure according to any one of substructures (101) to (104) or (101') to (104'):

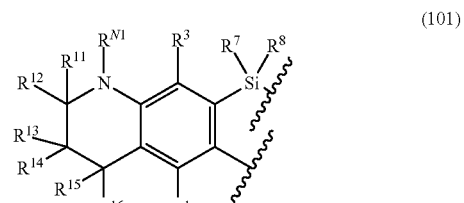

(101)

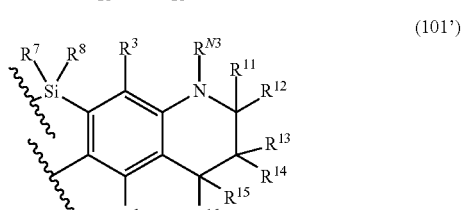

(101')

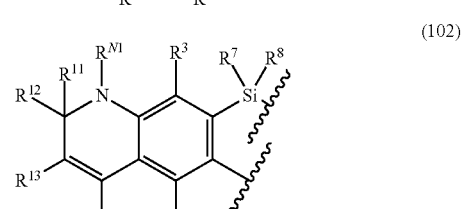

(102)

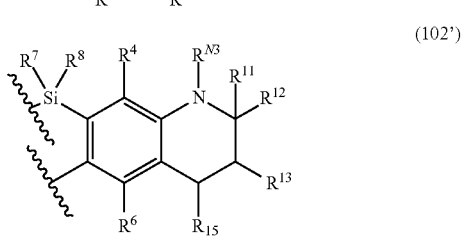

(102')

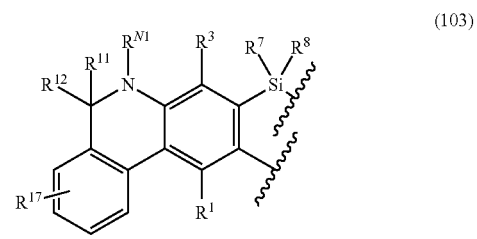

(103)

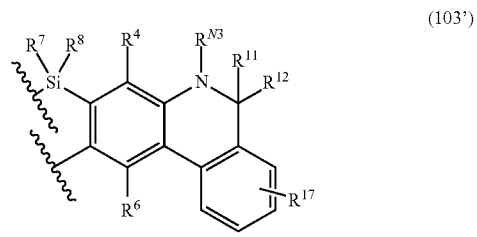

(103')

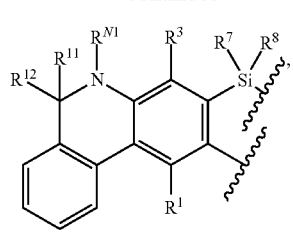

(104)

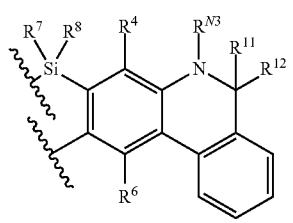

(104')

wherein $R^{11}$, $R^{12}$, $R^{13}$, $R^{14}$, $R^{15}$ and $R^{16}$ are selected from H, unsubstituted or hydroxyl-, amino-, carboxyl-, sulfoxyl- or halogen-substituted $C_1$ to $C_4$ alkyl, halogen, $SO_3R$, COOR', CONR'$_2$ with R selected from H and unsubstituted $C_1$ to $C_4$ alkyl;

and $R^{17}$ is selected from H and unsubstituted or hydroxyl-, amino-, carboxyl-, sulfoxyl- or halogen-substituted $C_1$ to $C_4$ alkyl, halogen, $NO_2$, CN, $SO_3R$, COOR', CONR'$_2$ with R selected from H and unsubstituted $C_1$ to $C_4$ alkyl;

and $R^1$, $R^3$, $R^7$ and $R^8$ can have any of the meanings given herein; or e. $R^{N1}$ together with $R^3$, and $R^{N2}$ together with $R^2$, and/or $R^{N3}$ together with $R^4$, and $R^{N4}$ together with $R^5$, form a bi-annular structure according to any one of substructures (105) to (107) and/or (105') to (107'):

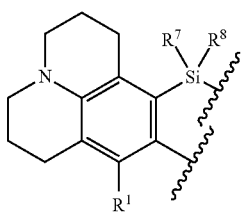

(105)

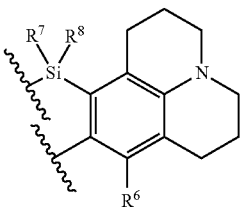

(105')

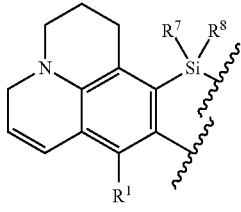

(106)

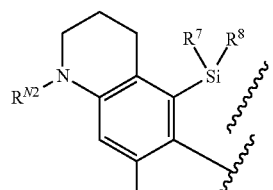

(106')

(107)

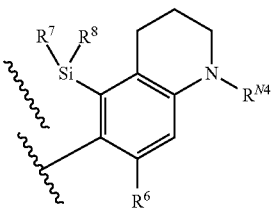

(107')

wherein $R^{11}$, $R^{12}$, $R^{13}$, and $R^{15}$ are selected from H, unsubstituted or hydroxyl-, amino-, carboxyl-, sulfoxyl- or halogen-substituted $C_1$ to $C_4$ alkyl, halogen, $SO_3R$, COOR', CONR'$_2$ with R selected from H and unsubstituted $C_1$ to $C_4$ alkyl;

and $R^1$, $R^3$, $R^7$ and $R^8$ can have any of the meanings given herein; or f. $R^{N2}$ and/or $R^{N4}$ are independently selected from H, unsubstituted and alkyl-, amino-, hydroxy-, carboxy-fluoro-substituted $C_1$-$C_6$ alkyl, $C_1$-$C_4$ acyl, and $C_3$-$C_6$ cycloalkyl, and $R^{N1}$ together with $R^3$, and/or $R^{N3}$ together with $R^4$, form an annular structure according to any one of substructures (108) to (109) and/or (108') to (109'):

(108)

(108')

-continued

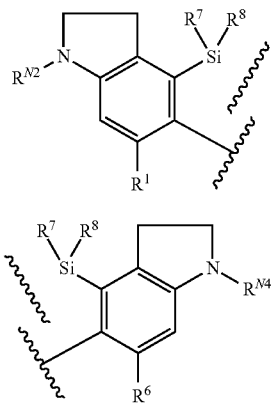
(109)

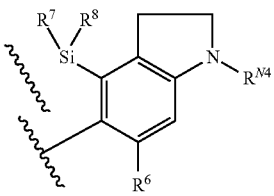
(109')

wherein $R^1$, $R^3$, $R^4$, $R^6$, $R^7$ and $R^8$ can have any of the meanings given herein.

8. The compound according to claim 7, wherein $R^{N1}$ together with $R^{N2}$, and/or $R^{N3}$ together with $R^{N4}$ together are —$(CH_2)_3$—, —$CH_2CHFCH_2$—, —$CH_2CF_2CH_2$—, —$CH_2CH(CH_3)CH_2$—, —$CH_2C(CH_3)_2CH_2$—, $CH_2CH(CN)CH_2$—, $CH_2CH(COOH)CH_2$—, $CH_2CH(CH_2COOH)CH_2$—, —$CH_2CH(OCH_3)CH_2$— and —$CH_2CH(N(CH_3)_2)CH_2$—.

9. The compound according to claim 1, wherein
$R^1$, $R^6$ and $R^9$ are H, and/or
$R^2$, $R^3$, $R^4$ and $R^5$ are selected from H, halogen, $SO_3H$, and unsubstituted and amino-, hydroxy-, carboxy-, $SO_3H$—, halogen-substituted $C_1$-$C_4$ alkyl, $CO_2H$, $CO_2R$, $SO_2R$ with R being selected from $C_1$ to $C_4$ unsubstituted alkyl, and/or
$R^7$ and $R^8$ are independently selected from unsubstituted or halogen-substituted $C_1$ to $C_4$ alkyl or $C_3$ to $C_6$ cycloalkyl and phenyl, and
$R^{N1}$, $R^{N2}$, $R^{N3}$ and $R^{N4}$ are individually unsubstituted $C_1$ to $C_4$ alkyl or $C_3$ to $C_6$ cycloalkyl; or amino-, hydroxyl- or halogen-substituted $C_1$ to $C_4$ alkyl or $C_3$ to $C_6$ cycloalkyl, or $R^{N1}$ together with $R^{N2}$, and $R^{N3}$ together with $R^{N4}$ together with the N form an unsubstituted or methyl-, ethyl- propyl-, or halogen-substituted aziridine, pyrrolidine, piperidine, piperazine or morpholine and/or
$R^{10}$ is selected from
unsubstituted $C_2$ to $C_{12}$ alkyl or $C_3$ to $C_7$ cycloalkyl; or amino-, hydroxyl-, carboxyl- and halogen-substituted $C_2$ to $C_{12}$ alkyl or $C_3$ to $C_7$ cycloalkyl;
-$L^{A1}_n$-$L^{J1}_{n'}$'-$L^{A2}_m$-$L^{J2}_{m'}$'-$L^{A3}_p$-$L^{J3}_{p'}$'-$L^{A4}_q$-$L^{J4}_{q'}$'-$M_s$, wherein $L^{A1\cdots 4}$, $L^{J1\cdots 4}$, n, n' ... q', s and M have the definitions recited above.

10. The compound according to claim 1, wherein $R^2$ and $R^5$ are F or Cl.

11. The compound according to claim 1, wherein $R^1$, $R^2$, $R^3$, $R^4$, $R^5$, $R^6$ and $R^9$ are H,
$R^7$ and $R^8$ are $C_1$ to $C_4$ alkyl or phenyl,
$R^{N1}$, $R^{N2}$, $R^{N3}$ and $R^{N4}$ are individually unsubstituted or amino-, hydroxyl- or fluoro substituted $C_1$ to $C_4$ alkyl, or $R^{N1}$ together with $R^{N2}$, and $R^{N3}$ together with $R^{N4}$ together are —$(CH_2)_3$—, —$(CH_2)_4$—, —$(CH_2)_5$—, —$(CH_2)_2O(CH_2)_2$— or —$(CH_2)_2NH(CH_2)_2$— and
$R^{10}$ is selected from
unsubstituted or amino-, hydroxyl-, carboxyl- and fluoro substituted $C_2$ to $C_{12}$ alkyl or $C_3$ to $C_7$ cycloalkyl; or $R^{10}$ is -$L^{A1}_n$-$L^{J1}_{n'}$'-$L^{A2}_m$-$L^{J2}_{m'}$'-$L^{A3}_p$-$L^{J3}_{p'}$'-$L^{A4}_q$-$L^{J4}_{q'}$'-$M_s$, wherein $L^{A1\cdots 4}$, $L^{J1\cdots 4}$, n, n' ... q', s and M have the definitions recited above.

12. A compound selected from:
a. 4-(3,7-Bis(dimethylamino)-5,5-dimethyldibenzo[b,e]silin-10(5H)-ylidene)butanoic acid (2a);
b. 4-(3,7-Bis(dimethylamino)-5,5-dimethyldibenzo[b,e]silin-10(5H)-ylidene)-3-methylbutanoic acid (3a);
c. $N^3$,$N^3$,$N^7$,$N^7$,5,5-Hexamethyl-10-propylidene-5,10-dihydrodibenzo[b,e]siline-3,7-diamine (4a);
d. $N^3$,$N^3$,$N^7$,$N^7$,5,5-Hexamethyl-10-methylene-5,10-dihydrodibenzo[b,e]siline-3,7-diamine (5a);
e. 3-(3,7-Bis(dimethylamino)-5,5-dimethyldibenzo[b,e]silin-10(5H)-ylidene)propanoic acid (22);
f. 4-(3,7-Bis(dimethylamino)-5,5-dimethyldibenzo[b,e]silin-10(5H)-ylidene)-2,2-dimethylbutanoic acid (28);
g. 4-(3,7-Bis(dimethylamino)-5,5-diisopropyldibenzo[b,e]silin-10(5H)-ylidene)butanoic acid (6a);
h. 4-(3,7-Bis(dimethylamino)-2,8-difluoro-5,5-dimethyldibenzo[b,e]silin-10(5H)-ylidene)butanoic acid (36)
i. 3-(3,7-Di(azetidin-1-yl)-5,5-dimethyldibenzo[b,e]silin-10(5H)-ylidene)propanoic acid (42);
j. 4-(3,7-Bis(dimethylamino)-5,5-dimethyldibenzo[b,e]silin-10(5H)-ylidene)-N-(2-(2-((6-chlorohexyl)oxy)ethoxy)ethyl)butanamide (44);
k. 2,5-Dioxopyrrolidin-1-yl-4-(3,7-bis(dimethylamino)-5,5-dimethyldibenzo[b,e]silin-10(5H)-ylidene)butanoate (45);
l. N-(4-(((2-Amino-9H-purin-6-yl)oxy)methyl)benzyl)-4-(3,7-bis(dimethylamino)-5,5-dimethyldibenzo[b,e]silin-10(5H)-ylidene)butanamide (47);
m. N-(4-((4R,7R,10S,13S,19S,E)-7-((1H-Indol-2-yl)methyl)-4-(4-hydroxyphenyl)-8,13,15,19-tetramethyl-2,6,9,12-tetraoxo-1-oxa-5,8,11-triazacyclononadec-15-en-10-yl)butyl)-4-(3,7-bis(dimethylamino)-5,5-dimethyldibenzo[b,e]silin-10(5H)-ylidene)butanamide (49);
n. 4-(3,7-Bis(dimethylamino)-5,5-dimethyldibenzo[b,e]silin-10(5H)-ylidene)-N-(4-(4-(6-(4-methylpiperazin-1-yl)-1H,3'H-[2,5'-bibenzo[d]imidazol]-2'-yl)phenoxy)butyl)butanamide (51);
o. (2αR,4S,4αS,6R,9S,11S,12S,12αR,12βS)-12β-Acetoxy-9-((3-(4-(3,7-bis(dimethylamino)-5,5-dimethyldibenzo[b,e]silin-10(5H)-ylidene)butanamido)-2-hydroxy-3-phenylpropanoyl)oxy)-4,6,11-trihydroxy-4α,8,13,13-tetramethyl-5-oxo-2α,3,4,4α,5,6,9,10,11,12,12α,12β-dodecahydro-1H-7,11-methanocyclodeca[3,4]benzo[1,2-β]oxet-12-yl benzoate (53);
p. 8-(4-(3,7-Bis(dimethylamino)-5,5-dimethyldibenzo[b,e]silin-10(5H)-ylidene)butanamido)octanoic acid (55);
q. (2αR,4S,4αS,6R,9S,11S,12S,12αR,12βS)-12β-Acetoxy-9-((3-(8-(4-(3,7-bis(dimethylamino)-5,5-dimethyldibenzo[b,e]silin-10(5H)-ylidene)butanamido)octanamido)-2-hydroxy-3-phenylpropanoyl)oxy)-4,6,11-trihydroxy-4α,8,13,13-tetramethyl-5-oxo-2α,3,4,4α,5,6,9,10,11,12,12α,12β-dodecahydro-1H-7,11-methanocyclodeca[3,4]benzo[1,2-β]oxet-12-yl benzoate (56);
r. 4-(3,7-Bis(dimethylamino)-5,5-dimethyldibenzo[b,e]silin-10(5H)-ylidene)-N-(4-(6-methyl-1,2,4,5-tetrazin-3-yl)benzyl)butanamide (58);
s. 4-(3,7-Bis(dimethylamino)-5,5-diisopropyldibenzo[b,e]silin-10(5H)-ylidene)-N-(2-(2-((6-chlorohexyl)oxy)ethoxy)ethyl)butanamide (59);
t. 4-(3,7-Bis(dimethylamino)-5,5-diisopropyldibenzo[b,e]silin-10(5H)-ylidene)-N-(21-chloro-8-oxo-3,6,12,15-tetraoxa-9-azahenicosyl)butanamide (64);

u. 1-(4-(3,7-Bis(dimethylamino)-5,5-diisopropyldibenzo[b,e]silin-10(5H)-ylidene)butanamido)-N-(2-(2-((6-chlorohexyl)oxy)ethoxy)ethyl)-3,6,9,12-tetraoxapentadecan-15-amide (65);

v. N-(4-(((2-Amino-9H-purin-6-yl)oxy)methyl)benzyl)-4-(3,7-bis(dimethylamino)-5,5-diisopropyldibenzo[b,e]silin-10(5H)-ylidene)butanamide (66);

w. 3-((4-(((2-Amino-9H-purin-6-yl)oxy)methyl)benzyl)amino)-2-(4-(3,7-bis(dimethylamino)-5,5-diisopropyldibenzo[b,e]silin-10(5H)-ylidene)butanamido)-3-oxopropane-1-sulfonic acid (69);

x. N-(4-4R,7R,10S,13S,19S,E)-7-((1H-Indol-2-yl)methyl)-4-(4-hydroxyphenyl)-8,13,15,19-tetramethyl-2,6,9,12-tetraoxo-1-oxa-5,8,11-triazacyclononadec-15-en-10-yl)butyl)-4-(3,7-bis(dimethylamino)-5,5-diisopropyldibenzo[b,e]silin-10(5H)-ylidene)butanamide (70);

y. N-(4-(((2-Amino-9H-purin-6-yl)oxy)methyl)benzyl)-4-(3,7-bis(dimethylamino)-2,8-difluoro-5,5-dimethyldibenzo[b,e]silin-10(5H)-ylidene)butanamide (71);

z. N-(4-((4R,7R,10S,13S,19S,E)-7-((1H-Indol-2-yl)methyl)-4-(4-hydroxyphenyl)-8,13,15,19-tetramethyl-2,6,9,12-tetraoxo-1-oxa-5,8,11-triazacyclononadec-15-en-10-yl)butyl)-4-(3,7-bis(dimethylamino)-2,8-difluoro-5,5-dimethyldibenzo[b,e]silin-10(5H)-ylidene)butanamide (72).

13. A method to stain a sample, said method comprising the steps of:

a. contacting the sample with a compound according to claim 1, b. illuminating the sample with light of a wavelength ranging from 280 to 450 nm;

c. recording the presence and location of said compound in said sample by illuminating the sample with light of an appropriate excitation wavelength and recording light emitted from said sample at an appropriate emission wavelength.

14. The compound of claim 2, wherein M is selected from the group consisting of taxol, jasplakinolide, a bis-benzimide DNA stain, pepstatin A, triphenylphosphonium and an oligonucleotide having a sequence length of 10 to 40 nucleotides.

15. The compound of claim 4, wherein said moiety having a molecular weight between 15 and 1500 u is characterized by a general formula $L^{A1}{}_n\text{-}L^{J1}{}_n{}'\text{-}L^{A2}{}_m\text{-}L^{J2}{}_m{}'\text{-}L^{A3}{}_p\text{-}L^{J3}{}_p{}'\text{-}L^{A4}{}_q\text{-}L^{J4}{}_q{}'\text{-}M_s$, wherein $L^{A1}$, $L^{A2}$, $L^{A3}$ and $L^{A4}$ independently of each other are selected from $C_1$ to $C_{12}$ unsubstituted or amino-, hydroxyl-, carboxyl- or fluoro substituted alkyl or cycloalkyl, $(CH_2\text{—}CH_2\text{—}O)_r$ or $(CH_2\text{—}CH(OH)\text{—}CH_2\text{—}O)_r$ with r being an integer from 1 to 20, alkylaryl, alkylaryl-alkyl, and unsubstituted or alkyl-, halogen-, amino-, alkylamino-, imido-, nitro-, hydroxyl-oxyalkyl-, carbonyl-, carboxyl-, sulfuryl- and sulfoxyl substituted aryl or heteroaryl, $L^{J1}$, $L^{J2}$, $L^{J3}$ and $L^{J4}$ independently of each other are selected from —NR$^5$C(O)—, —C(O)N(R$^5$)—, —CN—, —NC—, —CO—, 'OC(O)—, —C(O)O—, —NR$^{N5}$—, —O—, —P(OOH)—, —OP(OOH)—, —P(OOH)O—, —OP(OOH)O—, —OP(OOH)O—, —S—, —SO—, SO$_2$—, with R$^{N5}$ selected from H and unsubstituted $C_1$ to $C_6$ alkyl, or amino-, hydroxyl-, carboxyl or fluoro substituted $C_1$ to $C_6$ alkyl, and n, n', m, m', p, p', q, q' and s independently from each other are selected from 0 and 1.

* * * * *